US009797010B2

(12) United States Patent
Weitz et al.

(10) Patent No.: US 9,797,010 B2
(45) Date of Patent: Oct. 24, 2017

(54) SYSTEMS AND METHODS FOR NUCLEIC ACID SEQUENCING

(75) Inventors: David A. Weitz, Bolton, MA (US); Jeremy Agresti, Sacramento, CA (US); Michael P. Weiner, Guilford, CT (US); Adam R. Abate, San Francisco, CA (US); Tony Hung, Peachtree City, GA (US)

(73) Assignee: President and Fellows of Harvard College, Cambridge, MA (US)

( * ) Notice: Subject to any disclaimer, the term of this patent is extended or adjusted under 35 U.S.C. 154(b) by 1402 days.

(21) Appl. No.: 12/809,120

(22) PCT Filed: Dec. 19, 2008

(86) PCT No.: PCT/US2008/013912
§ 371 (c)(1),
(2), (4) Date: Jun. 29, 2011

(87) PCT Pub. No.: WO2009/085215
PCT Pub. Date: Jul. 9, 2009

(65) Prior Publication Data
US 2011/0267457 A1  Nov. 3, 2011

Related U.S. Application Data

(60) Provisional application No. 61/008,862, filed on Dec. 21, 2007, provisional application No. 61/098,710, filed on Sep. 19, 2008.

(51) Int. Cl.
*C12Q 1/68* (2006.01)
(52) U.S. Cl.
CPC .................. *C12Q 1/6874* (2013.01)
(58) Field of Classification Search
None
See application file for complete search history.

(56) References Cited

U.S. PATENT DOCUMENTS

| 5,149,625 A | 9/1992 | Church et al. |
| 5,202,231 A | 4/1993 | Drmanac et al. |

(Continued)

FOREIGN PATENT DOCUMENTS

| EP | 0 249 007 A2 | 12/1987 |
| EP | 1 019 496 B1 | 9/2004 |

(Continued)

OTHER PUBLICATIONS

Invitation to Pay Additional Fees for PCT/US2008/003185 dated Oct. 22, 2008.

(Continued)

*Primary Examiner* — Samuel Woolwine
(74) *Attorney, Agent, or Firm* — Wolf, Greenfield & Sacks, P.C.

(57) ABSTRACT

The present invention relates to systems and methods for sequencing nucleic acids, including sequencing nucleic acids in fluidic droplets. In one set of embodiments, the method employs sequencing by hybridization using droplets such as microfluidic droplets. In some embodiments, droplets are formed which include a target nucleic acid, a nucleic acid probe, and at least one identification element, such as a fluorescent particle. The nucleic acid probes that hybridize to the target nucleic acid are determined, in some instances, by determining the at least one identification element. The nucleic acid probes that hybridize to the target nucleic acid may be used to determine the sequence of the target nucleic acid. In certain instances, the microfluidic droplets are provided with reagents that modify the nucleic acid probe. In some cases, a droplet, such as those described above, is deformed such that the components of the droplets individually pass a target area.

20 Claims, 44 Drawing Sheets

(56) References Cited

U.S. PATENT DOCUMENTS

| | | |
|---|---|---|
| 5,436,130 A | 7/1995 | Mathies et al. |
| 5,512,131 A | 4/1996 | Kumar et al. |
| 5,695,940 A | 12/1997 | Drmanac et al. |
| 5,736,330 A | 4/1998 | Fulton |
| 5,834,252 A | 11/1998 | Stemmer et al. |
| 5,851,769 A | 12/1998 | Gray et al. |
| 6,046,003 A | 4/2000 | Mandecki |
| 6,051,377 A | 4/2000 | Mandecki |
| 6,057,107 A | 5/2000 | Fulton |
| 6,103,537 A | 8/2000 | Ullman et al. |
| 6,297,006 B1 | 10/2001 | Drmanac et al. |
| 6,297,017 B1 | 10/2001 | Schmidt et al. |
| 6,355,198 B1 | 3/2002 | Kim et al. |
| 6,361,950 B1 | 3/2002 | Mandecki |
| 6,432,360 B1 | 8/2002 | Church |
| 6,485,944 B1 | 11/2002 | Church et al. |
| 6,511,803 B1 | 1/2003 | Church et al. |
| 6,524,456 B1 | 2/2003 | Ramsey et al. |
| 6,586,176 B1 | 7/2003 | Trnovsky et al. |
| 6,632,606 B1 | 10/2003 | Ullman et al. |
| 6,670,133 B2 | 12/2003 | Knapp et al. |
| 6,767,731 B2 | 7/2004 | Hannah |
| 6,800,298 B1 | 10/2004 | Burdick et al. |
| 6,806,058 B2 | 10/2004 | Jesperson et al. |
| 6,913,935 B1 | 7/2005 | Thomas |
| 6,929,859 B2 | 8/2005 | Chandler et al. |
| 7,041,481 B2 | 5/2006 | Anderson et al. |
| 7,129,091 B2 | 10/2006 | Ismagilov et al. |
| 7,268,167 B2 | 9/2007 | Higuchi et al. |
| 7,425,431 B2 | 9/2008 | Church et al. |
| 7,536,928 B2 | 5/2009 | Kazuno |
| 7,604,938 B2 | 10/2009 | Takahashi et al. |
| 7,638,276 B2 | 12/2009 | Griffiths et al. |
| 7,708,949 B2 | 5/2010 | Stone et al. |
| RE41,780 E | 9/2010 | Anderson et al. |
| 7,799,553 B2 | 9/2010 | Mathies et al. |
| 7,968,287 B2 | 6/2011 | Griffiths et al. |
| 8,252,539 B2 | 8/2012 | Quake et al. |
| 8,273,573 B2 | 9/2012 | Ismagilov et al. |
| 8,278,071 B2 | 10/2012 | Brown et al. |
| 8,304,193 B2 | 11/2012 | Ismagilov et al. |
| 8,329,407 B2 | 12/2012 | Ismagilov et al. |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagliov et al. |
| 8,871,444 B2 | 10/2014 | Griffiths et al. |
| 8,889,083 B2 | 11/2014 | Ismagilov et al. |
| 9,029,083 B2 | 5/2015 | Griffiths et al. |
| 9,029,085 B2 | 5/2015 | Agresti et al. |
| 9,056,289 B2 | 6/2015 | Weitz et al. |
| 9,068,210 B2 | 6/2015 | Agresti et al. |
| 2001/0020588 A1 | 9/2001 | Adourian et al. |
| 2001/0044109 A1* | 11/2001 | Mandecki ............... 435/6 |
| 2002/0034737 A1 | 3/2002 | Drmanac |
| 2002/0034747 A1 | 3/2002 | Bruchez et al. |
| 2002/0051992 A1 | 5/2002 | Bridgham et al. |
| 2002/0058332 A1 | 5/2002 | Quake et al. |
| 2002/0092767 A1 | 7/2002 | Bjornson et al. |
| 2002/0179849 A1 | 12/2002 | Maher et al. |
| 2003/0008285 A1 | 1/2003 | Fischer |
| 2003/0008323 A1 | 1/2003 | Ravkin et al. |
| 2003/0028981 A1 | 2/2003 | Chandler et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0099954 A1 | 5/2003 | Miltenyi et al. |
| 2003/0104466 A1 | 6/2003 | Knapp et al. |
| 2003/0108897 A1 | 6/2003 | Drmanac |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0063138 A1 | 4/2004 | McGinnis et al. |
| 2004/0132122 A1 | 7/2004 | Banerjee et al. |
| 2005/0019839 A1 | 1/2005 | Jespersen et al. |
| 2005/0042625 A1 | 2/2005 | Schmidt et al. |
| 2005/0136486 A1 | 6/2005 | Haushalter |
| 2005/0172476 A1 | 8/2005 | Stone et al. |
| 2005/0181379 A1 | 8/2005 | Su et al. |
| 2005/0221339 A1 | 10/2005 | Griffiths et al. |
| 2005/0244850 A1 | 11/2005 | Huang et al. |
| 2005/0287572 A1 | 12/2005 | Mathies et al. |
| 2006/0020371 A1 | 1/2006 | Ham et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0240506 A1 | 10/2006 | Kushmaro et al. |
| 2006/0257893 A1 | 11/2006 | Takahashi et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0054119 A1 | 3/2007 | Garstecki et al. |
| 2007/0092914 A1 | 4/2007 | Griffiths et al. |
| 2007/0172873 A1 | 7/2007 | Brenner et al. |
| 2007/0195127 A1 | 8/2007 | Ahn et al. |
| 2007/0228588 A1 | 10/2007 | Noritomi et al. |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2009/0012187 A1 | 1/2009 | Chu et al. |
| 2009/0035770 A1 | 2/2009 | Mathies et al. |
| 2009/0068170 A1 | 3/2009 | Weitz et al. |
| 2009/0131543 A1 | 5/2009 | Weitz et al. |
| 2009/0197248 A1 | 8/2009 | Griffiths et al. |
| 2009/0197772 A1 | 8/2009 | Griffiths et al. |
| 2009/0286687 A1 | 11/2009 | Dressman et al. |
| 2010/0022414 A1 | 1/2010 | Link et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston, Jr. et al. |
| 2010/0210479 A1 | 8/2010 | Griffiths et al. |
| 2011/0086780 A1 | 4/2011 | Colston et al. |
| 2011/0092392 A1 | 4/2011 | Colston et al. |
| 2011/0160078 A1 | 6/2011 | Fodor et al. |
| 2011/0218123 A1 | 9/2011 | Weitz et al. |
| 2012/0010098 A1 | 1/2012 | Griffiths et al. |
| 2012/0010107 A1 | 1/2012 | Griffiths et al. |
| 2012/0015382 A1 | 1/2012 | Weitz et al. |
| 2012/0015822 A1 | 1/2012 | Weitz et al. |
| 2012/0190032 A1 | 7/2012 | Ness et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2013/0079231 A1 | 3/2013 | Pushkarev et al. |
| 2013/0109575 A1 | 5/2013 | Kleinschmidt et al. |
| 2013/0157899 A1 | 6/2013 | Adler et al. |
| 2013/0210639 A1 | 8/2013 | Link et al. |
| 2013/0274117 A1 | 10/2013 | Church et al. |
| 2014/0155295 A1 | 6/2014 | Hindson et al. |
| 2014/0194323 A1 | 7/2014 | Gillevet |
| 2014/0199730 A1 | 7/2014 | Agresti et al. |
| 2014/0199731 A1 | 7/2014 | Agresti et al. |
| 2014/0227684 A1 | 8/2014 | Hindson et al. |
| 2014/0235506 A1 | 8/2014 | Hindson et al. |
| 2014/0303039 A1 | 10/2014 | Weitz et al. |
| 2014/0378349 A1 | 12/2014 | Hindson et al. |
| 2015/0005200 A1 | 1/2015 | Hindson et al. |
| 2015/0314292 A1 | 11/2015 | Weitz et al. |
| 2015/0336068 A1 | 11/2015 | Weitz et al. |
| 2015/0336069 A1 | 11/2015 | Weitz et al. |
| 2015/0336070 A1 | 11/2015 | Weitz et al. |
| 2015/0336071 A1 | 11/2015 | Weitz et al. |
| 2015/0336072 A1 | 11/2015 | Weitz et al. |
| 2015/0337371 A1 | 11/2015 | Weitz et al. |
| 2015/0353999 A1 | 12/2015 | Agresti et al. |

FOREIGN PATENT DOCUMENTS

| | | |
|---|---|---|
| EP | 1 482 036 B1 | 10/2007 |
| EP | 1 594 980 B1 | 11/2009 |

(56) References Cited

FOREIGN PATENT DOCUMENTS

| | | |
|---|---|---|
| EP | 1 967 592 B1 | 4/2010 |
| EP | 2 258 846 A2 | 12/2010 |
| EP | 2 145 955 B1 | 2/2012 |
| EP | 2145955 B1 | 2/2012 |
| EP | 1 905 828 B1 | 8/2012 |
| EP | 1905828 B1 | 8/2012 |
| EP | 1 908 832 B1 | 12/2012 |
| EP | 1908832 B1 | 12/2012 |
| EP | 2 540 389 A1 | 1/2013 |
| JP | S59-049832 A2 | 3/1984 |
| JP | 2004-361291 A | 12/2004 |
| JP | 2006-507921 T2 | 3/2006 |
| JP | 2006-289250 A | 10/2006 |
| JP | 2007-268350 A | 10/2007 |
| JP | 2007-298327 A | 11/2007 |
| JP | 2009-208074 A2 | 9/2009 |
| WO | WO 96/29629 A2 | 9/1996 |
| WO | WO 96/41011 A1 | 12/1996 |
| WO | WO 99/09217 A1 | 2/1999 |
| WO | WO 99/52708 A1 | 10/1999 |
| WO | WO 00/08212 A1 | 2/2000 |
| WO | WO 00/26412 A1 | 5/2000 |
| WO | WO 01/14589 A2 | 3/2001 |
| WO | WO 01/89787 A2 | 11/2001 |
| WO | WO 02/31203 A2 | 4/2002 |
| WO | WO 02/086148 A1 | 10/2002 |
| WO | WO 2004/002627 A2 | 8/2004 |
| WO | WO 2004/087308 A1 | 10/2004 |
| WO | WO 2004/088314 A1 | 10/2004 |
| WO | WO 2004/091763 A2 | 10/2004 |
| WO | WO 2004/102204 | 11/2004 |
| WO | WO 2004/103565 | 12/2004 |
| WO | WO 2005/021151 A1 | 3/2005 |
| WO | WO 2005/040406 A1 | 5/2005 |
| WO | WO 2005/049787 A2 | 6/2005 |
| WO | WO 2005/082098 A2 | 9/2005 |
| WO | WO 2006/078841 A1 | 7/2006 |
| WO | WO 2006/096571 A2 | 9/2006 |
| WO | WO 2007/001448 A2 | 1/2007 |
| WO | WO 2007/002490 A2 | 1/2007 |
| WO | WO 2007/024840 A2 | 3/2007 |
| WO | WO 2007/081385 A2 | 7/2007 |
| WO | WO 2007/081387 A1 | 7/2007 |
| WO | WO 2007/089541 A2 | 8/2007 |
| WO | WO 2007/114794 | 10/2007 |
| WO | WO 2007/121489 A2 | 10/2007 |
| WO | WO 2007/133710 | 11/2007 |
| WO | WO 2007/138178 | 12/2007 |
| WO | WO 2007/139766 A2 | 12/2007 |
| WO | WO 2007/140015 A2 | 12/2007 |
| WO | WO 2007/149432 A2 | 12/2007 |
| WO | WO 2008/021123 A1 | 2/2008 |
| WO | WO 2008/091792 A2 | 7/2008 |
| WO | WO 2008/102057 A1 | 8/2008 |
| WO | WO 2008/134153 A1 | 11/2008 |
| WO | WO 2008/109176 A2 | 12/2008 |
| WO | WO 2009/005680 A1 | 1/2009 |
| WO | WO 2009/011808 A1 | 1/2009 |
| WO | WO 2009/085215 A1 | 7/2009 |
| WO | WO 2010/151776 A2 | 12/2010 |
| WO | WO 2011/056546 A1 | 5/2011 |
| WO | WO 2012/048341 A1 | 4/2012 |
| WO | WO 2013/177220 A1 | 11/2013 |

OTHER PUBLICATIONS

International Preliminary Report on Patentability for PCT/US2008/003185 dated Sep. 17, 2009.
International Preliminary Report on Patentability for PCT/US2008/013912 dated Jul. 1, 2010.
Invitation to Pay Additional Fees for PCT Application PCT/US09/005184 dated May 27, 2010.
International Search Report from PCT Application PCT/US09/005184 dated Aug. 16, 2010.
International Preliminary Report on Patentability for PCT Application PCT/US09/005184 dated Mar. 31, 2011.
International Search Report and Written Opinion for International Application No. PCT/US2009/006649 dated Mar. 10, 2010.
International Preliminary Report on Patentability for International Application No. PCT/US2009/006649 dated Jun. 30, 2011.
Office Action dated Jan. 23, 2012 for EP 08865992.5.
Abate et al., Valve-based flow focusing for drop formation. Appl Phys Lett. 2009;94. 3 pages.
Braeckmans et al., Scanning the Code. Modern Drug Discovery. 2003:28-32.
Chechetkin et al., Sequencing by hybridization with the generic 6-mer oligonucleotide microarray: an advanced scheme for data processing. J Biomol Struct Dyn. Aug. 2000;18(1):83-101.
De Bruin et al., UBS Investment Research. Q-Series®: DNA Sequencing. UBS Securities LLC. Jul. 12, 2007. 15 pages.
Drmanac eta l., Sequencing by hybridization (SBH): advantages, achievements, and opportunities. Adv Biochem Eng Biotechnol. 2002;77:75-101.
Fulton et al., Advanced multiplexed analysis with the FlowMetrix system. Clin Chem. Sep. 1997;43(9):1749-56.
Khomiakova et al., [Analysis of perfect and mismatched Dna duplexes by a generic hexanucleotide microchip]. Mol Biol (Mosk). Jul.-Aug. 2003;37(4):726-41. Russian.
Mouritzen et al., Single nucleotide polymorphism genotyping using locked nucleic acid (LNA). Expert Rev Mol Diagn. Jan. 2003;3(1):27-38.
Schirinzi et al., Combinatorial sequencing-by-hybridization: analysis of the NF1 gene. Genet Test. 2006 Spring;10(1):8-17.
Simeonov et al., Single nucleotide polymorphism genotyping using short, fluorescently labeled locked nucleic acid (LNA) probes and fluorescence polarization detection. Nucleic Acids Res. Sep. 1, 2002;30(17):e91. pp. 1-5.
Sorokin et al., Discrimination between perfect and mismatched duplexes with oligonucleotide gel microchips: role of thermodynamic and kinetic effects during hybridization. J Biomol Struct Dyn. Jun. 2005;22(6):725-34.
Wang et al., Single nucleotide polymorphism discrimination assisted by improved base stacking hybridization using oligonucleotide microarrays. Biotechniques. 2003;35:300-08.
Australian Office Action dated Dec. 17, 2013 for Application No. AU 2010315580.
Chinese Office Action dated Dec. 24, 2013 for CN Application No. 200880127116.4.
Chinese Office Action dated Dec. 16, 2013 for CN Application No. 201080055990.9.
Interview Summary dated Feb. 12, 2014 for U.S. Appl. No. 12/529,926.
Office Action dated May 20, 2014 for U.S. Appl. No. 14/172,266.
Office Action dated May 20, 2014 for U.S. Appl. No. 14/172,326.
Office Action dated Apr. 29, 2014 for EP Application No. 08865992.5.
Final Office Action dated Dec. 5, 2013 for U.S. Appl. No. 13/119,470.
Advisory Action dated Mar. 21, 2014 for U.S. Appl. No. 13/119,470.
Notice of Allowance dated Jan. 27, 2014 for U.S. Appl. No. 13/139,326.
Office Action dated Feb. 10, 2014 for U.S. Appl. No. 13/503,588.
Advisory Action dated May 16, 2014 for U.S. Appl. No. 13/503,588.
Boone, et al. Plastic advances microfluidic devices. The devices debuted in silicon and glass, but plastic fabrication may make them hugely successful in biotechnology application. Analytical Chemistry. Feb. 2002; 78A-86A.
Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566 pp. 1-6.
[No Author] Microfluidic ChipShop. Microfluidic product catalogue. Mar. 2005. pp. 1-18.
[No Author] Microfluidic ChipShop. Microfluidic product catalogue. Oct. 2009. pp. 1-48

(56) References Cited

OTHER PUBLICATIONS

Chinese Office Action and search report dated May 23, 2013 for Application No. CN200880127116.4.
Final Office Action dated May 28, 2013 for U.S. Appl. No. 12/529,926.
Final Office Action dated Aug. 6, 2013 for U.S. Appl. No. 13/139,326.
International Search Report and Written Opinion of the International Searching Authority for International Application No. PCT/US2008/003185, dated Jan. 22, 2009.
International Search Report and Written Opinion of the International Searching Authority for International Application No. PCT/US2008/008563, dated Oct. 29, 2008.
Office Action from U.S. Appl. No. 12/172,186, dated Jan. 4, 2010.
Agresti, "Selection of ribozymes that catalyse multiple-turnover Diels-Alder cycloadditions by using in vitro compartmentalization", *PNAS*, 102, 16170-16175 (2005).
Akselband, "Enrichment of slow-growing marine microorganisms from mixed cultures using gel microdrop (GMD) growth assay and fluorescence-activated cell sorting", *J. Exp. Marine Biol.*, 329: 196-205 (2006).
Akselband, "Rapid mycobacteria drug susceptibility testing using gel microdrop (GMD) growth assay and flow cytometry", *J. Microbiol. Methods*, 62:181-197 (2005).
Anna et al., "Formation of dispersions using 'flow focusing' in microchannels", *Appln. Phys. Letts.* 82:3364 (2003). pp. 364-366.
Carroll, "The selection of high-producing cell lines using flow cytometry and cell sorting", *Exp. Op. Biol. Therp.*, 4:11 1821-1829 (2004).
Chaudhary, V. et al. "A rapid method of cloning functional variable-region antibody genes in *Escherichia coli* as single-chain immunotoxins" *Proc. Natl. Acad. Sci.*, vol. 87, pp. 1066-1070, Feb. 1990, pp. 1066-1070.
Clausell-Tormos et al., "Droplet-based microfluidic platforms for the encapsulation and screening of mammalian cells and multicellular organisms", *Chem. Biol.* 15:427-437 (2008).
Diaz, R.V., et al., "One-Month sustained release microspheres of 125 I-bovine calcitonin In vitro-in vivo studies," *Journal of Controlled Release*, vol. 59, pp. 55-62 (1999).
Doerr, "The smallest bioreactor", *Nature Methods*, 2:5 326 (2005).
Droplet Based Sequencing (slides) dated (Mar. 12, 2008). Abate et al.
Fu, "A microfabricated fluorescence-activated cell sorter", *Nature Biotech.*, 17:1109-1111 (1997).
He, M. et al. "Selective Encapsulation of Single Cells and Subcellular Organelles into Picoliter- and Femtoliter-Volume Droplets" Anal. Chem. 2005, 77, 1539-1544.
Huebner, "Quantitative detection of protein expression in single cells using droplet microfluidics", *Chem. Commun.* 1218-1220 (2007).
Koster et al., "Drop-based microfluidic devices for encapsulation of single cells", *Lab on a Chip The Royal Soc. of Chem.* 8:1110-1115 (2008).
Li, Y., et al., "PEGylated PLGA nanoparticles as protein carriers: synthesis, preparation and biodistribution in rats," *Journal of Controlled Release*, vol. 71, pp. 203-211 (2001).
Loscertales, "Micro/Nano encapsulation via electrified coaxial liquid jets", *Science* 295:(2002).
Love, "A microengraving method for rapid selection of single cells producing antigen-specific antibodies", *Nature Biotech*, 24:6 (Jun. 2006). pp. 703-706.
Mirzabekov, A. "DNA sequencing by hybridization—a megasequencing method and a diagnostic tool?" Trends Biotech, 12: 27-32, Jan. 1994.
Nguyen, "In situ hybridization to chromosomes stabilized in gel microdrops", *Cytometry*, 21:111-119 (1995).
Okushima, "Controlled production of monodisperse double emulsions by two-step droplet breakup in microfluidic devices", *Langmuir*, 20:9905-9908 (2004).

Perez, C., et al., "Poly(lactic acid)-poly(ethylene glycol) nanoparticles as new carriers for the delivery of plasmid DNA," *Journal of Controlled Release*, vol. 75, pp. 211-224 (2001).
Ryan, "Rapid assay for mycobacterial growth and antibiotic susceptibility using gel microdrop and encapsulation", *J. Clinical Microbiol.*, 33:7 1720-1726 (1995).
Schmitt, "Bead-based multiplex genotyping of human papillomaviruses", *J. Clinical Microbiol.*, 44:2 504-512 (2006).
Shah, "Fabrication of monodisperse thermosensitive microgels and gel capsules in microfluidic devices", *Soft Matter*, 4:2303-2309 (2008).
Weaver, "Rapid clonal growth measurements at the single-cell level: gel microdroplets and flow cytometry", *Biotechnology*, 9:873-877 (1991).
Whitesides, "Soft lithography in biology and biochemistry", *Annual Review of Biomedical Engineering*, 3:335-373 (2001).
Xia, "Soft lithography", *Annual Review of Material Science*, 28:153-184 (1998).
Zhang, "Combinatorial marking of cells and organelles with reconstituted fluorescent proteins", *Cell*, 119:137-144 (Oct. 1, 2004).
Zhao, J., et al., "Preparation of hemoglobin-loaded nano-sized particles with porous structure as oxygen carriers," *Biomaterials*, vol. 28, pp. 1414-1422 (2007).
Zimmerman, "Microscale production of hybridomas by hypo-osmolar electrofusion", *Hum. Antibody Hybridomas*, 3 (Jan. 1992). pp. 14-18.
Office Communication dated Aug. 29, 2013 for Application No. EP 08865992.5.
Office Action dated Sep. 17, 2013 for U.S. Appl. No. 13/503,588.
Japanese Office Action dated Jul. 17, 2013 for Application No. JP 2010-539498.
Japanese Office Action dated Nov. 19, 2013 for Application No. JP 2012-536941.
Advisory Action dated Nov. 20, 2013 for U.S. Appl. No. 13/139,326.
Office Action dated Jun. 18, 2012 for CN Application No. 200880127116.4.
International Preliminary Report on Patentability from PCT Application PCT/US2010/054050 dated May 10, 2012.
Office Action dated Oct. 1, 2012 for U.S. Appl. No. 12/529,926.
Office Action dated Feb. 28, 2013 for U.S. Appl. No. 13/139,326.
Su et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese Journal Experimental Surgery. May 2005;22(5):639-40.
Office Communication dated Apr. 5, 2013 for Application No. EP 08865992.5.
Office Action dated Apr. 24, 2013 for U.S. Appl. No. 13/119,470.
International Search Report from PCT Application PCT/US10/054050 dated Jan. 31, 2011.
European Office Action from European Application 08865992.5 dated Dec. 15, 2010.
European Office action dated Nov. 7, 2014 for Application No. 09804166.8.
Final Office Action dated Nov. 21, 2014 for U.S. Appl. No. 14/172,266.
Final Office Action dated Nov. 20, 2014 for U.S. Appl. No. 14/172,326.
Holtze et al., Biocompatible surfactants for water-in-fluorocarbon emulsions. Lab Chip. Oct. 2008; 8(10):1632-9.
Mazutis et al., Selective droplet coalescence using microfluidic systems. Lab Chip. Apr. 24, 2012; 12(10):1800-6.
International Search Report and Written Opinion of the International Searching Authority for International Application No. PCT/US2008/013912, dated Apr. 3, 2009.
International Search Report and Written Opinion of the International Searching Authority for International Application No. PCT/US2009/004037, dated Oct. 2, 2009.

(56) References Cited

OTHER PUBLICATIONS

International Search Report and Written Opinion of the International Searching Authority for International Application No. PCT/US2009/003389, dated Oct. 21, 2009.
International Search Report and Written Opinion for International Application No. PCT/US2009/006649, dated Mar. 10, 2010.
Japanese Office Action dated Sep. 2, 2014 for Application No. JP 2010-539498.
Chinese Office Action dated Jul. 30, 2014 for Application No. CN 201080055990.9.
Japanese Final Rejection dated Aug. 5, 2014 for Application No. JP 2012-536941.
Office Action dated Aug. 6, 2014 for U.S. Appl. No. 12/529,926.
Chou, et al. Disposable Microdevices for DNA Analysis and Cell Sorting. Proc. Solid-State Sensor and Actuator Workshop, Hilton Head, SC. Jun. 8-11, 1998; 11-14.
Chu, L., et al., "Controllable Monodisperse Multiple Emulsions," Angew. Chem. Int. Ed. 2007; 46: 8970-8974.
Ghadessy et al. Directed evolution of polymerase function by compartmentalized self-replication. Proc Natl Acad Sci USA. Apr. 10, 2001; 98(8):4552-7. Epub Mar. 27, 2001.
Hug et al. Measurement of the number of molecules of a single mRNA species in a complex mRNA preparation. J Theor Biol. Apr. 21, 2003; 221(4):615-24.
Kim, J., et al, "Albumin loaded microsphere of amphiphilic poly-(ethylene glycol)/poly(a-ester) multiblock copolymer," European Journal of Pharmaceutical Sciences, vol. 23, pp. 245-251(2004).
Kim, "Fabrication of monodisperse gel shells and functional microgels in microfluidic devices", Angew. Chem., 119:1851-1854 (2007).
Tawfik, et al. Man-made cell-like compartments for molecular evolution. Nat Biotechnol. Jul. 1998;16(7):652-6.
Van De Hulst et al., Glare points. Appl Opt. Nov. 20, 1991;30(33):4755-63.
Office Action dated Jan. 6, 2016 for U.S. Appl. No. 14/812,930.
Office Action dated Jan. 6, 2016 for U.S. Appl. No. 14/262,895.
Office Action dated Apr. 27, 2016 for U.S. Appl. No. 14/262,895.
[No Author] Gene Characterization Kits. Stratagene Catalog. Statagene Cloning Systems: Tools and Technology for Lift Sciences. 1988. 3 pages.
Griffiths et al., Directed evolution of an extremely fast phosphotriesterase by in vitro compartmentalization. EMBO J. Jan. 2, 2003;22(1):24-35.
Nisisako et al., Formation of droplets using branch channels in a microfluidic circuit. SICE. OSAKA. Aug. 5-7, 2002. 957-959.
Taniguchi et al., Chemical reactions in microdroplets by electrostatic manipulation of droplets in liquid media. Lab Chip. Feb. 2002;2(1):19-23. DOI: 10.1039/B108739H.
Thorsen, et al. Dynamic pattern formation in a vesicle-generating microfluidic device. Physical Review Letters. American Physical Society. 2001; 86(18):4163-4166.
Umbanhowar, et al. Monodisperse emulsion generation via drop break off in a coflowing stream. Langmuir. 2000; 16:347-351.

\* cited by examiner

XXXX   X = NUCLEIC ACID RESIDUE

Fig. 2A

XXXXX

Fig. 2B

XXXXX

XXLXX ~~~ Ⓢ   L = LOCKED NUCLEIC ACID RESIDUE

Fig. 2F

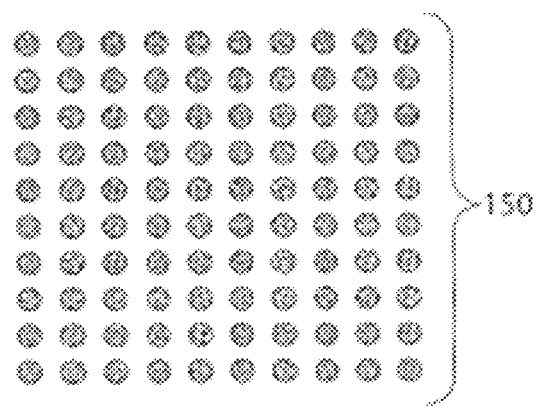
Fig. 6A
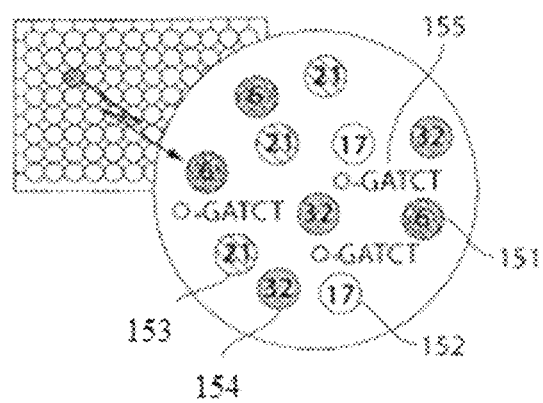
Fig. 6B
Fig. 6C

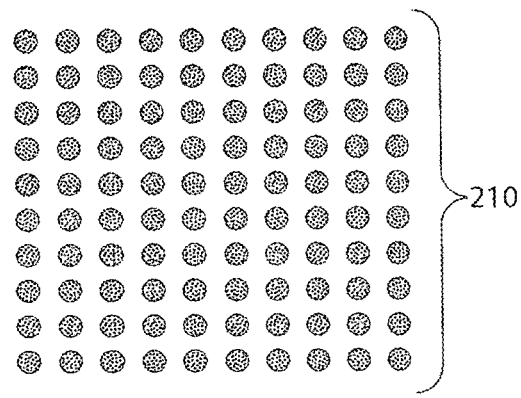
Fig. 8A
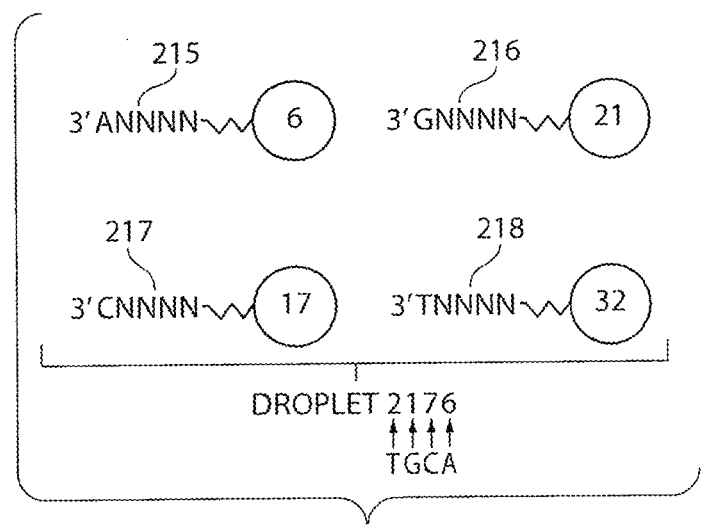
Fig. 8B
Fig. 8C

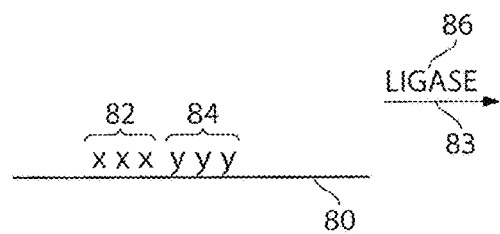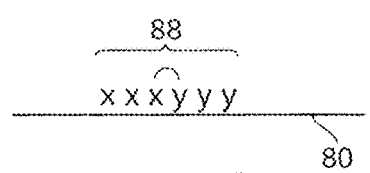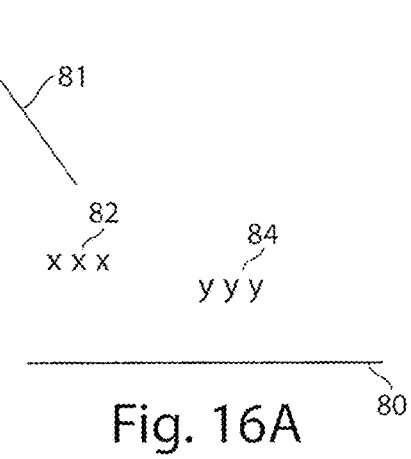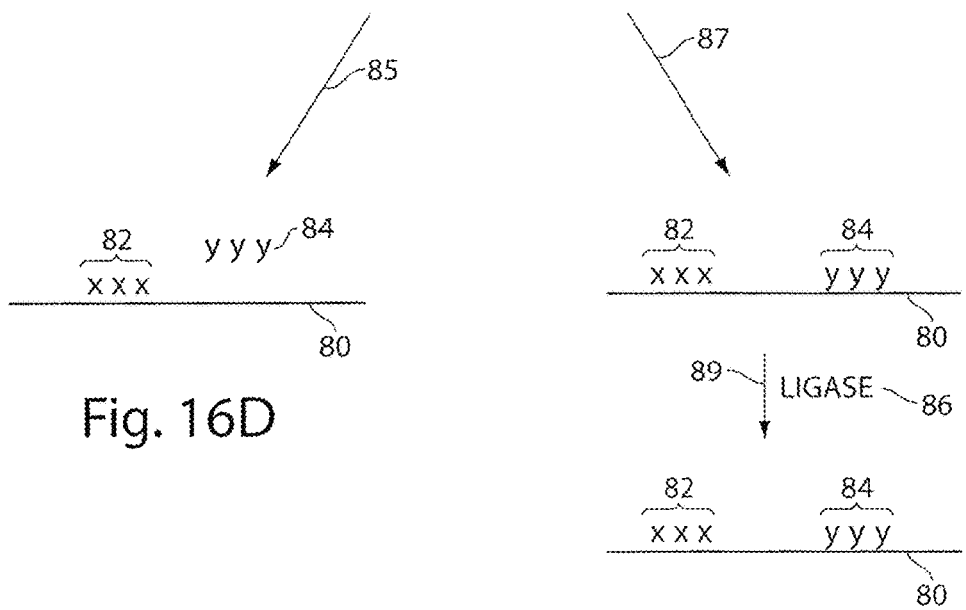

SYSTEMS AND METHODS FOR NUCLEIC ACID SEQUENCING

RELATED APPLICATIONS

This application claims the benefit of U.S. Provisional Patent Application Ser. No. 61/008,862, filed Dec. 21, 2007, entitled "Systems and Methods for Nucleic Acid Sequencing," by Weitz, et al., and U.S. Provisional Patent Application Ser. No. 61/098,710, filed Sep. 19, 2008, entitled "Systems and Methods for Nucleic Acid Sequencing," by Weitz, et al., each incorporated herein by reference.

GOVERNMENT FUNDING

This invention was made with government support under DMR-0602684 awarded by the National Institutes of Health. The government has certain rights in the invention.

FIELD OF INVENTION

The present invention relates to systems and methods for sequencing nucleic acids, including sequencing nucleic acids in fluidic droplets.

BACKGROUND

The ability to determine nucleic acid sequences is important for applications such as understanding the function and control of genes, or for applying many of the basic techniques of molecular biology. Sequencing by hybridization (SBH) is an approach to DNA sequencing that has been recently developed. In sequencing by hybridization, a large set of single-stranded fragments or probes are attached to a substrate. A solution of labeled single-stranded target DNA fragments is exposed to the substrate. These fragments hybridize with the complementary fragments on the substrate, and the hybridized fragments can be identified using a detector or a fluorescent/phosphorescent dye, depending on the selected label. The target DNA is then sequenced based on the pattern of hybridization of the fragments with the chip. However, current SBH techniques have several problems that limit their application, such as requiring relatively large quantities of reagents, or having relatively small throughput.

SUMMARY OF THE INVENTION

The present invention relates to systems and methods for sequencing nucleic acids, including sequencing nucleic acids in fluidic droplets. The subject matter of the present invention involves, in some cases, interrelated products, alternative solutions to a particular problem, and/or a plurality of different uses of one or more systems and/or articles.

In one aspect, the invention is directed to a method. According to a first set of embodiments, the method includes acts of providing a first microfluidic droplet containing a nucleic acid probe and at least one identification element, providing a second microfluidic droplet comprising a target nucleic acid, and fusing the first fluidic droplet and the second fluidic droplet to form a fused droplet. In another set of embodiments, the method includes acts of providing a microfluidic droplet comprising a plurality of identification elements, deforming the droplet and passing the droplet past a target area such that each of the plurality of identification elements individually passes the target area, and determining each of the plurality of identification elements passing through the target area.

The method, in accordance with yet another set of embodiments, includes acts of determining at least a portion of a droplet containing a nucleic acid probe by adding, to the droplet, a first identification element, a second identification element distinguishable from the first identification element, and a third identification element distinguishable from the first and second identification element.

In one set of embodiments, the method includes acts of defining at least six distinguishable identification elements where the identification elements are arranged into at least three groups with each group having at least two of the elements, associating each of at least eight distinguishable species with at least one identification element selected from each of the at least three groups such that no two of the at least eight distinguishable species is associated with the same set of identification elements, and preparing at least eight distinguishable droplets, where each droplet contains one of the at least eight different species and the associated elements taken from each of the at least three groups.

In still another set of embodiments, the method includes acts of providing a plurality of distinguishable nucleic acid probes and a plurality of distinguishable identification elements, selecting one nucleic acid probe from the plurality of nucleic acid probes and at least three distinguishable identification elements from the plurality of distinguishable identification elements, forming a fluidic droplet containing the selected one nucleic acid probe and the at least three distinguishable identification elements, and repeating the selecting and forming steps to form a population of fluidic droplets, including at least ten distinguishable fluidic droplets. In some cases, each droplet contains one nucleic acid probe and the at least three distinguishable identification elements.

In another aspect, the invention is directed to a kit. In some cases, the kit comprises a first plurality of at least 10 distinguishable fluidic droplets where each droplet contains a nucleic acid probe, and a second plurality of at least 10 distinguishable fluidic droplets where each droplet contains at least three distinguishable identification elements.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 2A-2F show non-limiting examples of nucleic acid probes.

FIGS. 6A-6D, 7A-7C and 8A-8G depict non-limiting examples of methods for sequencing a target nucleic acid.

FIGS. 16A-16E depict a method of ligating a first and a second nucleic acid probe, in one embodiment of the invention.

BRIEF DESCRIPTION OF THE SEQUENCES

Figure 1:
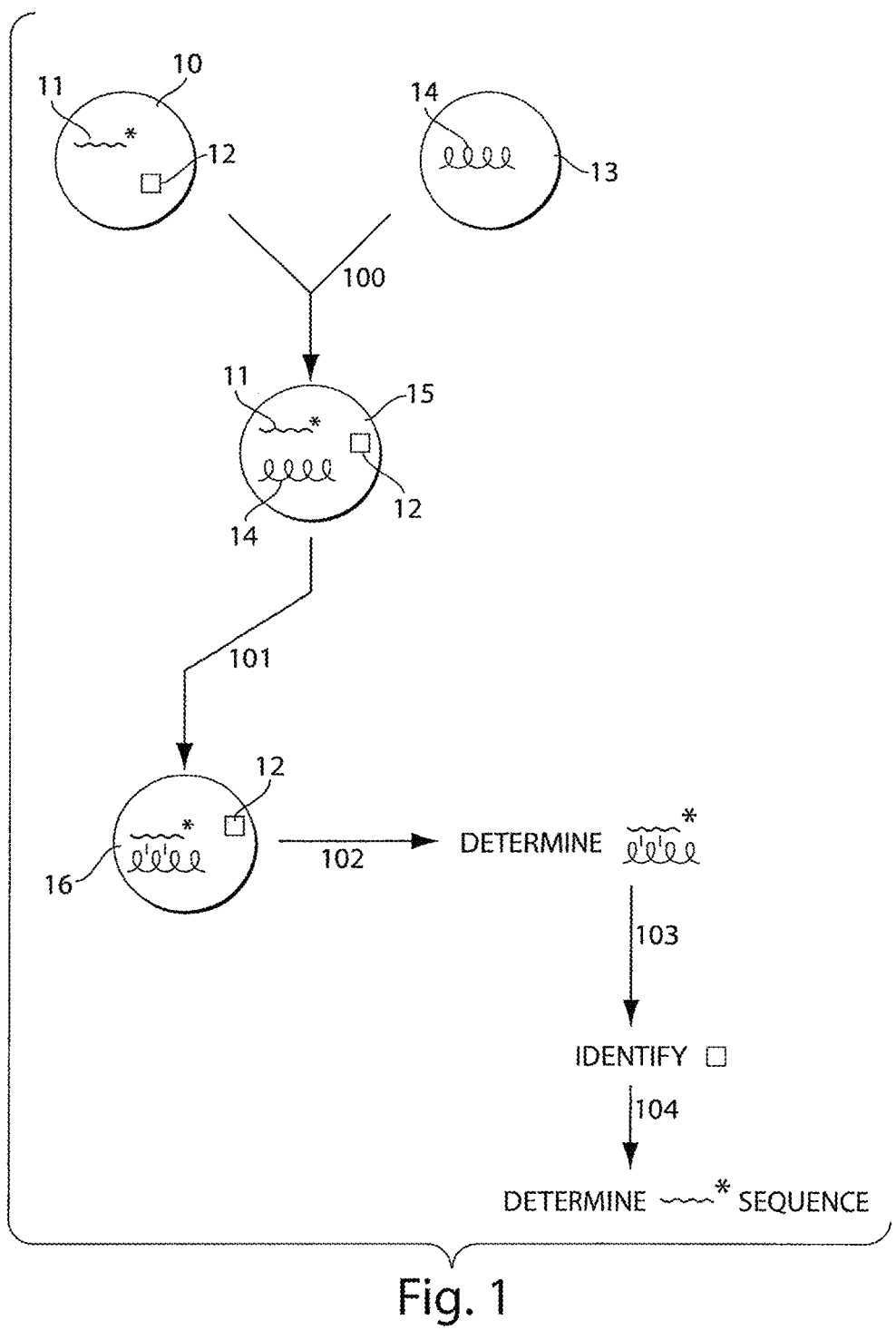
FIG. 1 shows a method for sequencing a target nucleic acid in one embodiment of the invention.

SEQ ID NO: 1 is ACTTCG, a synthetic DNA sequence;
SEQ ID NO: 2 is *GATCC, a synthetic DNA sequence, where * is a signaling entity;
SEQ ID NO: 3 is GATCTGNNNN, a synthetic DNA sequence, where N is a universal base;
SEQ ID NO: 4 is CATATC, a synthetic DNA sequence;
SEQ ID NO: 5 is GATCTNGNNN, a synthetic DNA sequence, where N is a universal base;
SEQ ID NO: 6 is CXACATC, a synthetic DNA sequence, where X is one of A, C, G or T;
SEQ ID NO: 7 is GACTCTGTCCCTCCCTTGTCTAC-CCTGTGCGTCCCTACTCTACC, a synthetic DNA sequence;
SEQ ID NO: 8 is biotin-CCTATCCCCTGTGTGCCTT-GCCTATCCCCTGTTGCGTGTCTCAG, a synthetic DNA sequence;
SEQ ID NO: 9 is CTAAGTTA, a synthetic DNA sequence;
SEQ ID NO: 10 is CTNAGNTA, a synthetic DNA sequence, where N is a universal base;
SEQ ID NO: 11 is CTANNTTA, a synthetic DNA sequence, where N is a universal base; and
SEQ ID NO: 12 is CGCCAGGGTTTTCCCAGTCAC-GACGTTGTAAAACGACGGCCAGTGAATCC GTAAT-CATGGCCAT, a synthetic DNA sequence.

DETAILED DESCRIPTION

The present invention relates to systems and methods for sequencing nucleic acids, including sequencing nucleic acids in fluidic droplets. In one set of embodiments, the method employs sequencing by hybridization using droplets such as microfluidic droplets. In some embodiments, droplets are formed which include a target nucleic acid, a nucleic acid probe, and at least one identification element, such as a fluorescent particle. The nucleic acid probes that hybridize to the target nucleic acid are determined, in some instances, by determining the at least one identification element. The nucleic acid probes that hybridize to the target nucleic acid may be used to determine the sequence of the target nucleic acid. In certain instances, the microfluidic droplets are provided with reagents that modify the nucleic acid probe. In some cases, a droplet, such as those described above, is deformed such that the components of the droplets individually pass a target area.

In one aspect, the present invention relates to systems and methods for sequencing a target nucleic acid. In various embodiments, a target nucleic acid may be replicated and contained within a plurality of fluidic droplets, which may also contain nucleic acid probes, identification elements, or the like. As is discussed in detail below, by determining the nucleic acid probes within the fluidic droplets, the sequence of the target nucleic acid may be determined. In one embodiment, the present invention relates to a method of providing a microfluidic droplet which comprises a nucleic acid probe and at least one identification element, providing a second microfluidic droplet which comprises a target nucleic acid, and fusing the first fluidic droplet and the second fluidic droplet to form a fused fluidic droplet. In some cases, the method further comprises determining whether the nucleic acid probe is associated with the target nucleic acid, e.g., such that the nucleic acid probe and the target nucleic acid remain together in solution and form a relatively stable duplex, for instance through non-covalent interactions such as hydrogen bonding, base pairing, etc., and do not readily separate while in solution. In some instances, the nucleic acid probe may hybridize to the target nucleic acid. Additionally, in some cases, the identity of the at least one identification element may be determined.

As a non-limiting example, a first embodiment is shown in FIG. 1. In this FIG., a first fluidic droplet 10 is provided, containing a nucleic acid probe 11 and at least one identification element 12. Additionally, in this example, a second fluidic droplet 13 is provided, which contains a target nucleic acid 14. The first fluidic droplet is fused with the second fluidic droplet to form a fused fluidic droplet 15, as indicated by arrow 100. In some cases, nucleic acid probe 11 may become associated with target nucleic acid 14, as indicated by arrow 101, and the association of the target nucleic acid and the nucleic acid probe may be determined, as shown by arrow 102. For instance, the nucleic acid probe and the target nucleic acid may become associated 16 due to complementary or substantially complementary sequences. In some cases, a sequence of the nucleic acid probe may be determined to determine the sequence of at least a portion of the target nucleic acid by determining the at least one identification element 12 (shown by arrows 103 and 104), as is discussed in detail below.

In some cases, a collection of droplets is used, in which the droplets may contain distinguishable nucleic acid probes and/or identification elements. By determining association of the target nucleic acid with the distinguishable nucleic acid probes, e.g., by using the identification elements, the sequence of the target nucleic acid may be determined. Typically, not all of the target nucleic acid contained in each of the fluidic droplets will associate with all of the nucleic acid probes, and by determining which nucleic acid probes are able to associate with the target nucleic acid, the sequence of the target nucleic acid may be determined. Methods for preparing a collection of droplets is discussed in more detail below.

As mentioned, various embodiments of the invention are directed towards containing nucleic acids and/or other species within fluidic droplets. As used herein, a "fluid" is given its ordinary meaning, i.e., a substance that tends to flow and to conform to the outline of its container. Typically, fluids are materials that are unable to withstand a static shear stress, and when a shear stress is applied, the fluid experiences a continuing and permanent distortion. Thus, the fluid may have, in some cases, any suitable viscosity that permits at least some flow of the fluid. Non-limiting examples of fluids include liquids and gases, but may also include free-flowing solid particles, viscoelastic fluids, and the like.

A "droplet," as used herein, is an isolated portion of a first fluid that is completely surrounded by a second fluid. It is to be noted that a droplet is not necessarily spherical, but may assume other shapes as well, for example, depending on the external environment. In one embodiment, the droplet has a minimum cross-sectional dimension that is substantially equal to the largest dimension of the channel perpendicular to fluid flow in which the droplet is located. The diameter of a droplet, in a non-spherical droplet, is the diameter of a perfect mathematical sphere having the same volume as the non-spherical droplet.

The fluidic droplets may be formed using any suitable technique. For example, the droplets may be formed by shaking or stirring a liquid to form individual droplets, creating a suspension or an emulsion containing individual droplets, or forming the droplets through pipetting techniques, needles, or the like. Other non-limiting examples of the creation of droplets are disclosed in U.S. patent application Ser. No. 11/024,228, filed Dec. 28, 2004, entitled "Method and Apparatus for Fluid Dispersion," by Stone, et al., published as U.S. Patent Application Publication No. 2005/0172476 on Aug. 11, 2005; U.S. patent application Ser. No. 11/246,911, filed Oct. 7, 2005, entitled "Formation and Control of Fluidic Species," by Link, et al., published as U.S. Patent Application Publication No. 2006/0163385 on Jul. 27, 2006; or U.S. patent application Ser. No. 11/360,845, filed Feb. 23, 2006, entitled "Electronic Control of Fluidic Species," by Link, et al., published as U.S. Patent Application Publication No. 2007/0003442 on Jan. 4, 2007, International Patent Application No. PCT/US2008/007941, filed Jun. 26, 2008, entitled "Methods and Apparatus for Manipulation of Fluidic Species," each incorporated herein by reference.

Various embodiments of the invention use a plurality or series of fluidic droplets. The fluidic droplets may be polydisperse (e.g., having a range of different sizes), or in some cases, the fluidic droplets may be monodisperse or substantially monodisperse, e.g., having a homogenous distribution of diameters, for instance, such that no more than about 10%, about 5%, about 3%, about 1%, about 0.03%, or about 0.01% of the droplets have an average diameter greater than about 10%, about 5%, about 3%, about 1%, about 0.03%, or about 0.01% of the average diameter. The "average diameter" of a population of droplets, as used herein, is the arithmetic average of the diameters of the droplets. Those of ordinary skill in the art will be able to determine the average diameter of a population of droplets, for example, using laser light scattering or other known techniques. As non-limiting examples, the average diameter of a droplet may be less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers. The average diameter of the droplet may also be at least about 1 micrometer, at least about 2 micrometers, at least about 3 micrometers, at least about 5 micrometers, at least about 10 micrometers, at least about 15 micrometers, or at least about 20 micrometers in certain cases.

A fluidic droplet may contain a target nucleic acid to be sequenced, and the target nucleic acid may be any suitable nucleic acid. For example, the target nucleic acid may be a nucleic acid that encodes a biological entity, such as a protein, an enzyme, an antibody, a receptor, a ribozyme, a ribosome, or the like, and/or a portion thereof. As another example, the target nucleic acid may be a regulatory sequence or a non-coding sequence, for instance, a small interfering RNA, a microRNA, a small hairpin RNA, or the like. The target nucleic acid can be any number of nucleotides in length, for example, on the order of about 25, about 50, about 60, about 64, about 70, about 80, about 90, about 100, about 200, about 400, about 800, about 1600, about 3200, about 6400, or even more nucleotides in length. Non-limiting examples of target nucleic acids (and other types of nucleic acids, as are described herein) include ribonucleic acid (RNA), deoxyribonucleic acid (DNA), or mixtures or copolymers thereof, which may be isolated from natural sources, recombinantly produced, artificially synthesized, etc. The nucleic acid may contain residues such as adenosine or "A," thymidine or "T," guanosine or "G," cytidine or "C," or uridine or "U," or other residues, such as the universal residues discussed in detail below. The nucleic acid can be double-stranded or single stranded to facilitate hybridization. Moreover, the nucleic acid can be obtained from virtually any source. For instance, the nucleic acid may be isolated from a cell or a virus, synthesized using traditional chemical synthesis, synthesized using polymerase chain reaction (PCR) technology, or the like.

The target nucleic acid contained within the droplet may then be exposed to a nucleic acid probe and/or one or more identification elements. For instance, as previously discussed, a fluidic droplet containing the target nucleic acid may be fused with a second fluidic droplet containing a nucleic acid probe and at least one identification element. Various techniques for fusing droplets together are discussed in more detail below.

Nucleic acid probes are generally used, in certain embodiments, to determine certain sequences within the target nucleic acid. Often, short portions of the target nucleic acid can be associated with the nucleic acid probe, for instance, a sequence of less than about 20 residues, less than about 15 residues, less than about 10 residues, less than 9 residues, less than 8 residues, less than 7 residues, less than 6 residues, less than 5 residues, less than 4 residues, etc. The residues are typically contiguous within the target nucleic acid probe although, in some cases as discussed below, some of the residues within the target nucleic acid are not necessarily contiguous. In some embodiments, a nucleic acid probe may contain a relatively short sequence of nucleic acid residues that is able to recognize at least a portion of the target nucleic acid, and often has a similar length as the recognized portion of the target nucleic acid. For instance, the nucleic acid probe may have a sequence having length of less than about 20 nucleotides or less than about 10 nucleotides in some cases, or a length such as those described above. In one case, the length of the nucleic acid probe sequence may be four residues (e.g., FIG. 2A). In another case, the length may be five residues (e.g., FIG. 2B). In yet another case, the length may be six residues (e.g., FIG. 2C). The nucleic acid probe sequences within the nucleic acid probe may be contiguous, or the sequence may be non-contiguous. For instance, there may be universal residues or gaps present. In some instances, the nucleic acid probe may be labeled in some manner, such as with a signaling entity, for instance, a radioisotope or with a fluorescence tag (e.g., FIG. 2D). Various signaling entities and other examples of nucleic acid probes will be discussed in more detail below.

The nucleic acid probe may be selected such that at least some of the probes will contain sequences complementary or substantially complementary to the target nucleic acid sequence. For instance, in one embodiment, the nucleic acid probe sequences are selected such that every permutation of nucleic acid residues of a certain size or number (or range of sizes or numbers) is represented, thereby ensuring that at least one of those nucleic acid probe sequences is substantially complementary to the target nucleic acid. As used herein, a first sequence that is "substantially complementary" to a second sequence is one which at least about 75% of the first and second sequences are complementary (e.g., through Watson-Crick complementarity pairing, or optionally also including G:U wobble) and/or the sequences have a maximum of 1 or 2 base mismatches. In some embodiments, the two sequences may be at least about 80%, at least about 85%, at least about 90%, at least about 95%, at least about 97%, at least about 98%, at least about 99%, or at least about 100% complementary).

In some embodiments, a plurality of distinguishable or non-identical nucleic acid probes is used, for example, nucleic acid probes having one or more differences in the sequence of residues contained within the nucleic acid probes. For instance, a plurality of fluidic droplets may be used, and the fluidic droplets may each contain a specific nucleic acid probe sequence. The fluidic droplets may be prepared such that each fluidic droplet contains only one nucleic acid probe sequence (although multiple copies of the nucleic acid probe may be present). In addition, in some cases, different fluidic droplets may independently contain the same or different nucleic acid probe sequence (e.g., such that there is some redundancy so that not each fluidic droplet in a given population or collection of droplets is necessarily unique).

In some cases, the nucleic acid probe can be labeled, e.g., with a signaling entity. The signaling entity may be determined in some fashion using a detection method, such as those discussed below. The signaling entity may be included within the nucleic acid probe at any suitable location, for example, at a 5' terminal site of the nucleic acid sequence of the nucleic acid probe, a 3' terminal site, or at an internal site within the nucleic acid probe. In some cases, the signaling entity can be chosen such that it produces a different signal (or does not produce a signal) when the nucleic acid probe is associated with a target nucleic acid compared to when the nucleic acid probe is not associated with the target nucleic acid. The signaling entity can include, but is not limited to, a fluorescent dye, a chemiluminescent entity, a radioactive label, an isotope such as a non-radioactive isotope or an isotope detectable by mass spectrometry (e.g., an electrophore mass label (EML)), a ligand which can serve as a specific binding partner to a labeled antibody, an enzyme, an antibody which can serve as a specific binding partner for a labeled ligand, an antigen, a group having a specific reactivity, and/or an electrochemically detectable moieties. Non-limiting examples of fluorescent signaling entities include fluorescein, rhodamine, or hexachlorofluorescein; those of ordinary skill in the art will be aware of other fluorescent entities that are readily commercially available. Yet other examples of signaling entities are discussed in detail herein.

For instance, in one embodiment, a nucleic acid probe can include a sequence of nucleic acid residues, a signaling entity, and a quencher or an enhancer (e.g., as is shown in FIG. 2E, with the signaling probe labeled S and a quencher labeled Q). The signaling entity may be, e.g., a fluorescent entity, and may be located anywhere in the nucleic acid probe, for instance, covalently attached to the 5' end of the nucleic acid sequence. Non-limiting examples of fluorescent entities potentially suitable for use in the nucleic acid probe in various embodiments include 6-carboxyfluorescein and tetrachlorofluorescin. The quencher or enhancer may be any entity able to affect the signaling entity in some fashion, e.g., by respectively inhibiting or facilitating determination of the signaling entity. For instance, the proximity of a fluorescent signaling entity and a quencher within a nucleic acid probe may be such that the quencher is able to partially or completely inhibit fluorescence of the signaling entity, while an enhancer may be able to enhance the fluorescence of a fluorescent signaling entity when the enhancer is positioned proximate the signaling entity. The quencher or enhancer may also be located anywhere in the nucleic acid probe, for example, attached to the 3' end of the nucleic acid sequence. Non-limiting examples of quenchers include tetramethylrhodamine and dihydrocyclopyrroloindole tripeptide.

As a non-limiting example, a quencher (or similarly, an enhancer) can be used within a signaling entity in a nucleic acid probe as follows. A nucleic acid probe associated with a target nucleic acid may be removed or dissociated from the target nucleic acid by the action of certain enzymes or other species, for instance, polymerases such as Taq polymerases. For instance, in some cases, a polymerase may cause degradation of the nucleic acid sequence within the nucleic acid probe to occur, which may cause release of the signaling entity and/or the quencher or enchancer and hence, the quencher or enchancer may no longer be proximate to or at least substantially affect the signaling entity. Thus, degradation of the nucleic acid probe can be determined by determining a change in the signaling entity. In contrast, in systems where the nucleic acid probe does not sufficiently associate with the target nucleic acid (e.g., if no sufficiently complementary sequences are present), no degradation of the nucleic acid probe would occur through action of the polymerase or other species (e.g., any association that exists between the target nucleic acid and the nucleic acid probe is too transient or short for enzymatic action to occur), and thus, no significant change in the signal of the signaling entity could be determined. Accordingly, in one embodiment, a polymerase such as Taq polymerase may be provided to a fluidic droplet comprising a nucleic acid probe and a target nucleic acid. The polymerase may be provided to the fluidic droplet using any suitable technique, as discussed herein.

In some cases, a nucleic acid probe may comprise at least one locked nucleic acid (LNA) residue (see, e.g., FIG. 2F). A locked nucleic acid residue is a nucleic acid analog that has a chemical shape similar to a naturally occurring nucleic acid residue (e.g., being able to form 2 or 3 hydrogen bonds with a complementary residue), but is not free to rotate in as many dimensions as a naturally occurring nucleic acid residue. For instance, in some cases, a locked nucleic acid residue may contain a 2'-O, 4'-C methylene bridge, where the methylene bridge "locks" the ribose in the 3'-endo structural conformation, which is often found in the certain form of DNA or RNA. The locked ribose conformation may enhance residue stacking and/or backbone pre-organization. This can significantly increase the thermal stability (e.g., melting temperature) of the nucleic acid sequence in some cases. As discussed in detail below, a nucleic acid probe containing one or more locked nucleic acid residues may be useful in certain embodiments because the locked nucleic acid residue may exhibit increased affinity for association with the target nucleic acid, e.g., due to the restrictions on its ability to internally rotate.

In certain embodiments, the nucleic acid probe may contain a universal residue, which may be able to engage in a residue-pairing relationship with more than one natural nucleotide, and in some cases, with all of the natural nucleotides. Exemplary universal residues include 5-nitroindole and 3-nitropyrrole, although other universal residues useful for the systems and methods described herein will be known to those of skill in the art. As discussed below, a nucleic acid probe containing one or more universal bases may be useful in certain embodiments. The nucleic acid probes may be synthesized using any suitable technique, e.g., solid phase phosphoramidite triester methods. In some cases, a plurality of nucleic acid probes is synthesized, forming a library of such probes. The library may include a plurality of sequences, for example, organized in a plurality of fluidic droplets. In some (but not all) embodiments, the library may contain sequences that have roughly the same number of residues, for example, around 4 residues, around 5 residues, around 6 residues, around 7 residues, etc. The library of nucleic acid probes may be prepared using any suitable technique, and may be produced using manual techniques or automated, e.g., using a robotic apparatus.

In one embodiment, the nucleic acid probes can be produced in parallel. For instance, a microfluidic device may be used to allow for parallel creation of a library of nucleic acid probes. For instance, a microfluidic drop maker may be replicated many times on a single chip, and each drop maker may be used to prepare a different nucleic acid probe. Non-limiting examples of techniques of producing droplets of fluid surrounded by a liquid are described in U.S. patent application Ser. No. 11/024,228, filed Dec. 28, 2004, entitled "Method and Apparatus for Fluid Dispersion," published as U.S. Patent Application Publication No. 2005/0172476 on Aug. 11, 2005; U.S. patent application Ser. No. 11/360,845, filed Feb. 23, 2006, entitled "Electronic Control of Fluidic Species," published as U.S. Patent Application Publication No. 2007/000342 on Jan. 4, 2007; or U.S. patent application Ser. No. 11/368,263, filed Mar. 3, 2006, entitled "Systems and Methods of Forming Particles," published as U.S. Patent Application Publication No. 2007/0054119 on Mar. 8, 2007, each incorporated herein by reference. For example, in some embodiments, an electric charge may be created on a fluid surrounded by a liquid, which may cause the fluid to separate into individual droplets within the liquid.

In one embodiment, the library may comprise every possible sequence for a set of nucleic acid sequences having a certain length or lengths. In another embodiment, the library may comprise at least about 30%, at least about 50%, at least about 80%, at least about 85%, at least about 90%, at least about 95%, or at least about 100% of all possible sequences having a certain length or lengths. Some techniques for preparing a library are discussed below.

In many embodiments, at least one identification element is present. An "identification element" as used herein, is a species that includes a component that can be determined in some fashion, e.g., the identification element may be identified when contained within a droplet. The identification elements may be insoluble (e.g., suspended) or soluble within the droplet. Non-limiting examples include identification elements detectable by fluorescence, chemiluminescence, radioactivity, or the like. Specific examples include, but are not limited to, particles containing dyes, quantum dots, or fluorescent particles which, in some embodiments, may also have other species attached thereto, for instance, oligonucleotides such as those described herein. In some cases, more than one identical identification element may be present within any given droplet.

In certain embodiments, more than one non-identical identification element may be used, e.g., within a droplet. For instance, a droplet may contain at least two distinguishable identification elements, at least three distinguishable identification elements, at least four distinguishable identification elements, at least five distinguishable identification elements, etc. Identification elements may be distinguished using any suitable method, e.g., color, fluorescence, absorption, intensity, size, charge, radioactivity, mass, or the like.

In one set of embodiments, particles or microparticles (e.g., beads) may be used as identification elements. The particles may have any dimension, and may be spherical or non-spherical. For instance, the particles may have average diameters ranging from approximately about 100 nm to about 100 um in diameter in some cases. In certain embodiments, the particles may have an average diameter of less than about 1 micrometer, less than about 300 nm, less than about 100 nm, less than about 30 nm, or less than about 10 nm. The average diameter, as used herein, is the arithmetic average of the diameters of the particles contained within the droplets. The diameters of a non-spherical particle, as used herein, is the diameter of a perfect mathematical sphere having the same volume as the particle.

In some embodiments, a plurality of identification elements may be chosen to identify droplets such that there are at least 3 distinguishable identification elements, at least 4 distinguishable identification elements, at least 6 distinguishable identification elements, at least 8 distinguishable identification elements, at least 9 distinguishable identification elements, at least about 10 distinguishable identification elements, at least about 20 distinguishable identification elements, at least about 30 distinguishable identification elements, at least about 40 distinguishable identification elements, at least about 50 distinguishable identification elements, at least about 60 distinguishable identification elements, at least about 70 distinguishable identification elements, at least about 80 distinguishable identification elements, at least about 90 distinguishable identification elements, at least about 100 distinguishable identification elements, etc. One non-limiting example of a plurality of distinguishable identification elements are the Luminex® FlexMAP Microspheres beads commercially available from Luminex® Corp. Beads or particles such as these may be distinguished, according to one embodiment, by the use of two or more dyes or other compounds that can be independently varied within each bead or particle. Therefore, a plurality of distinguishable beads may be used as a plurality of identification elements, according to certain embodiments. As another, specific non-limiting example, particles comprising polystyrene and one or more dyes may be used as identification elements. The dyes employed within the particles may include, for instance, squaric acid-based molecules or other fluorescent molecules that exhibit fluorescence, e.g., extending into near infrared and/or infrared region. In some cases, two or more dyes with concentrations that can be independently controlled can be used within each particle.

In one aspect, a target nucleic acid may be exposed to a nucleic acid probe and at least one identification element. For instance, the nucleic acid probe and the at least one identification element may be contained within a first fluidic droplet, and the target nucleic acid may be contained within a second fluidic droplet, which are then fused together (e.g., as discussed below), thereby exposing the target nucleic acid to the nucleic acid probe. By determining association of the target nucleic acid probe and the nucleic acid probe, the sequence of at least a portion of the target nucleic acid probe may be determined. In some cases, by repeating this with a plurality of different nucleic acid probes, the sequence of the entire target nucleic acid probe may be determined.

One set of embodiments for sequencing a target nucleic acid is generally described as follows. A first fluidic droplet is provided that includes a nucleic acid probe and at least one identification element. In this example, the nucleic acid probe comprises a sequence of nucleic acid residues attached to a signaling entity and a quencher or enhancer. For instance, the nucleic acid probe may contain 4, 5, 6, 7, 8, or 9 residues. Signaling entities, quenchers, and enhancers were discussed above. A second fluidic droplet is also provided which includes a target nucleic acid. The first fluidic droplet and the second fluidic droplet may be fused according to any suitable method, including the ones discussed herein. The fused fluidic droplet also can comprise a polymerase. The polymerase may be incorporated in the fused fluidic droplet by providing the polymerase to the first fluidic droplet or the second fluidic droplet before the droplets are fused, or directly to the third fluidic droplet after the first and second droplet were fused. In certain cases, e.g., where the respective sequences of the nucleic acid probe and the target nucleic acid are complementary or substantially complementary, the nucleic acid probe may hybridize to or otherwise associate with the target nucleic acid after fusion of the first and second droplets. In these cases, as discussed above when using a nucleic acid probe that comprises a signaling entity and a quencher or enhancer, the polymerase may cause degradation of the nucleic acid probe to occur when the nucleic acid probe hybridizes or associates with the target nucleic acid. The signaling entity and/or the quencher or enchancer may then be released from the nucleic acid probe due to action of the polymerase, and hence, the quencher or enchancer may no longer substantially affect the signaling entity, which can be determined. However, if the nucleic acid probe does not hybridize or otherwise associate with the target nucleic acid, e.g., due to a lack of sufficient complementarity, then no change in the signaling entity may be determined after fusion of the first and second droplets. Thus, the determination of a change in the signaling entity may be used to determine whether the nucleic acid probe hybridized to or otherwise associated with the target nucleic acid. The at least one identification element may also be determined and/or be employed in the determination of the sequence of the nucleic acid probe.

Figure 3:
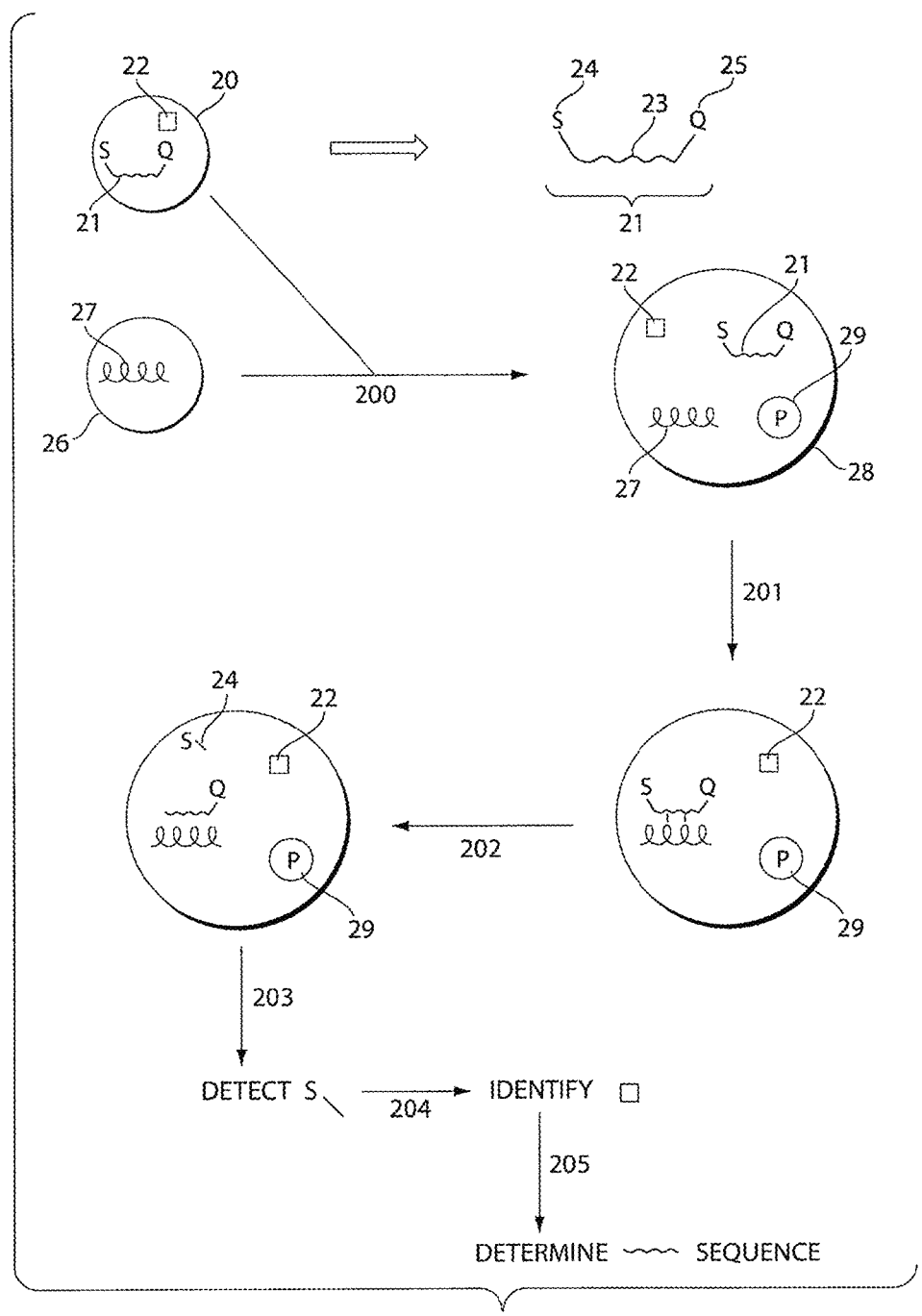
FIG. 3 shows a method for sequencing a target nucleic acid in another embodiment of the invention.

A non-limiting example is shown in FIG. 3. In this figure, a first fluidic droplet 20 is shown containing a nucleic acid probe 21 and at least one identification element 22. In other embodiments, however, two, three, or four or more identification elements may be used within the droplet. Nucleic acid probe 21, in this figure, includes a nucleic acid sequence 23 attached to a signaling entity 24 and a quencher ("Q") 25 (although in other embodiments, an enhancer may be used instead of a quencher). Additionally, a second microfluidic droplet 26 is provided which contains a target nucleic acid 27. In this example, first fluidic droplet 20 is fused with second fluidic droplet 26 to form a fused fluidic droplet 28, as indicated by arrow 200. A polymerase 29 is present within the fused fluidic droplet (for example, that was present in the first and/or second fluidic droplets). If nucleic acid probe 21 associates with target nucleic acid 27, as indicated by arrow 201, signaling entity 24 is displaced from nucleic acid 23 and quencher 25, as indicated by arrow 202. In certain instances, nucleic acid probe 21 and target nucleic acid 27 may associate (e.g., if the nucleic acid probe and the target nucleic acid are complementary or substantially complementary), and their association can be detected by determining a change in signaling entity 24, as indicated by arrow 203. In some cases, the sequence of nucleic acid 23 may then be determined by determining identification element 22 (shown by arrows 204 and 205)

Another set of embodiments for sequencing a target nucleic acid uses ligases to join nucleic acid probes together in the presence of a target nucleic acid. An example is as follows. A first fluidic droplet may be provided that comprises at least a first and a second nucleic acid probe selected from a first group and a second group of nucleic acid probes, respectively. In some cases, however, two fluidic droplet may be provided, either comprising the first or the second nucleic acid probe selected from the first or the second group of nucleic acid probes, respectively. The nucleic acid probes each comprise a sequence of nucleic acid residues attached to a signaling entity, a quencher and/or an enhancer, as discussed more herein. A second fluidic droplet is also provided which comprises a target nucleic acid. The first fluidic droplet (or two separate fluidic droplets) and the second fluidic droplet can then be fused using any suitable method, as discussed herein.

In addition, a ligase can be incorporated in the fused fluidic droplet. The ligase can be incorporated in the fused fluidic droplet by providing the ligase to the first fluidic droplet or the second fluidic droplet before the droplets are fused, or directly to the fused fluidic droplet after the first and second droplet were fused.

In some embodiments, the first and the second nucleic acid probes can associate with the target nucleic acid, e.g., if the target nucleic acid and the nucleic acid probes have substantial complementarity. In these instances, the nucleic acid probes may be joined together (e.g., via ligation with the ligase), which can be used (as discussed below) to determine the association with the nucleic acid probe. For instance, in some cases, the first nucleic acid probe and the second nucleic acid probe will associate (e.g., hybridize) with the target nucleic acid in positions adjacent to each other (e.g., the sequence of the first nucleic acid is substantially complimentary with the target nucleic acid and the sequence of the second nucleic acid is substantially complimentary with the target nucleic acid adjacent to the sequence which is substantially complimentary with the first nucleic acid probe). In such cases, ligation of the first and the second nucleic acid probes can occur due to the presence of the ligase. However, in other instances where the first and the second nucleic acid probes do not associate in positions adjacent on the target nucleic acid, no ligation can occur. As an example, the first and the second nucleic acid may have sequences which are substantially complimentary with the target nucleic acid but the sequences are not adjacent to each other (e.g., one or more residues may be present in the target nucleic acid probe between the sequence complimentary to the first and the second nucleic acid probes).

In some embodiments, it may be advantageous to use ligation methods such as describe above for sequencing a target nucleic acid. For example, as described more herein, such methods may allow the formation of relatively large sequencing libraries from smaller libraries. This can reduce and time to and/or cost of the (e.g., cost of reagents) synthesis of the library. In addition, the ligation method can comprise enhanced signals, in some embodiments, as compare to non-ligation methods, since ligation increases probe length, which in turn can increase the binding energy. In some cases, such methods may increases single base pair specificity, thereby increasing the accuracy of the sequencing process. This is because shorter nucleic acid probes may have higher single-base pair specificity as compared to a longer nucleic acid probes. Specificity and binding energy may also be enhanced in some cases by using nucleic acid probes comprising universal bases, locked-nucleic acids, gaps, or other biochemical reagents to engineer probe structure and optimize the process, e.g., as discussed herein. The ligation method may also advantageously combine the benefits of using a library comprising of both long and short nucleic acid probes in some cases. For example, short probes may be used to form longer probes, which generally will be more tightly bound to the nucleic acid probe. On the other hand, longer probes are generally less specific than shorter nucleic acid probes due to flexibility of the probe. Therefore, certain ligation methods may take advantage of some of the benefits of shorter and longer probes (e.g., specific binding of shorter probes, but once bound, the shorter probes are ligated to form a longer probe, therefore the binding is tighter).

A non-limiting example of a ligation method of the present invention is illustrated in FIG. 16. As shown in FIG. 16A, target nucleic acid 80 is exposed to a first nucleic acid probe 82 and a second nucleic acid probe 84. In some cases, the first and second nucleic acid probes may hybridize with the target nucleic acid adjacent to each other as shown in FIG. 16B, and as indicated by arrow 81. Target nucleic acid 80 comprising the first 82 and second 84 nucleic acid probes may then be exposed to ligase 86, as indicated by arrow 83. As shown in FIG. 16C, the first and the second nucleic acid probes may be ligated to form a nucleic acid oligomer 88. In some cases, however, the first and the second nucleic acid probes do not hybridize adjacent to each other on the target nucleic acid, as shown in FIG. 16E and indicated by arrow 87. In such instances, upon exposure of the target nucleic acid 80 comprising the first 82 and second 84 nucleic acid probes to ligase 86, as indicated by arrow 89, no substantial ligation of the nucleic acid probes will occur. In some cases, one or both of the nucleic acid probes will not hybridize to the target nucleic acid (e.g., the sequence is not substantially complimentary), and no ligation will occur between the first nucleic acid probe and the second nucleic acid probe. As an example, as shown in FIG. 16D and as indicated by arrow 85, only first nucleic acid probe 82 hybridizes with target nucleic acid 80 while second nucleic acid probe 84 does not hybridize with target nucleic acid 80.

Figure 36A:
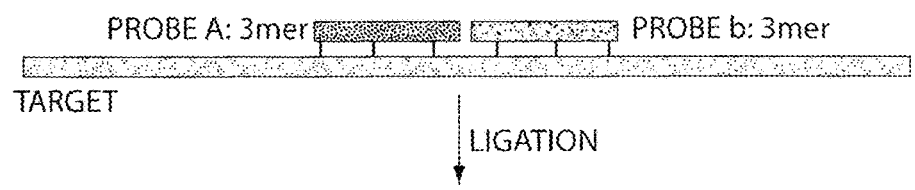
FIG. 36A illustrates the hybridization of two 3-mer nucleic acid probes to a target nucleic acid, according to one embodiment.
Figure 36B:
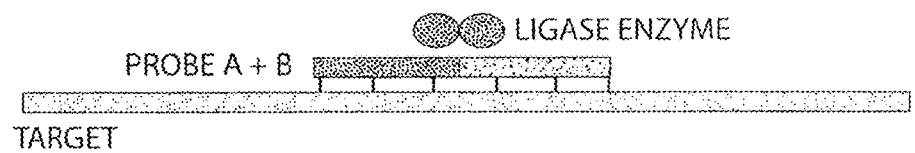
FIG. 36B illustrates ligation of the two 3-mer nucleic acid probes shown in FIG. 36A.

As another non-limiting example, if two 3-mers nucleic acid probes are complimentary, hybridize adjacently, and in the correct order, they may be ligated, forming a new 6-mer, as illustrated in FIGS. 36A and 36B. FIG. 36A shows hybridization of contiguous complimentary 3-mers to a target nucleic acid. FIG. 36B shows the ligation of nucleic acid probes with a ligase. Ligation covalently bonds together the two 3-mer probes forming a more tightly bound 6-mer. Before ligation, the binding energies of the probes are merely that of the 3-mers, which is generally too small to be detected at room temperature. After ligation, the two 3-mers become a 6-mer, which has twice the binding energy of the 3-mers, and thus can hybridize, as shown in FIG. 53C. Ligation of the probes thus relies on the highly specific but transient binding of the short probes to produce a tightly bound combined probe.

The ligation of the first and the second nucleic acid probes may be determined, for example, by a change in a signaling entity associated with at least one of the nucleic acid probes. If the first and the second nucleic acid probes are complementary or substantially complementary in adjacent positions to the target nucleic acid, then the first and the second nucleic acid probes (including a signaling entity) associates with the target nucleic acid and participate in a ligation reaction as discussed above. Accordingly, by determining the signaling entity of the ligated nucleic acid probes, a portion of the sequence of the target nucleic acid may be determined, based on both the sequences of the nucleic acid probes. Conversely, if the first or the second nucleic acid probes are not able to associate with the target nucleic acid sequence (e.g., if the sequences are not sufficiently complementary), then no ligation reaction can occur, and the determined signal entity will have a different signal. In some cases, each nucleic acid probe from the first group comprises a first signaling entity or identification element and each nucleic acid probe from the second group comprises a second signaling entity or identification element. The ligation of a first and a second nucleic acid probe may be determined by determining the first and/or second signaling entity and/or identification element.

In some cases, the first group of nucleic acid probes and/or the second group of nucleic acid probe may comprise at least a portion of all of the sequences of a selected length. For example, the first group of nucleic acid probes may comprise at least one of each of a portion of all probes with 3 nucleic acid residues. The first group of nucleic acid probes and the second group of nucleic acid probes may or may not be substantially similar. In some cases, the first group of nucleic acid probes comprises essentially of the same probes as the second group of nucleic acid probes. In some cases, the first group and the second group of nucleic acid probes comprises substantially all possible 3-mers. In some cases, a droplet may comprise a single probe from the first group and a single probe from the second group. In other cases, a droplet may comprise a plurality of probes of a first type from the first group and a plurality of probes of a second type from the second group.

The first group and the second group of nucleic acid probes may be substantially similar or different. For example, the first group and the second group of nucleic acids may be substantially similar if the first group and the second group comprises at least a portion of all possible 3-mers, but may differ in that they comprise differing signaling entities or the signaling entity is located at differing positions (e.g., 3'-end vs. 5'-end). The first group of distinguishable identification elements and the second group of distinguishable identification elements may be the substantially similar or different. In some embodiments, the first group and/or second group of nucleic acid probes comprises at least a portion of possible 3-mers, 4-mers, 5-mers, 6-mers, 7-mers, 8-mers, 9-mers, 10-mers, or the like.

Other nucleic acid residues may also be present in some cases, in addition to A, G, C, and T. For instance, in some cases, at least some of the nucleic acid probe may additionally comprise at least one universal residue. For example, a 3-mer comprising additional universal residues may have the sequence NNNXXX wherein N is a universal residue and each X in XXX is independently either one of A, G, C, or T (e.g., the 3-mer).

A universal base or universal residue (e.g., "N"), as used herein, refers to a base that, when incorporated into a polymeric structure in the form of a nucleobase (e.g., a nucleotide or a PNA) does not significantly discriminate between bases on a complementary polymeric structure having nucleobases. For example, a universal base can hybridize to more than one nucleotide selected from A, T, C, and G. Universal residues will be known to those or ordinary skill in the art. Non-limiting examples of universal residues include deoxyinosine, 3-nitropyrrole, 4-nitroindole, 6-nitroindole, 5-nitroindole, 6-methyl-7-azaindole, pyrrollpyrizine, imidizopyridine, isocarbostyril, propynyl-7-azaindole, propynylisocarbostyril, allenyl-7-azaindole, 8-aza-7-deaza-2'-deoxyguanosine, 8-aza-7-deaza-2'-deoxyadenosine, 2'-deoxycytidine, 2'-deoxyuridine, 2'-deoxyadenosine, 2'-deoxyguanosine, 7-deaza-2'-deoxyinosine, 2'-aza-2'-deoxyinosine, 3'-nitroazole, 4'-nitroindole, 5'-nitroindole, 6'-nitroindole, 4-nitrobenzimidazole, nitroindazole (e.g., 5'-nitroindazole), 4-aminobenzimidazole, imidazo-4,5-dicarboxamide, 3'-nitroimidazole, imidazole-4-carboxamide, 3-(4-nitroazol-1-yl)-1, 2-propanediol, and 8-aza-7-deazaadenine.

In some cases, the first group of nucleic acid probes may be capable of ligating on the 3' end and the second group of nucleic acid probes may be capable of ligating on the 5' end, such the only one end of each of the first nucleic acid probe and the second nucleic acid probe may ligate with each other. Therefore, the probes need to hybridize to the target nucleic acid in the correct order in order for ligation to occur. That is, the probes must hybridize to the target nucleic acid such that the 3' end of the first probe and the 5' end of the second probe are adjacent to each other and the probes are capable of being ligated. If the first probe and the second probe hybridized to the target nucleic acid such that the 5' end of the first probe and the 3' end of the second probe are adjacent to each other, the probes may not be capable of binding (e.g., if the 5' end of the first probe and the 3' end of the second probe comprise an entity (e.g., identification element, signaling entity, etc.) that prevents hybridization at that end).

The ligation method may allow a relatively smaller number of droplets to be initially prepared. For example, if a plurality of droplets were to be created comprising the total number of all possible hexamers, 4,096 types of droplets would have to be produced using the techniques described herein. However, if all possible hexamers were to be investigated using the ligation method described above using two groups of 3-mers, only 128 types of droplets would have to be produced (e.g., a first group of 3-mers (64) and a second group of 3-mers (64). The droplets of the first group may be fused with the droplets of the second group to form the library of droplets, each droplets comprising a droplet from the first group and a droplets from the second group.

Using SBH (sequencing by hybridization) bioinformatics, the length of target nucleic acid that can be sequenced in a single pass can be estimated to be about one quarter of the number probes in the library. For example, for a library of 3-mers for which there are 64 elements ($4^3$), a target nucleic acid of about 10-12 bases can be sequenced. As another example, for a library of 6-mers for which there are 4096 elements, a target nucleic acid of about 1000 bases can be sequenced. As yet another example, for a library of 12-mers of which there are about 17 million probes, a target nucleic acid of about 4 million bases can be sequenced. Such a large library, however, is impractically large for synthesizing with standard methods. With certain methods of the invention, however, 12-mers can be formed by ligating together two 6-mers, which require that 4096+4096=8192 probes of the 6-mer libraries be synthesized. This is 0.0005% the number of probes in the full 17 million element library. As described, the 6-mers that make the 12-mer can themselves be formed by ligating 3-mers, so that the 12-mers can be formed by ligating four 3-mers probes, requiring a total of 256 probes to be synthesized. This relationship is captured by the formula:

$$f(n)=(4^{n1}+4^{n2}\ldots)/4(^{n1+n2}\ldots), \text{ where}$$

$$n1+n2+\ldots=R,$$

where f(n) is the fraction of probes that must be synthesized compared to the full library, R is the length of the final ligated probe, and n1, n2 . . . the number of bases in the first, second . . . probes that are ligated together. In some cases, at least two, at least three, at least four, at least five, at least six, or the like, group of nucleic acid probes may be provided. The ligation methods describe herein may be expanded to incorporate more than two groups of nucleic acid probes. The total length of a probe formed by ligation may be at least 6, at least 7, at least 8, at least 9, at least 10, at least 11, at least 12, at least 13, at least 14, at least 15, at least 16, or the like, residues in length.

Figure 17A:
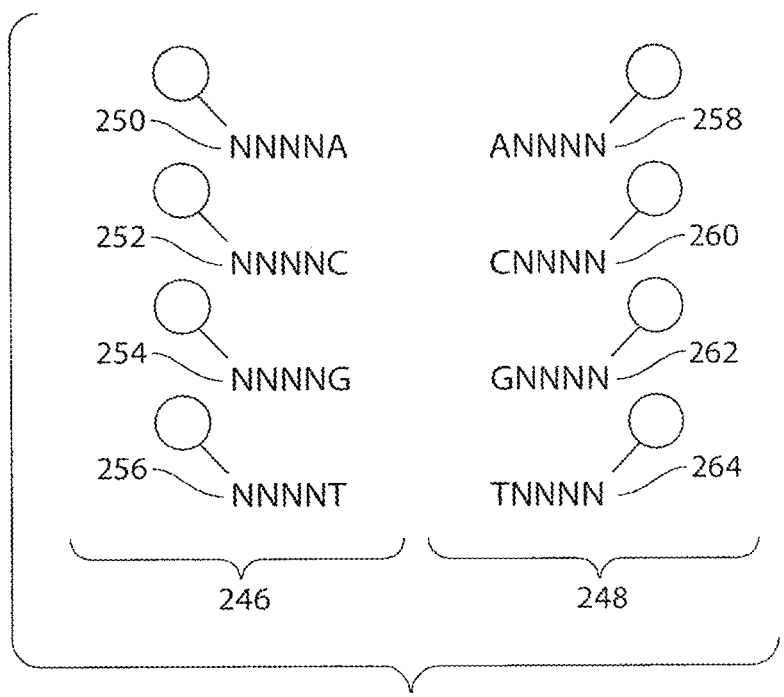
FIG. 17A depicts a first group of nucleic acid probes and a second group of nucleic acid probes that may be used in one method of the present invention, according to some embodiments.
Figure 17B:
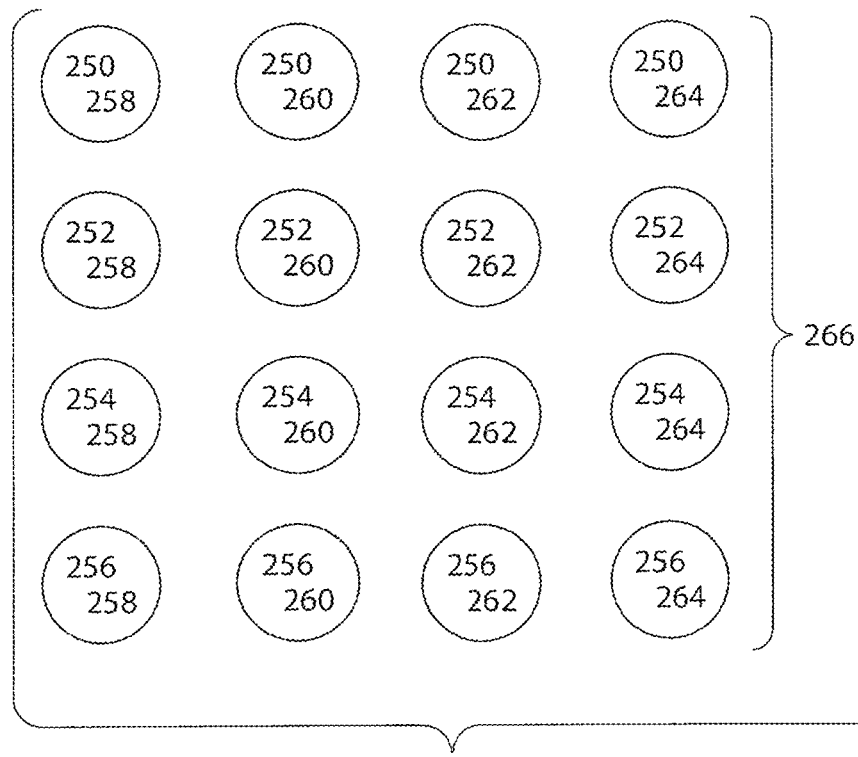
FIG. 17B depicts a plurality of droplets that may be formed by combining a first nucleic acid probe from the first group of nucleic acid probes and a second nucleic acid probe from the second group of nucleic acid probes depicted in FIG. 17A, according to one embodiment.

A non-limiting example of the combination of a first group and a second group of nucleic acid probes is shown in FIG. 17. For simplicity, the following example is shown for a first group of nucleic acid probes 246 and a second group of nucleic acid probes 248, wherein each group of probes comprises four universal nucleic acid residues and one A, C, G, or T residue (e.g., NNNNX or 1-mers comprising four universal residues), as shown in FIG. 17A. The first group of nucleic acid probes 246 comprises four probes (250, 252, 254, 256) wherein each probe comprises a signaling entity or identification element at the 3' or 5' (as shown) side. The second group of nucleic acid probes 248 comprises four probes (258, 260, 262, 264) wherein each probe comprises a signaling entity or identification element at the 5' or 3' (as shown) side, respectively, as compared to the first group of nucleic acid probes. As shown in FIG. 17B, a plurality of droplets 266 is formed where each comprises at least one probe from the first group and at least one probe from the second group. If every probe from the first group is contained in a droplet with every probe from the second group, in this example, sixteen droplets will be formed. In some cases, however, not every probe from the first group will be combine in a droplet with every probe from the second group.

In some instances, each of a first group of nucleic acid probes may be associated with at least one distinguishable identification element and each of a second group of nucleic acid probes may be associated with at least one distinguishable identification element. For example, a first group of droplets may be formed comprising a first group of distinguishable nucleic acid probes and a first group of distinguishable identification elements and a second group may be formed comprising a second group of distinguishable nucleic acid probes and a first group of distinguishable identification elements to form a second population of fluidic droplets. The nucleic acid probes comprised in a fused droplet may then be identified by identifying the distinguishable identification elements, as discussed herein with relations to determining a nucleic acid probe. The identification elements may also be used to determine the sequence of each probe following exposure of the droplets to a target nucleic acid. The distinguishable identification elements associated with the first group of nucleic acid probes and the distinguishable identification elements associated with the second group of nucleic acid probes may or may not be distinguishable from each other. In some cases, they will be distinguishable such that every (e.g., all first and all second nucleic acid probes) will be identifiable by determining the distinguishable identification element. In some cases, each of the droplets from the first group and the second group may comprise at least distinguishable identification element such that the sequence of each probe from the first and the second groups is related to a distinguishable identification element.

The library comprising the first group of nucleic acid probes and the second group of nucleic acid probes may be created using a variety of methods. The library of droplets may be created using non-microfluidic or microfluidic methods, as described herein. In general, ligation of a first and a second nucleic acid probe does not occur until after they have been exposed to the target nucleic acid.

Figure 30:
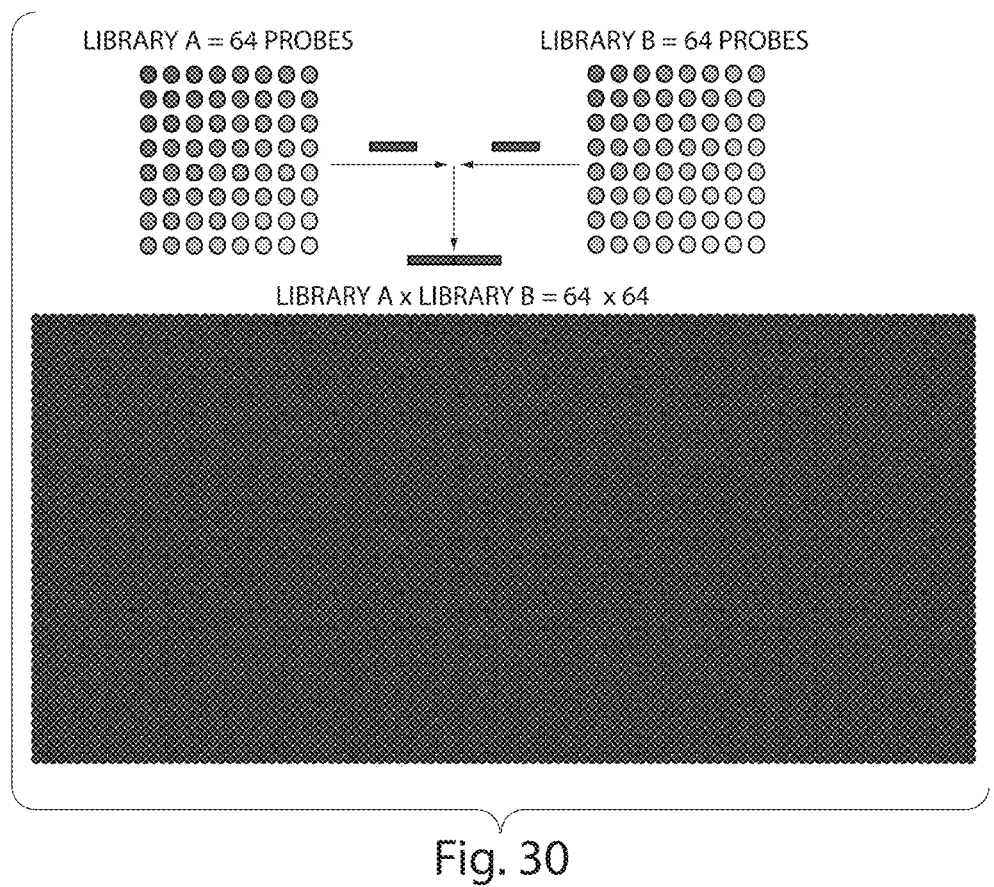
FIG. 30 shows a schematic of a library comprising a first nucleic acid probe selected from a first group of nucleic acid probes and a second nucleic acid probe selected from a second group of nucleic acid probes, according to one embodiment.
Figure 33A:
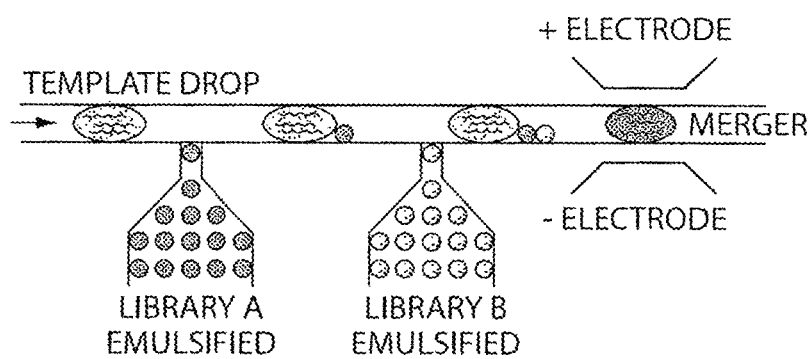
FIGS. 33A and 33B show the formation of a plurality of droplets comprising a first nucleic acid probe, a second nucleic acid probe, and a target nucleic acid, according to some embodiments of the present invention.
Figure 33B:
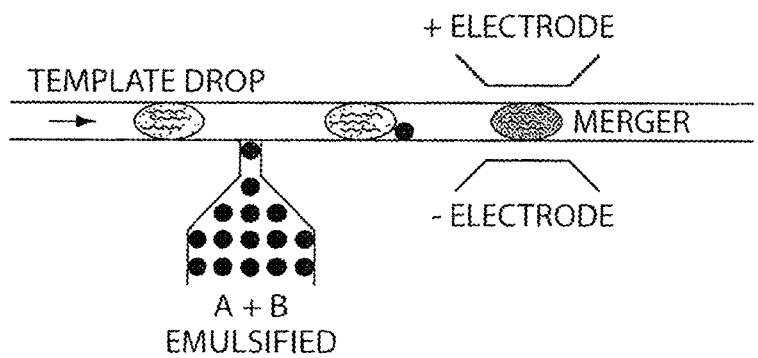

As a non-limiting example of a non-microfluidic method, each nucleic acid probe from a first and a second group of nucleic acid probes may be placed into separate containers. Each nucleic acid probe from the first group may be combined with each nucleic acid probe from the second group in separate containers until each probe from the first group has been combined with each probe from the second group. For example, FIG. 30 shows a schematic of library A and library B, each comprising the 64 probes from a first group and a second group of nucleic acid probes, respectively, comprising 3-mers. Each probe from library A is combined with each probe from library B, forming a 64×64=4096 element combined library. In some embodiments, this may be accomplished using an array. For example, a large well plate containing at least 4096 empty wells may be provided and in each well, a unique combination of the nucleic acid probes from library A and library B may be mixed together. For example, in the first column of wells probe A (1,1) is mixed with probe B (1,1), B (1,2), . . . , B (2,1), B (2,2), . . . , B(8,7), and B(8,8). In the next column, probe A (1,2) is mixed with probe B (1,1), B(1,2), . . . , B(2,1), B (2,2), . . . , B(8,7), and B (8,8), . . . and so on until every possible combination of probe A and probe B has been mixed. From these two small libraries, a total of 4096 combinations is produced (64×64=4096). Each element in the combined A×B library may be emulsified, and the emulsions may be pooled to form a pooled library comprising at least one droplet from each emulsification. The pooled library may be reinjected into a microfluidic device and merged with a target nucleic acid, as described herein, and as shown in FIG. 33B.

In some microfluidic embodiments, nucleic acid probes from a first group and a second group may be combined on a microfluidic device. For example, each nucleic acid probe from a first group may be individually emulsified and the emulsions for each probe from the first group may be combined into a first group of nucleic acid probes (e.g., library A). This may also done for a second group of nucleic acid probes to form library B. Library A and library B may be injected into a microfluidic device, as shown in FIG. 33A. In some embodiments, at the same time, droplets comprising a target nucleic acid may also be introduced into the channel, as shown on the left in FIG. 33A. Using techniques known to those of ordinary skill in the art, the flow rates of the target nucleic acid comprising droplets and the reinjected libraries may be adjusted so that one droplet comprising a target nucleic acid is combined with one droplet from library A and one droplet from library B. The three droplets may be merged using techniques described herein for merging microfluidic droplets.

As another non-limiting example, the plurality of droplets comprising a first nucleic acid probe and a second nucleic acid probe may be prepared by fusing a plurality of droplets comprising a first nucleic acid probe with one of a plurality of droplets comprising a second nucleic acid probe. That is, a first plurality of droplets may be prepared each comprising at least one of a nucleic acid probe selected from a first group of nucleic acid probes and a second plurality of droplets may be prepared each comprising at least one of a nucleic acid probe selected from a second group of nucleic acid probes. A droplet from the first plurality of droplets may be fused with a droplet from the second group of nucleic acid thereby forming a droplet comprising at least one nucleic acid probe selected form the first group of nucleic acid probes and at least one nucleic acid probe selected from the second group of nucleic acid probes. This step may be repeated until a plurality of fused droplets are formed such that substantially all of the nucleic acid probes from the first group are comprised in a droplets with substantially all of the nucleic acid probes from the second group. The library of fused droplets formed may then be fused with a third droplet comprising a target nucleic acid.

Another set of embodiments for sequencing a target nucleic acid is as follows. A first fluidic droplet can be provided that comprises a nucleic acid probe (which may contain a signaling entity) and, at least, a first identification element, a second identification element distinguishable from the first identification element, and a third identification element distinguishable from the first and the second identification elements. In some cases, a fourth identification element distinguishable from the first, second and third identification elements may also be present. Each identification element may also include, in some embodiments, an oligonucleotide, and often, a number of identification elements within a droplet may include distinguishable oligonucleotides. In some cases, each of the oligonucleotides contains one or more universal nucleic acid residues. For instance, the oligonucleotides within a given droplet may each contain a plurality of universal nucleic acid residues, and each of the oligonucleotides within the droplet may differ by a residue that is not a universal residue.

As a specific non-limiting example, when four distinguishable identification elements are present in a fluidic droplet, the oligonucleotides of the four distinguishable identification elements may be $A(N)_{n-1}$, $C(N)_{n-1}$, $G(N)_{n-1}$, and $T(N)_{n-1}$, where N is a universal nucleic acid residue and n is the length of the oligonucleotide. In this example, the oligonucleotides all differ by one residue. In some cases, the length of the universal nucleic acid portion of the oligonucleotide is four residues. In other cases, five residues. In yet other cases, six residues. In some instances, the differing residue is located at the 5' end position of the oligonucleotide, for example, 5'-$XN_{(n-1)}$-3' (X being a naturally-occurring nucleic acid residue). In other instances, however, the differing residue is located in the second position from the 5' end of the oligonucleotide, for example, 5'-$NXN_{(n-2)}$-3'. In yet other instances, the differing residue is located in other positions, for example, 5'-$NNXN_{(n-3)}$-3'.

A second fluidic droplet may be provided in this example which comprises a target nucleic acid. The fluidic droplet and the second fluidic droplet can then be fused to form a fused fluidic droplet. In some cases, there may be a nucleic acid probe present that is able to associate with the target nucleic acid, e.g., if they are complementary or substantially complementary. In addition, one of the oligonucleotides of the identification elements may also be associated with the target nucleic acid.

In some instances where the nucleic acid probe and one of the oligonucleotides of the identification elements have become associated with the target nucleic acid, the nucleic acid probe and the oligonucleotide of the identification element may be joined together (e.g., via ligation), which can be used (as discussed below) to determine the association. Ligation typically occurs when the oligonucleotide of the identification element and the sequence of the nucleic acid probe are positioned adjacent to each other with respect to the target nucleic acid, and no substantial ligation will occur if the oligonucleotide and the nucleic acid probe sequence are not positioned correctly with respect to the target nucleic acid. In some cases, the ligation of the oligonucleotide and the nucleic acid probe sequence may be caused by providing a ligase in the fused fluidic droplet using any suitable technique, for example, DNA ligase. For example, ligase may be incorporated in the fused fluidic droplet by providing the polymerase to the first fluidic droplet or the second fluidic droplet before the droplets are fused, directly to the fused fluidic droplet, etc.

The ligation of the nucleic acid probe and the oligonucleotide of the identification element may be determined, for example, by determining association of the identification element and a signaling entity of the nucleic acid probe. If the nucleic acid probe is complementary or substantially complementary to the target nucleic acid, then the nucleic acid probe (including a signaling entity) associates with the target nucleic acid, and can participate in a ligation reaction. If the distinguishable identification elements are chosen such that each of the associated oligonucleotides differs by only one position (e.g., if the other residues are universal nucleic acid residues), then only one of the distinguishable identification elements will be able to participate in the ligation reaction. Accordingly, by determining which of the distinguishable identification elements has associated with the signaling entity of the nucleic acid probe, a portion of the sequence of the target nucleic acid may be determined, based on both the sequences of the nucleic acid probe and the sequence of the oligonucleotide of the identification element. Conversely, if the nucleic acid probe is not able to associate with the target nucleic acid sequence (e.g., if the sequences are not sufficiently complementary), then no ligation reaction can occur, and none of the identification elements will be found to be associated with the signaling entity of the nucleic acid probe.

Figure 4:
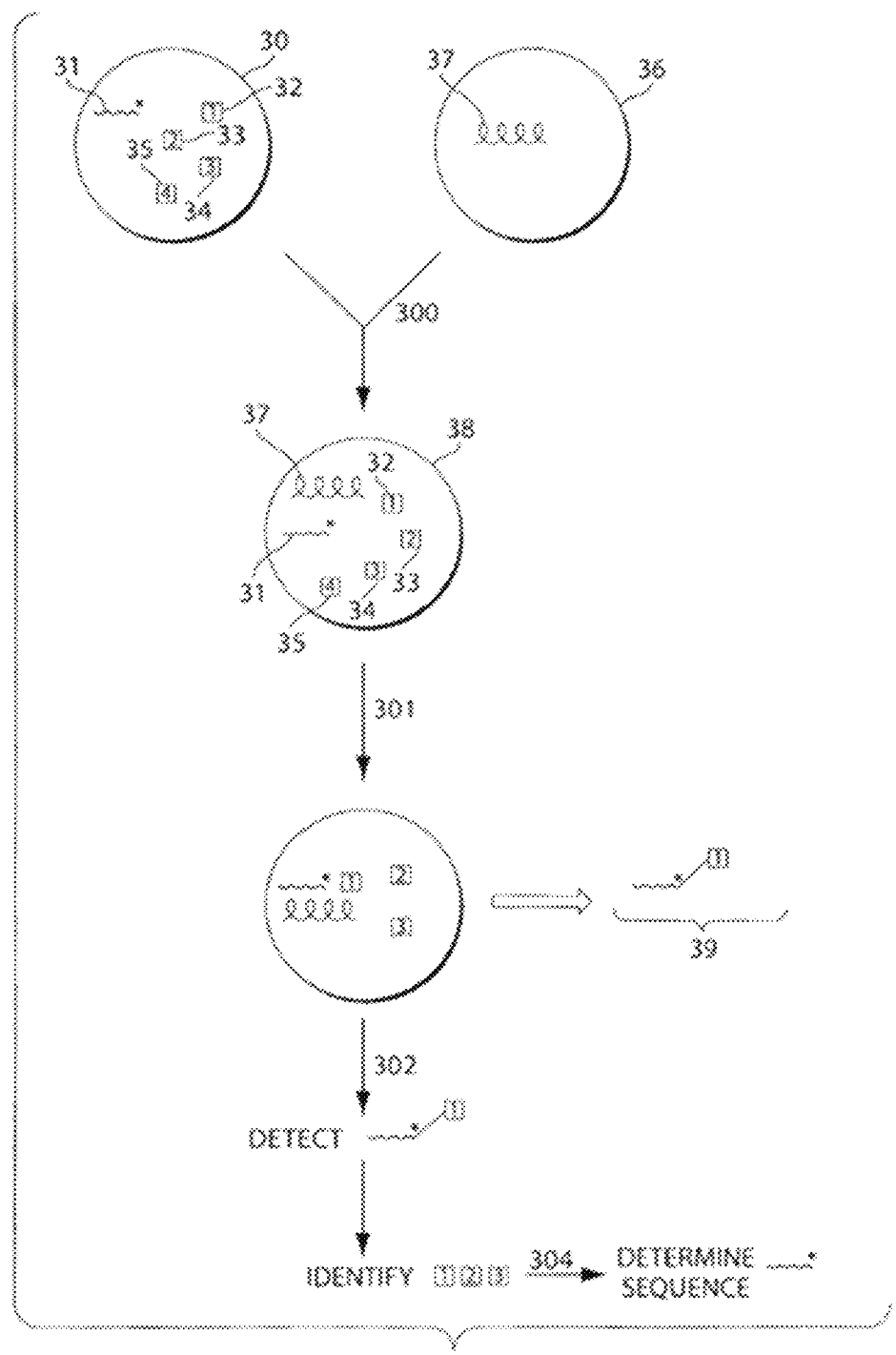
FIG. 4 shows yet another method for sequencing a target nucleic acid in another embodiment of the invention.

A non-limiting example of the above method is shown in FIG. 4. In this example, a first fluidic droplet 30 is provided which contains a nucleic acid probe 31, a first identification element 32, a second identification element 33 distinguishable from the first identification element, a third identification element 34 distinguishable from the first and second identification elements, and a fourth identification element 35 distinguishable from the first, second, and third identification elements. Of course, more than one copy of the identification elements may be present within the droplet. The distinguishable identification elements each can include an associated oligonucleotide. Each of these nucleic acid oligonucleotide sequences may be chosen to differ from the other nucleic acid oligonucleotides associated with the other identification elements by one residue, while the other residues may be universal nucleic acid residues. For instance, the four oligonucleotides associated with the four distinguishable identification elements may be NANNNN, NTNNNN, NGNNNN), and NCNNNN (or any other combination such as those described herein). In this example, a second fluidic droplet 36 is also provided comprising a target nucleic acid 37. The first fluidic droplet and second fluidic droplet are fused to form a fused fluidic droplet 38 using any suitable technique such as those described herein, as indicated by arrow 300. In some cases, nucleic acid probe 31 may become associated with the target nucleic acid 37, and one of the oligonucleotides of the identification elements (32, 33, 34, or 35) may also become associated with the target nucleic acid 37, as indicated by arrow 301. A ligase 39 is provided to the fused fluid droplet which can ligate the oligonucleotide of the identification element to the nucleic acid sequence of the nucleic acid probe if the oligonucleotide and the nucleic acid probe sequence each properly associate with target nucleic acid 37, as shown in the figure. In some cases, the ligase will not ligate if there are any gaps or interring sequences. The identification element associated with the signaling entity of the nucleic acid probe may then be determined, as shown by arrow 302. Techniques for such a determination are discussed below.

Although several particular examples of the present invention were discussed above, it should be noted that any combination of the above steps and/or additional steps, may also be used to sequence a target nucleic acid.

The sequence of a target nucleic acid may be determined by determining the association (or non-association) of the target nucleic acid to one of a plurality of distinguishable nucleic acid probes. The target nucleic acid may be associated with the nucleic acid probe when they form a relatively stable duplex by hydrogen bonding under experimental conditions. Relatively stable hydrogen bonding may be formed due to Watson-Crick complementarity (e.g., A matches T, but not G or C G matches C, but not A or T) and/or other effects such as GC wobble, or other associations caused by locked nucleic acids or universal bases, as discussed herein. Non-limiting examples of suitable methods for determining the sequence of a target nucleic acid include sequencing by hybridization techniques that are known to those of ordinary skill in the art.

Sequencing by hybridization (SBH) is a method for examining the nucleic acid residue sequence in a target nucleic acid that has been previously described, for instance, in U.S. Pat. No. 5,202,231. In general, SBH uses a set of nucleic acid probes of defined sequence to probe for complementary sequences on a longer target strand of a target nucleic acid. The defined sequences which hybridize to the target can then be aligned using computer algorithms to construct the sequence of the target nucleic acid.

Thus, in one embodiment of the present invention, a target nucleic acid may associate with a certain combination of nucleic acid probes, leading to a characteristic "hybridization" pattern. Each positive association (or hybridization) event in a given sample provides a discrete piece of information about the target nucleic acid. In some cases the target nucleic acid may be sampled without determination of exactly where any particular nucleic acid probe associates with the target nucleic acid. Algorithms and software have been developed for target nucleic acid reconstruction, based on the hybridization pattern, and are known to those skilled in the art. In other cases, however, analysis of a hybridization pattern, such as those described herein, may provide a "fingerprint" identification of the target nucleic acid sequence, without specifically determining the target nucleic acid sequence itself. The pattern of hybridization may also be manually or computer analyzed.

Another aspect of the present invention is generally directed to systems and techniques for creating a collection of droplets, where the droplets contain distinguishable nucleic acid probes and/or identification elements. In some embodiments, a plurality of distinguishable identification elements may be used to identify a plurality of fluidic droplets, and in some cases, the distinguishable identification elements are used to determine a nucleic acid sequence (e.g., of a nucleic acid probe) present within each droplet. For instance, in one embodiment, at least about 64, at least about 256, at least about 1024, at least about 4096, or at least about 16,384 or more fluidic droplets may be prepared, each containing a nucleic acid probe (including multiple copies of the nucleic acid probe) and one or more identification elements that, in combination, identifies that nucleic acid probe and do not identify different nucleic acid probes. The present invention provides, in one set of embodiments, systems and methods for preparing such collections of fluidic droplets.

In one embodiment, a plurality of distinguishable identification elements are used to identify a plurality of fluidic droplets or nucleic acid probes or other suitable samples. For instance, if fluorescent particles are used, a set of distinguishable particles is first determined, e.g., having at least 5 distinguishable particles, at least about 10 distinguishable particles, at least about 20 distinguishable particles, at least about 30 distinguishable particles, at least about 40 distinguishable particles, at least about 50 distinguishable particles, at least about 75 distinguishable particles, or at least about 100 or more distinguishable particles. A non-limiting example of such a set is available from Luminex®. The distinguishable identification elements may be divided into a plurality of groups (e.g., 2, 3, 4, 5, 6, 7, or more), where each group contains at least two members of the set of distinguishable identification elements.

A sample may then be associated with one member chosen from each of the groups of distinguishable identification elements. For instance, a first sample may be identified by the combination of a first element chosen from a first group, a first element chosen from a second group, and a first element chosen from a third group, as each of these elements is distinguishable from each other; a second sample may be identified by the combination of a first element chosen from the first group, a first element chosen from the second group, but a second element chosen from the third group. The number of unique combinations, in this example, is simply the product of the number of members of each of the groups; a large number of distinguishable sets of identification elements can thus be prepared. Thus, for instance, by defining at least six identification elements, where the identification elements are arranged into at least three groups with each group having at least two identification elements, at least eight different samples can be determined by associating each of the at least eight samples with at least three of the identification elements, where each identification element associated with each sample is chosen such that there is one identification element from each of the at least three groups. Even larger numbers may be obtained by increasing the numbers of members in each group and/or the numbers of groups present. In addition, the number of members of each group may be the same, or different in some cases.

It should be noted that in other embodiments, other coding methods are also possible. For instance, the distinguishable elements may be used to represent binary digits, such that the nucleic acid probes or other samples are arbitrarily numbered and are identified by adding the binary digits corresponding to the distinguishable identification elements that are present.

Accordingly, in some embodiments, a fluidic droplet can be identified by introducing to the fluidic droplet, one or more identification elements that have been arranged in such a manner. Relatively large numbers of fluidic droplets can each be identified. For instance, a collection of tens, hundreds, or thousands of fluidic droplets, containing differing nucleic acid probes, may be identified by adding, to each of the droplets, three or four identification elements that have been determined in such a manner.

As a non-limiting example, in one set of embodiments, a set of 40 distinguishable identification elements may be used to encode up to about 10,000 distinguishable nucleic acid probes as follows. The 40 distinguishable identification elements are divided into 4 groups of 10 elements each. Each element of each group is number 1 through 0, and the four groups are labeled A, B, C, and D. One element from each group is added to a fluidic droplet (e.g., containing a nucleic acid probe), and the identification elements are read in the order ABCD. Thus, for instance, element 2 from group A, element 1 from group B, element 7 from group C, and element 6 from group D were found to be contained within a fluidic droplet, then the droplet would be $A_2$-$B_1$-$C_7$-$D_6$, or droplet number 2176. The identity of the droplet, and/or species contained within the droplet, could be determined based on this droplet number, e.g., through an arbitrary lookup table, or through some coding method. For instance, as another non-limiting example, a set of 24 distinguishable identification elements could be used to encode a 6-mer (e.g., contained within a nucleic acid probe) by dividing the identification elements into 6 groups, each containing 4 elements, such that each element represents a different base (e.g., A, C, T, or G), while each group represents a position. By including one element from each of the 6 groups within a fluidic droplet containing the 6-mer, the 6-mer may be identified by the set of identification elements present within the droplet. Thus, as an example, if element A from group 1, element C from group 2, element T from group 3, element T from group 4, element C from group 5, and element G from group 6 were present, the 6-mer contained within the droplet would be $1_A 2_C 3_T 4_T 5_C 6_G$, representing the sequence ACTTCG (SEQ ID NO: 1).

Figure 5:
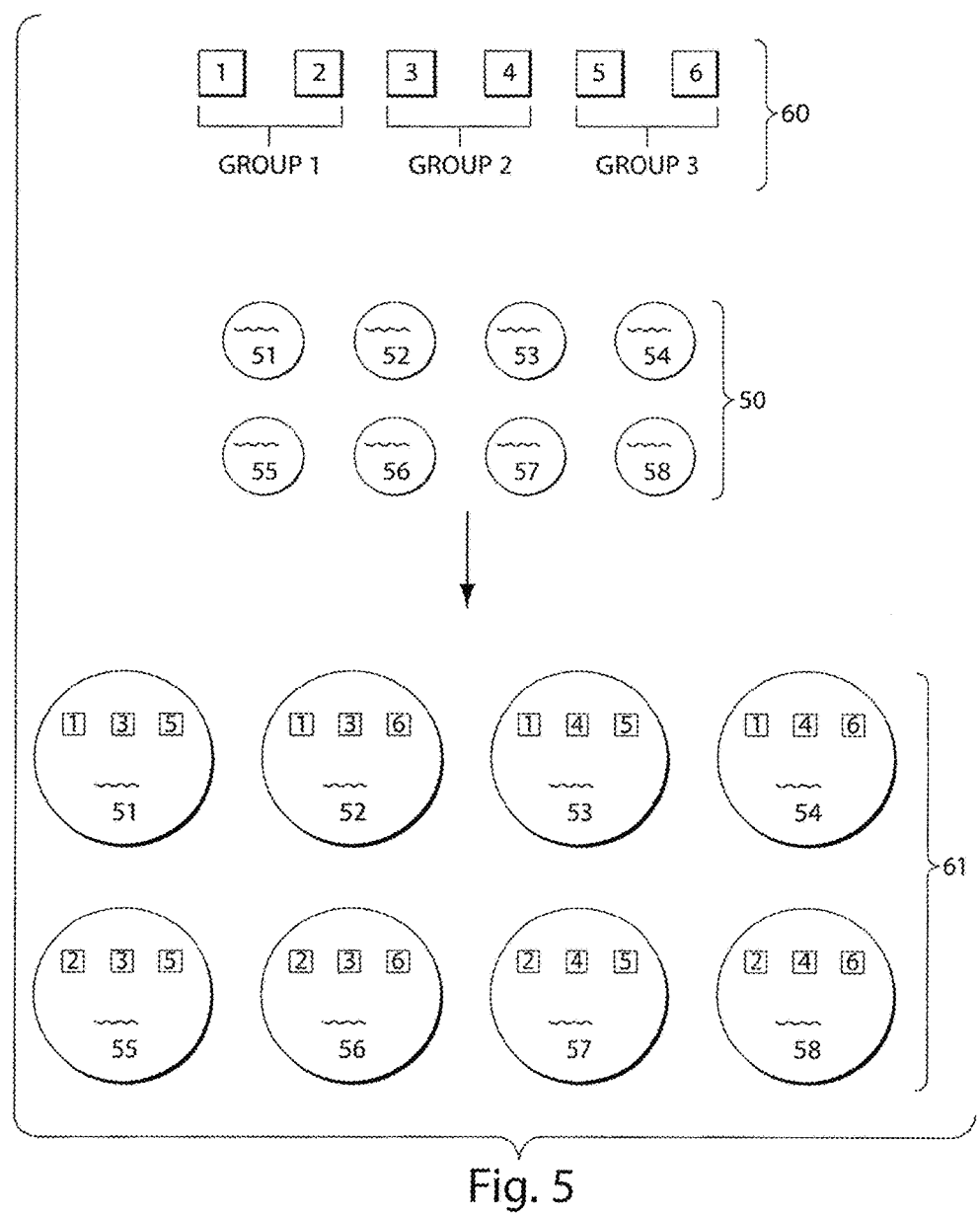
FIG. 5 shows an example of the preparation of a collection of droplets.

A non-limiting example of the creation of a collection of droplets is shown in FIG. 5. A plurality of eight fluidic droplets 50 is provided, each which contain a nucleic acid probe (numbered 51-58). Also provided are six distinguishable identification elements 60, which have been grouped into three groups (1 and 2 as group 1, 3 and 4 as group 2, and 5 and 6 as group 3). The distinguishable identification elements and nucleic acid probes are combined together in droplets 61 such that there are three distinguishable identification elements, one selected from each group, present within each of the eight droplets such that no two of the eight nucleic acid probes are associated with an identical set of three distinguishable identification elements. Accordingly, in this particular example, each of the eight fluidic droplets, each containing a nucleic acid probe, is identified by a set of three distinguishable identification elements.

The determination method of the identification elements and/or signaling entity for specific embodiments will depend on the components that are present within the fluidic droplets. As mentioned above, the determination may occur using techniques such as radioactivity, fluorescence, phosphorescence, light scattering, light absorption, fluorescence polarization, or the like. Many detectors that operate using such principles are commercially available. The detector may be used to determine at least one of the signaling entities and/or identification elements that may be present within a fluidic droplet, and in some cases, more than one detector may be used.

In some embodiments, the droplet is deformed such that the signaling entities and/or identification elements contained within the droplet passes a detector single file. A droplet may be deformed by passing it through a channel that has a constriction such that the cross-sectional area of the constriction is smaller than the cross-sectional area of the droplet when the droplet is in free solution, for example, as is shown in FIG. 6C. In some cases, the droplet is deformed such that substantially all of the signaling entities and/or identification elements are arranged within the droplet such that no two are able to simultaneously cross an imaginary plane that is perpendicular to the direction of motion of droplet.

In some embodiments, the detection may be parallelized, i.e., a number of signaling entities and/or identification elements may be simultaneously determined within one channel and/or within a plurality of channels. For example, a timing device may be used to synchronize detection of the parallel paths. Another non-limiting example of parallelized detection is the use of a camera or other imaging device positioned so as to be able to image more than one channel, e.g., simultaneously. The camera may be, for example, a linescan camera, a 2D CCD camera, or the like. In one specific embodiment, at least one mercury arc lamp may illuminate a selected number of channels and multiple cameras (which may each have an individual filter) may be used to capture a particular color spectrum. The images may be captured sequentially, or simultaneously, e.g., so that the location of each droplet is the same in all camera images.

Figure 18A:
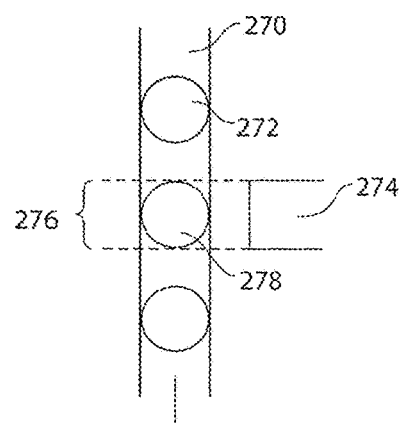
FIG. 18A depicts the determination of signaling entities and/or identification elements in droplet one at a time in a single microfluidic channel.
Figure 18B:
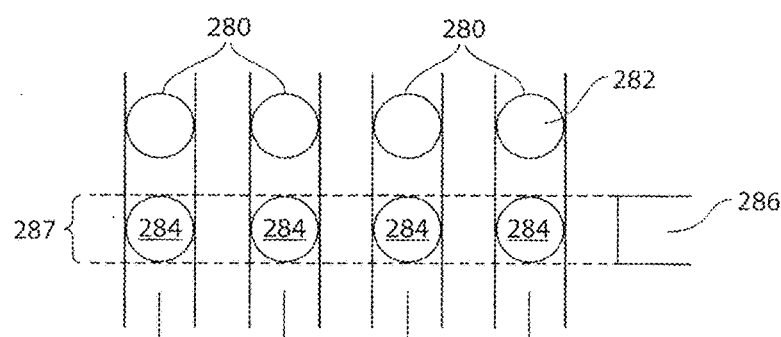
FIGS. 18B and 18C depict the determination of signaling entities and/or identification elements in a plurality of droplets at a single time in a plurality of channels or in a contained area, respectively.
Figure 18C:
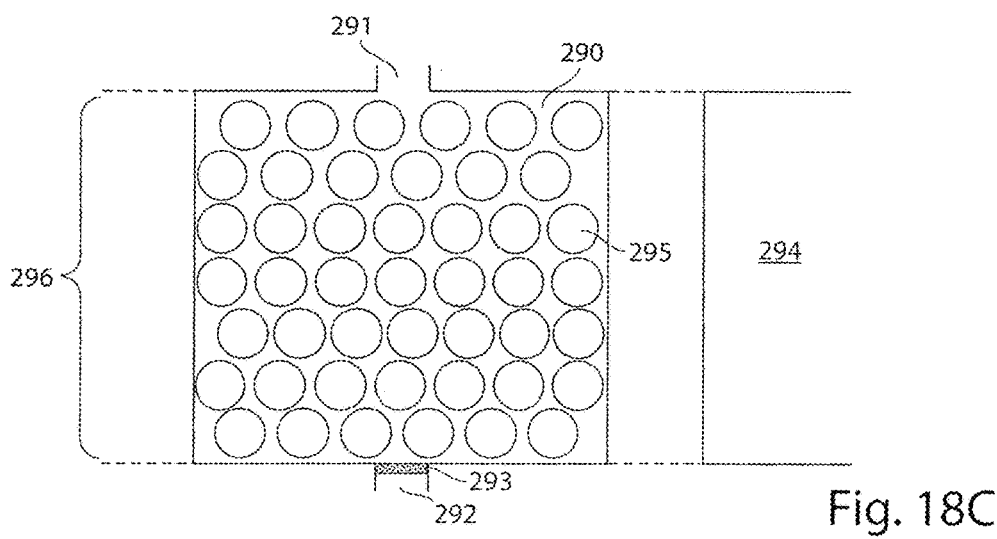

In some cases, the signaling entities and/or identification elements of a single droplet may be determined at a point in time. For example, as illustrated in FIG. 18A, a plurality of droplets 272 are flowed through microfluidic channel 270. Detector 274 is positioned with respect to channel 270 such that a single droplet 278 (or a portion of droplet 278) is determined at a time. Detector 274 may determine the signaling entities and/or identification elements in cross-section area 276. In other cases, the signaling entities and/or identification elements from a plurality of droplets may be determined at a time. For example, as illustrated in FIG. 18B, a plurality of droplets 282 are flowed through a plurality of microfluidic channels 280 (in this non-limiting example, four channels are illustrated). Detector 286 is positioned with respect to channels 280 such that the signaling entities and/or identification elements from a plurality of droplets 284 that pass the detector in cross-section area 287 in the microfluidic channels 282 are determined. As another non-limiting example, as illustrated in FIG. 18C, a plurality of fluidic droplets 295 may be flowed into a contained area 290 through inlet 291. Detector 294 is positioned relative to the contained area 290 such that the signaling entities and/or identification elements from plurality of droplets 295 in the cross-sectional area 296 may be determined. In some cases, contained area 290 may have an outlet 292 which may comprise a gate 293 (e.g., a valve) to control the flow of the plurality of fluidic droplets. Gate 293 may allow for the flow of fluid but not the flow of the fluidic droplets, in some cases. In some cases, at least about one hundred, at least about one thousand, at least about ten thousand, at least about one hundred thousand, at least about five hundred thousand, at least about 1 million, at least about 5 million, at least about 10 millions droplets may be determined per second.

In instances where a plurality of droplets may be determined at a single time, methods and/or systems may be used which aids in the determination of the plurality of droplets. In some cases, in order to simultaneously image an array of droplets, the detector may need to determine the boundaries of adjacent droplets such that only one signal is determined per droplet. According to one set of embodiments, the following methods and/or systems employing a light source to create droplet glare may be advantageous when determining a plurality of droplets which are collected in a contained area because it may be difficult to determine the boundaries (e.g., edges) of a droplet in order to determine droplet.

In some cases, a droplet may be determined by determining a signal of a position relative to a reference spot. That is, each droplet may be related to a references spot and a determination of the signal of a droplet may be determined by relation to the reference spot. Production of a reference spot may be accomplished, for example, by shining a light on the surface of the droplets such that a droplet glare is produced for each droplet. This may allow for the detector to determine a relative location for each droplet, and thereby determine a signal each droplet, as described more herein.

Figure 44:
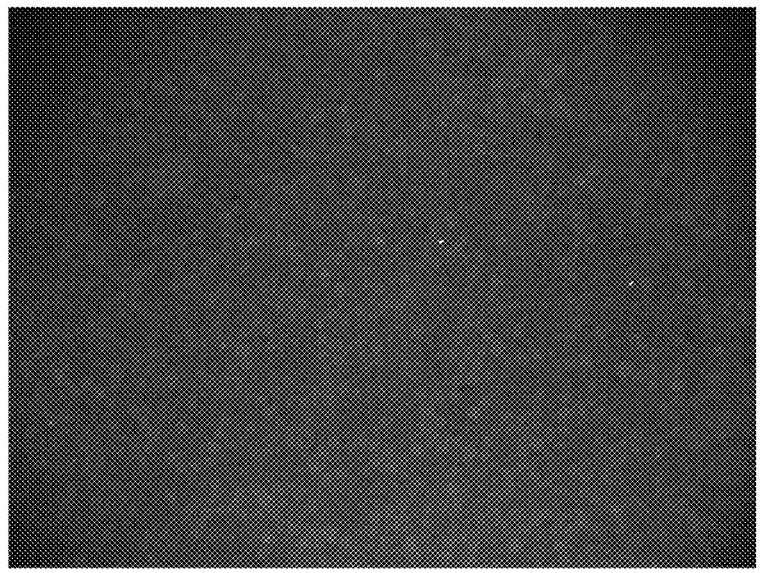
FIG. 44 shows a still image capture from a CCD camera of fluorescent intensity of a plurality of microfluidic droplets with two discrete fluorescent intensity populations.
Figure 45:
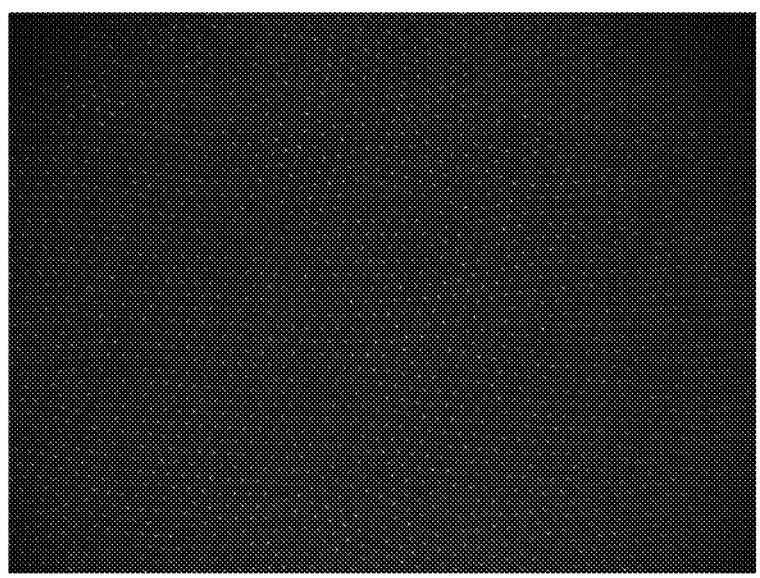
FIG. 45 shows a still image capture from a CCD camera of a plurality of droplets with two discrete fluorescent intensity populations comprising droplet glare.

In some cases, when determining a plurality of droplets, a second light source (e.g., a lamp, an LED array), in addition to the light source used to probe for fluorescence may be employed. The second light source may be shone at an angle (e.g., a non-orthogonal angle) to the droplets being determined (e.g., being visualized under a microscope). Due to the orientation of the light and the refraction within the spherical drops (as discussed herein), scattered light may be captured by the lens of the camera and a relatively concentrated and bright glare on the image of each drop is produce (e.g., a droplet glare) that is easily visible and distinguishable from the background signal. Thus, a substantially focused glare may be produced by the droplet due to the scattering of light within the droplet. For example, FIG. 44 shows a still image capture from a CCD camera of fluorescent intensity of microfluidic droplets with two discrete fluorescent intensity populations. The tight packing of the droplets may cause difficulties in determining the boundaries of the droplets. FIG. 45 shows a still image capture from a CCD camera of a similar environment as above in FIG. 44 utilizing a second light source shining at an oblique angle on the droplets. Droplet glare is visualized for each droplet and can be seen on every drop.

In some cases, a light source may be directed toward a plurality of microfluidic droplets on a surface such that droplet glare is produced in substantially all of the plurality of droplets due to light scattering within the droplets. The droplet glare formed on the droplets may be utilized to determine the position of the droplets. In some instances, the droplet glare may be quantified. In some cases, software may be used to determine and/or quantify the droplet glare associated with the droplets. For instance, the droplet glare may be positioned at approximately the same angle and distance from the center of the droplets and therefore acts as a reference point for each of the droplets. In some cases, the droplet glare may be offset from the center of each droplet, and therefore, the droplet glare can be used to identify a reference point for each droplet in the same frame as used for gathering the fluorescent data. Thus, in some instances, there is no need to turn on and off the droplet glare (e.g., by turning on and off light sources), and/or to separate the droplet identification and data acquisition processes.

Figure 34:
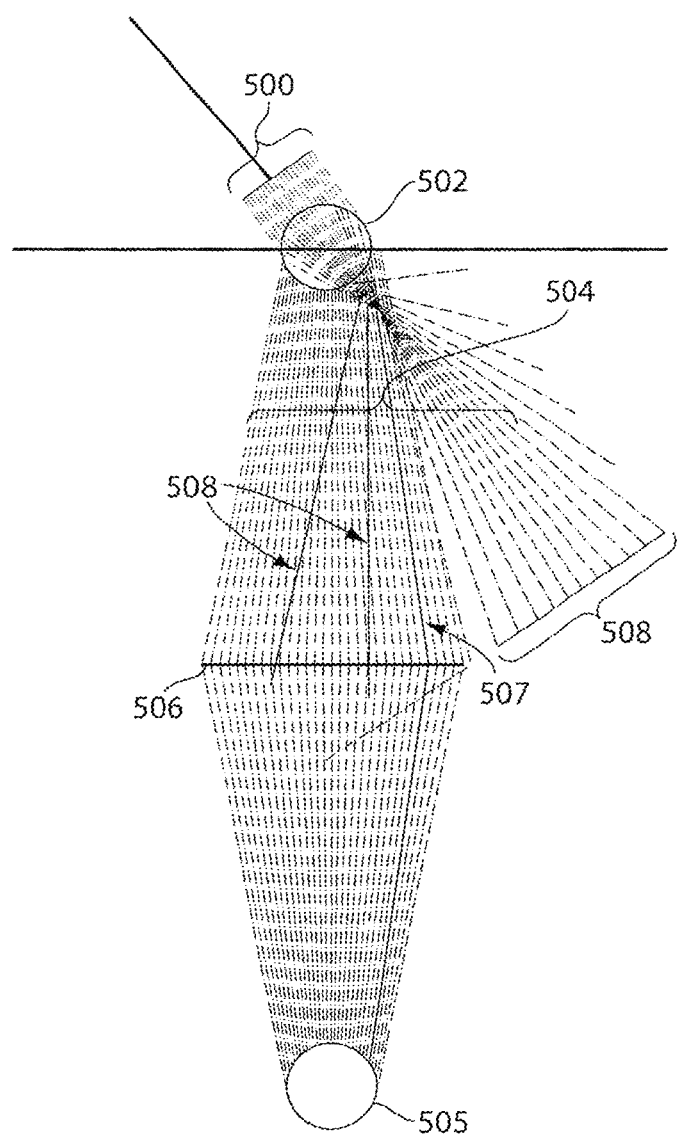
FIG. 34 shows a schematic of the refraction of light through a microfluidic droplet and the resulting droplet glare that will appear on the image of the drop, according to one embodiment.

FIG. 34 shows a schematic of the method described in this example detailing the refraction of the lighting through a microfluidic droplet and the resulting glare that will appear on the image of the drop. In this non-limiting example, the light is shone at a 55° angle (although almost any non-orthogonal angle can be used in other cases). The objective lens size and distance relative to droplet are not drawn to scale. In this figure, lighting 500 (e.g., oblique lighting) is shown at a 55° angle onto a microfluidic droplet 502 being imaged 505 on a microscope stage. Refracted rays of light 504 trace the path of refraction through the droplet, and it can be seen that there is only a small region of scattered light 504 that is gathered by the objective lens 506 and is refracted light 507 the plane of focus. This results in droplet glare on the image of the particle when viewed through the microscope. There are many regions of scattered light 508 which are not in the plane of focus.

In some embodiments, if oblique lighting to be originating from a source sufficiently far away (e.g., approximately 1 foot from the droplets) then an array of droplets tightly packed on the surface of the microscope stage should see collimated lighting approaching each droplet at the same incident angle to the stage. This will result in the same refraction pattern for each droplet; thus, the droplet glare will appear in the same position on the image of each droplet, thereby creating a reference point for each droplet that is at approximately the same angle and distance from the center of each droplet.

While a droplet glare may be created by using oblique lighting at various angles, in some embodiments, there may be limitations to the range to the angle which will give the best results. For example, if the lighting occurs at a steep angle, then the resulting droplet glare may occur closely to the center of the droplet image which may interfere with the gathering of other optical information from the droplet such as fluorescent intensity. On the other hand, in some embodiments, if the lighting is shone at too shallow an angle, in some cases, none of the refracting rays would be gathered by the objective and therefore, no droplet glare will be seen in the droplet image. The angles that are suitable for a given experimental set-up may be determined experimentally.

The presence and/or position of the droplet glare may be determined by observing the image and the angle of the light source may be adjusted accordingly to produce the desired presence and/or position of the droplet glare. In some embodiments, the angle of the second light source is less than about 30°, between about 30° and about 80°, greater than about 80°, between about 40° and about 70°, about 20°, about 30°, about 40°, about 50°, about 60°, about 70°, about 80°, or the like.

Figure 35:
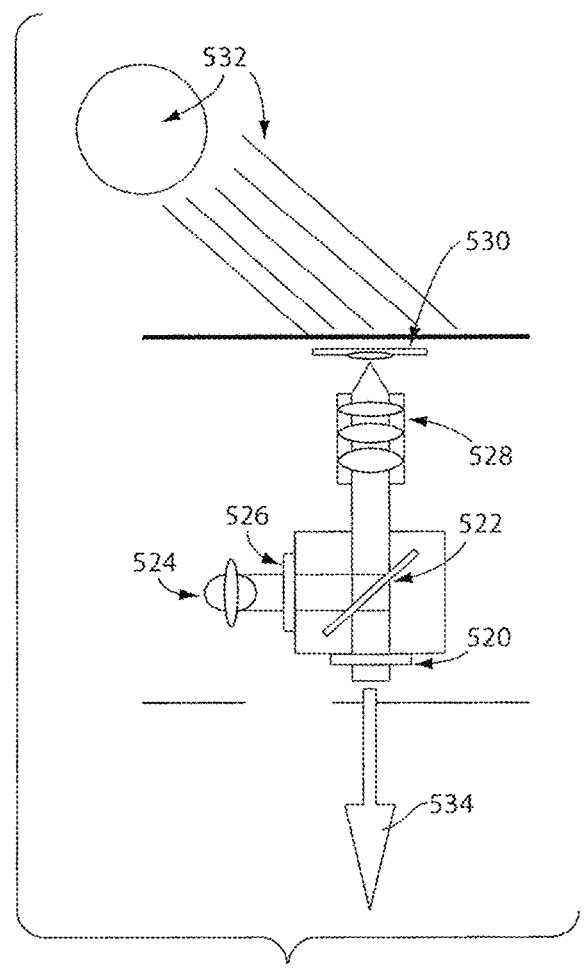
FIG. 35 depicts an example of an experiment set-up that may be used to produce droplet glare, according to one embodiment.

In some cases, an experimental set-up employing a second light source may be as depicted in FIG. 35. A fluorescent microscope may be provided, for example, comprising an emission filter 520, a dichroic mirror 522, an arc lamp 524, an excitation filter 526, and an objective lens 528. A plurality of droplets to be determined may be positioned on the microscope stage 530. Oblique lighting 532 (e.g., second light source) may be provided at an angle (e.g., approximately 55°). Light exciting the microscope 534 may be recorded by a detector or an imager (e.g., a CCD camera, etc.). The above experimental set-up is by no means limiting and those of ordinary skill in the art will be able determine additional components and/or other arrangements that are possible using only routine skill.

Images of the plurality of droplets may be captured by a detector or an imager, such as a CCD camera. In some embodiments, the CCD cameras may comprise filters that only allow for light in a narrow spectrum to pass to the camera (e.g., red light, green light, etc.) such that specified fluorescent images may be obtained. In instances where more than one camera is employed, the capture of images may or may not be synchronized. In a particular embodiment, the capture of images is synchronized to allow simultaneous capture of fluorescent information at a first and a second wavelength. In some embodiments, the second light source may be selected such that the droplet glare may be observed in only one of the at least two images (e.g., light from a green LED source may only be observed in the image acquired by the camera which has a green wavelength capture).

In some embodiments, e.g., if the droplet glare formed is distinctly more intense than the background, software identification of the location of the droplets may be completed using simple methods. The droplet glare can be used as a reference point as the droplet glare generally appear consistently in regards to both direction and distance from the center of each droplet. Depending on the set-up of the oblique lighting, the droplet glares can be place offset from the center of the drop and allow for the same image frame for both droplet identification and data acquisition. Therefore, the oblique lighting may or may not be on and off and/or images may or may not have to be taken at slightly different time points.

The images collected may be processed as follows. In some cases, at least one image (e.g., comprising the droplet glares) may be processed by using a simple intensity threshold programs to determine the droplet glares on each droplet. The software can compute, or human input may be used, to determine the angle and/or the distance between a droplet glare and the center of the droplet. In some embodiments, the angle and/or distance between a droplet glare and the center of the droplet may be recorded a single time (e.g., if the experimental set-up is not varied). Software may be used to create a sampling mask relative to each droplet glare (e.g., to determine the location of each droplet relative to the corresponding droplet glare). The sampling mask can be overlaid with each image taken at the corresponding time (e.g., the first and second images taken with a first and a second camera). This can allow for the creation of a marking system for each droplet which defines boundaries within a droplet where a signal (e.g., a fluorescent intensity reading) is to be taken. A specific example of this method is described in Example 12.

In some cases, an imaging system may be provided that may be used to image a plurality of microfluidic droplets on a surface (e.g., in a microfluidic channel or contained area). The imaging system may comprise a first light source able to focus light orthogonally toward the plurality of microfluidic droplets disposed on the surface and a second light source able to focus light at a substantially non-orthogonal angle toward the plurality of microfluidic droplets disposed on the surface. For example, the first light source may be the light source from a microscope and the second light source may be a lamp, an LED, etc. The imaging system may also comprise an imager able to image scattered (e.g., droplet glare) and nonscattered light (e.g., fluorescence) arising from the plurality of microfluidic droplets disposed on the surface. The nonscattered light may arise from the first light source and the scattered light may arise from the second light source. In some cases, the imager may be able to simultaneously image the scattered and nonscattered light arising from the plurality of microfluidic droplets disposed on the surface. For example, the imager may be a camera such as a CCD camera. In some cases, the imaging system may comprise more than one imager, at least two imagers, at least three imagers, at least four imagers, and the like. Those of ordinary skill in the art will be able to determine additional arrangement and components (e.g., a third light source, a filter) that may accompany the described imaging system. The imaging system may be able to simultaneously image at least one thousand, at least five thousand, at least ten thousand, at least twenty thousand, at least thirty thousand, at least forty thousand, at least fifty thousand, at least one hundred thousand, or the like, droplets at a time.

In some, but not all embodiments, all components of the systems and methods described herein are microfluidic. "Microfluidic," as used herein, refers to a device, apparatus or system including at least one fluid channel having a cross-sectional dimension of less than 1 mm, and a ratio of length to largest cross-sectional dimension perpendicular to the channel of at least about 3:1. A "microfluidic channel," as used herein, is a channel meeting these criteria.

Microfluidic systems may be provided that are able to cause two or more droplets to fuse or coalesce into one droplet, for example, in cases where the two or more droplets ordinarily are unable to fuse or coalesce, for example due to composition, surface tension, droplet size, etc. as known to those of ordinary skill in the art. Examples of embodiments in which two or more droplets are fused have been described above. The fluidic droplets may be fused together using any suitable technique, for example, as discussed in U.S. patent application Ser. No. 11/246,911, filed Oct. 7, 2005, entitled "Formation and Control of Fluidic Species," by Link, et al., published as U.S. Patent Application Publication No. 2006/0163385 on Jul. 27, 2006; or U.S. patent application Ser. No. 11/360,845, filed Feb. 23, 2006, entitled "Electronic Control of Fluidic Species," by Link, et al., published as U.S. Patent Application Publication No. 2007/0003442 on Jan. 4, 2007, each incorporated herein by reference. As an example, in microfluidic systems, the surface tension of the droplets, relative to the size of the droplets may prevent fusion or coalescence of the droplets from occurring. In one embodiment, two droplets may be given opposite electrical charges (i.e., positive and negative charges, not necessarily of the same magnitude), which may increase the electrical interaction of the two droplets such that fusion or coalescence of the droplets can occur. Electrical charges (positive or negative) may be imparted onto droplets through the use of Taylor cones, or through any other suitable techniques. For instance, an electric field may be imposed on a reactor containing the droplets, the droplets may be passed through a capacitor, a chemical reaction may occur to cause the droplets to become charged, flowing the droplets over a region with opposite wetting properties, etc.

The "cross-sectional dimension" of the channel is measured perpendicular to the direction of fluid flow. Most fluid channels in components of the invention have maximum cross-sectional dimensions less than about 2 mm, and in some cases, less than about 1 mm. In one set of embodiments, all fluid channels containing embodiments of the invention are microfluidic or have a largest cross sectional dimension of no more than about 2 mm or about 1 mm. In another embodiment, the fluid channels may be formed in part by a single component (e.g. an etched substrate or molded unit). Of course, larger channels, tubes, chambers, reservoirs, etc. can be used to store fluids in bulk and to deliver fluids to components of the invention. In one set of embodiments, the maximum cross-sectional dimension of the channel(s) containing embodiments of the invention are less than about 500 microns, less than about 200 microns, less than about 100 microns, less than about 50 microns, or less than about 25 microns.

A "channel," as used herein, means a feature on or in an article (substrate) that at least partially directs the flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least about 2:1, more typically at least about 3:1, at least about 5:1, or at least about 10:1 or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channel may be of any size, for example, having a largest dimension perpendicular to fluid flow of less than about 5 mm or about 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

Non-limiting examples of microfluidic systems that may be used with the present invention are disclosed in U.S. patent application Ser. No. 11/246,911, filed Oct. 7, 2005, entitled "Formation and Control of Fluidic Species," published as U.S. Patent Application Publication No. 2006/0163385 on Jul. 27, 2006; U.S. patent application Ser. No. 11/024,228, filed Dec. 28, 2004, entitled "Method and Apparatus for Fluid Dispersion," published as U.S. Patent Application Publication No. 2005/0172476 on Aug. 11, 2005; U.S. patent application Ser. No. 11/360,845, filed Feb. 23, 2006, entitled "Electronic Control of Fluidic Species," published as U.S. Patent Application Publication No. 2007/000342 on Jan. 4, 2007; International Patent Application No. PCT/US2006/007772, filed Mar. 3, 2006, entitled "Method and Apparatus for Forming Multiple Emulsions," published as WO 2006/096571 on Sep. 14, 2006; U.S. patent application Ser. No. 11/368,263, filed Mar. 3, 2006, entitled "Systems and Methods of Forming Particles," published as U.S. Patent Application Publication No. 2007/0054119 on Mar. 8, 2007; U.S. Provisional Patent Application Ser. No. 60/920,574, filed Mar. 28, 2007, entitled "Multiple Emulsions and Techniques for Formation"; and International Patent Application No. PCT/US2006/001938, filed Jan. 20, 2006, entitled "Systems and Methods for Forming Fluidic Droplets Encapsulated in Particles Such as Colloidal Particles," published as WO 2006/078841 on Jul. 27, 2006, each incorporated herein by reference in their entireties.

In some embodiments, the systems of the present invention may be non-microfluidic devices. For example, two or more droplets may be fused, manipulated and/or coalesced using Couette shear cells, shaken emulsions, and/or membrane emulsification. In some embodiments, two or more droplets may be fused, manipulated and/or coalesced into one droplet using electric and/or magnetic fields, e.g., from one or more field-generating components contained within a substrate. Non-limiting examples of systems comprising a plurality of electric and/or magnetic field-generating components arranged to be able to interact and/or manipulate a sample are disclosed in U.S. patent application Ser. No. 11/105,322, filed Apr. 13, 2005, entitled "Methods and Apparatus for Manipulation and/or Detection of Biological Samples and Other Objects," by Ham, et al., published as U.S. Patent Application Publication No. 2006/0020371 on Jan. 26, 2006, and International Patent Application No. PCT/US2008/007941, filed Jun. 26, 2008, entitled "Methods and Apparatus for Manipulation of Droplets," each incorporated herein by reference.

In some cases, the field generating components may be arranged in an array. By generating electric and/or magnetic fields using one or more electric and/or magnetic field-generating components by activating the components in a specific order, fluidic droplets or other samples can be moved relative to a substrate. For example, two fluidic droplets can be given opposite electric charges (i.e., positive and negative charges, not necessarily of the same magnitude), which may increase the electrical interaction of the two droplets such that fusion or coalescence of the droplets can occur due to their opposite electric charges. For instance, an electric field may be applied to the droplets using one or more electric field-generating components.

In one embodiment, a kit may be provided, containing one or more of the above compositions. A "kit," as used herein, typically defines a package or an assembly including one or more of the compositions of the invention, and/or other compositions associated with the invention, for example, as previously described. Each of the compositions of the kit may be provided in liquid form (e.g., in solution), in solid form (e.g., a dried powder), etc. A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the compositions and/or other compositions associated with the kit. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

The following references are herein incorporated by reference: U.S. Provisional Patent Application Ser. No. 61/008,862, filed Dec. 21, 2007, entitled "Systems and Methods for Nucleic Acid Sequencing," by Weitz, et al., and U.S. Provisional Patent Application Ser. No. 61/098,710, filed Sep. 19, 2008, entitled "Systems and Methods for Nucleic Acid Sequencing," by Weitz, et al., each incorporated herein by reference. Also, incorporated herein by reference is a U.S. provisional patent filed on even date herewith, entitled "Creation of Libraries of Droplets and Related Species," by Weitz, et al.

The following examples are included to demonstrate various embodiments of the invention. Those of ordinary skill in the art should, in light of the present disclosure, appreciate that many changes can be made in the specific embodiments which are disclosed and still obtain a like or similar result without departing from the spirit and scope of the invention. Accordingly, the following examples are intended to illustrate certain embodiments of the present invention, but do not exemplify the full scope of the invention.

EXAMPLE 1

Non-limiting examples of methods for DNA sequencing are described in the following prophetic examples. The figures are illustrated using pentamers for illustrative purposes only. Other lengths may also be used. In addition, modified residues such as locked nucleic acid residues, and/or universal residues may also be used in some cases.

An example method is discussed with reference to FIG. 6. Specifically, this method is an example using a bead-based labeling strategy, modified nucleotides, and fluorescence. FIG. 6A shows a plurality of color-coded beads used as identification elements, for instance, beads such as those made by Luminex® Corporation. The beads in this example are 5 μm diameter beads that can be divided into 100 distinguishable types (150), for instance, based on the fluorescence intensity of two distinct dyes. These beads are arbitrarily numbered 1-100.

The beads may be used for identification as follows. 40 of these distinguishable beads can be divided into four groups of beads, each containing 10 members, as is shown in FIG. 6B (beads 41-100 are not used in this example). In this particular example, all droplets have a single distinguishable bead taken from each of the four sets of beads (although there may be more than one identical copy of each type of bead present) (FIG. 6B). For simplicity in this example, each bead represents a numerical place value in the base (10) system (although other methods may be used in other embodiments). For example, beads 1, 11, 21, and 31 may be selected to represent a 1 value, and beads 10, 20, 30 and 40 represent a value of 0. As a specific example, the 2176th solution or label contains the beads 6 (151), 17 (152), 21 (153), and 32 (154) (FIG. 6C).

Figure 6D:
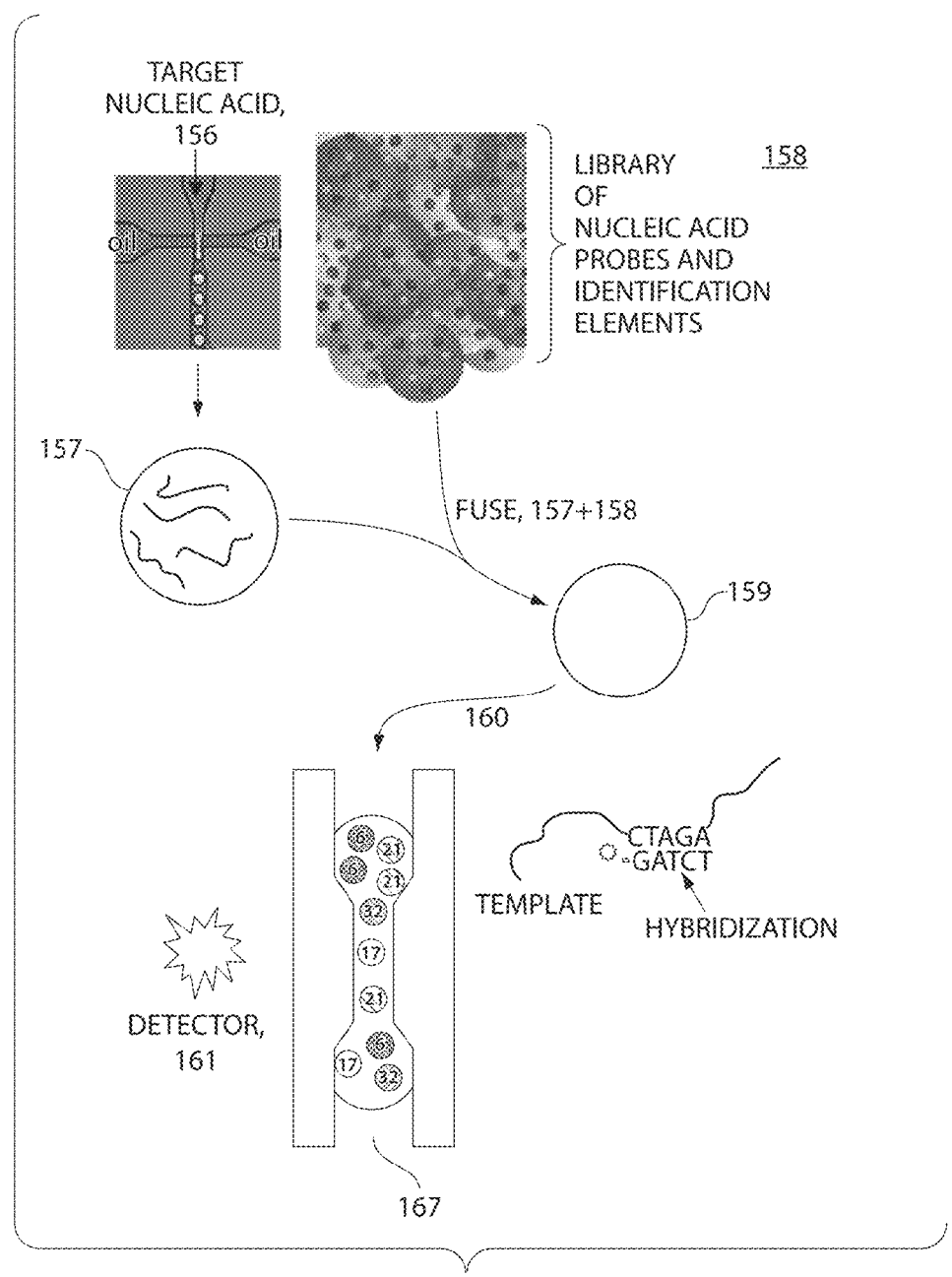

In the example shown, this droplet also contains the labeled nucleic acid probe 5'-*GATCT-3'(155) (SEQ ID NO: 2) (where * is a signaling entity, such as a fluorescent entity), which may be modified in some cases to incorporate one or more locked nucleotides and/or universal residues. Solutions containing the nucleic acid probe and the beads can be each individually emulsified and pooled to create a collection of analytical droplets 158 containing a nucleic acid probe and at least four distinguishable beads (FIG. 6D). A target nucleic acid 156 is provided to a microfluidic device (not shown) and a plurality of droplets 157, each containing the target nucleic acid, are formed, e.g., via droplet-droplet fusion techniques. Droplets 157 are then fused with droplets 158 to form a plurality of fused droplets 159, which each contain the target nucleic acid, a nucleic acid probe, and the corresponding identification elements.

The association of the target nucleic acid and the nucleic acid probe is determined in this example as follows, although other techniques may be used in other cases. The plurality of fused droplets 159 is passed, as indicated by arrow 160, into channel 167 and the droplet deformed such that each bead within the droplet passes detector 161 single file. In the example shown, if the nucleic acid probe binds to the target nucleic acid within the droplet, then there will be a change in fluorescence spectra of the nucleic acid probe, which can be determined using the detector. The beads and the signaling entity within the droplet are determined as they pass detector 161 single file, and the resulting amount of fluorescence is recorded. In this example, if there is a change in fluorescence of the signaling entity indicative of association of the target nucleic acid and the nucleic acid probe (for example, caused by the release of a quencher from the nucleic acid probe), then the identity of the droplet may be determined by determining the four distinguishable beads contained within the droplets. For instance, if the beads determined by the detector are identified as beads 6, 17, 21, and 32 (corresponding to probe labeled nucleic acid probe 5'-*GATCT-3' (SEQ ID NO: 2)), then it can be determined that the complement of sequence 5'-GATCT-3' (SEQ ID NO: 2) occurs on the target nucleic acid.

EXAMPLE 2

Figure 7A:
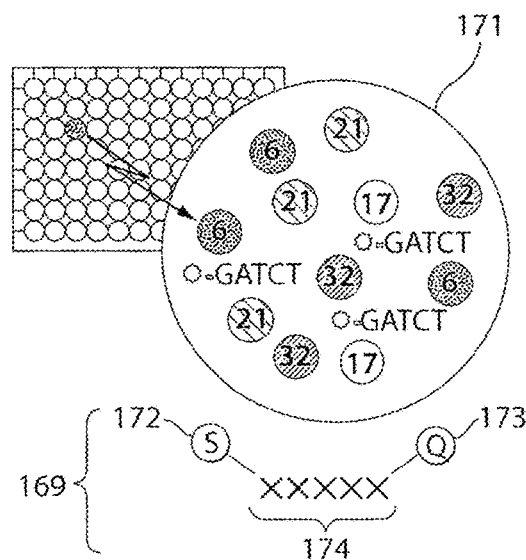

This example employs a bead-based labeling strategy, a TaqMan® probe, and fluorescence. As in Example 1, the droplets have a single member taken from each of four sets of identification element bead-types. FIG. 7A shows an example of the possible components in one droplet 171, as given in FIG. 6. TaqMan® analysis will be used in the droplets in this example.

Nucleic acid probe 169 comprises oligonucleotide 174, signaling entity 172, and quencher 173, which reduces (or enhances) fluorescence from signaling entity 172 by the use of Fluorescence (or Förster) Resonance Energy Transfer (FRET), which is the inhibition of one dye caused by another without emission of a photon. The signaling entity in this particular example is found on the 5' end of the oligonucleotide and the quencher at the 3' end.

Figure 7B:
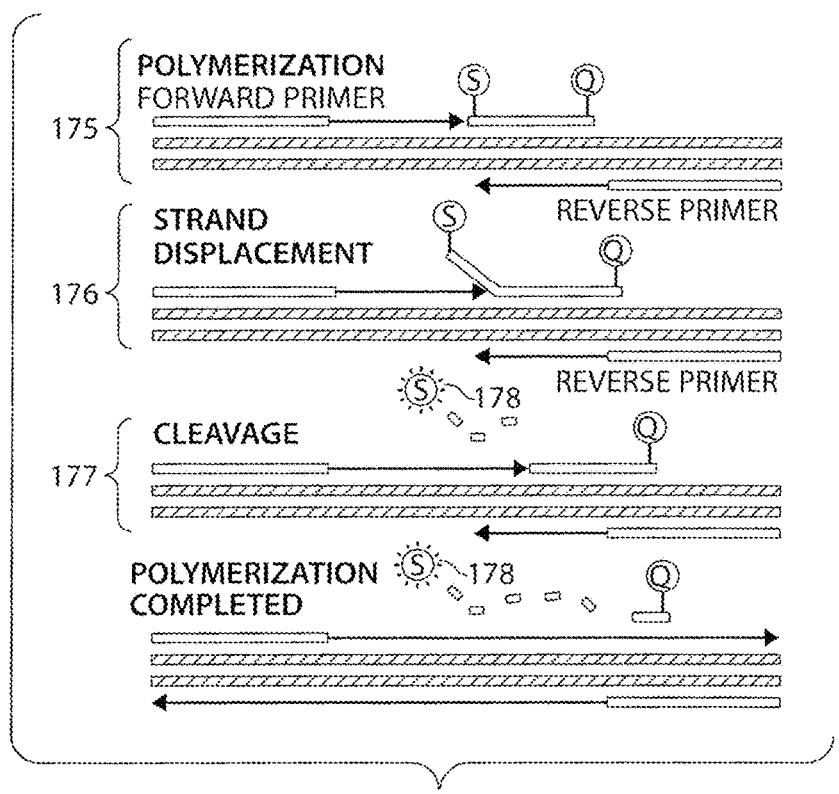

The TaqMan® probe anneals to a target nucleic acid, as shown by 175 in FIG. 7B. Taq polymerase then adds nucleotides until it gets to the TaqMan® probe as shown by 176. Non-complementing TaqMan® probes are displaced. The complementing TaqMan® probes are degraded from the target nucleic acid by Taq polymerase 5' to 3' exo activity. Thus, if the nucleic acid probe associates with the target nucleic acid, as indicated in 177, quencher 173 is separated from signaling entity 172, allowing signaling entity 172 to be determined, as shown by 178.

Figure 7C:
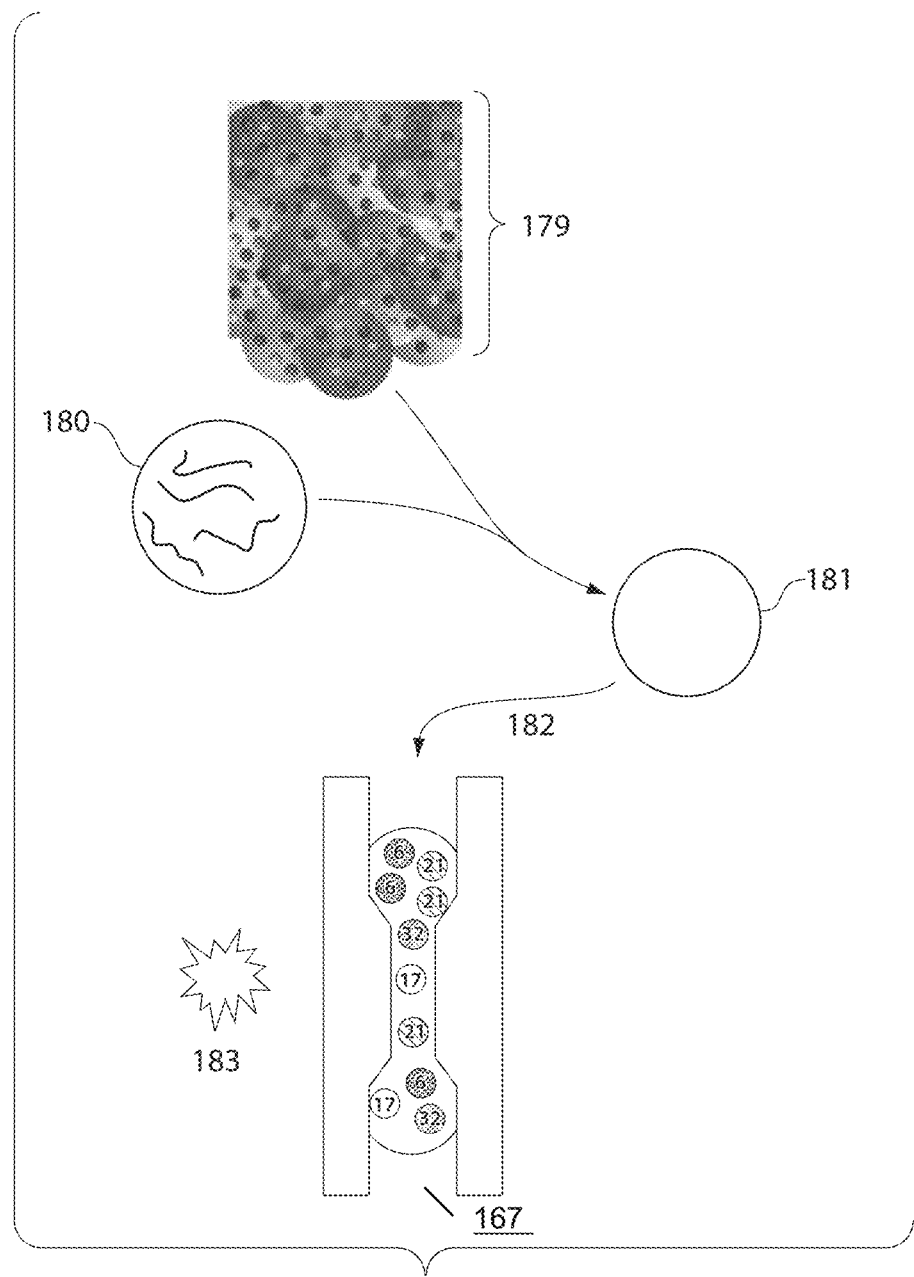

As in Example 1, the association of the target nucleic acid and the nucleic acid probe can then be determined using any suitable technique. In this example, a plurality of nucleic acid probes (in this case, attached to a signaling entity and a quencher) and one or more identification elements are combined to form a collection of analytical droplets 179, and are fused with a plurality of droplets 180 containing target nucleic acid and, in this example, Taq polymerase, as shown in FIG. 7C. Droplets 179 are then fused with droplets 180 to form a plurality of fused droplets 181. The droplets 181 are passed, as shown by arrow 182, into channel 167 to be determined by detector 183. If the nucleic acid probe binds to the target nucleic acid, then the signaling entity may be released. Accordingly, a difference in the fluorescence in the signaling entity may be used to determine association of the nucleic acid probe and the target nucleic acid.

EXAMPLE 3

This particular example employs DNA ligation, bead-labeling and fluorescence. Luminex® Corporation provides beads that can be separated into 100 distinguishable beads 210, as shown in FIG. 8A. Each bead type can be coated with a reagent specific to a particular bioassay, allowing the capture and detection of specific analytes from a sample. Lasers excite the internal dyes that identify each bead particle, and also any reporter dye captured during the assay.

FIGS. 8B and 8C illustrate the following: forty beads are divided into four groups of 10 distinguishable beads each, and each bead will have attached primers such that the first set of 10 beads will have an "A"-type set and various universal residues 214 (i.e. beads 1-10 will each have attached to them the oligonucleotide probe-set 5'-ANNNN-3'), the second set of 10 bead-types (i.e., beads 11-20) will have a "C"-type oligonucleotide 213 attached to them (i.e. 5'-CNNNN-3'), the third set of 10 bead-types (i.e., beads 21-30) will have a "G"-type oligonucleotide 212 attached to them (i.e. 5'-GNNNN-3'), and the fourth set of 10 bead-types (i.e., beads 31-40) will have a "T"-type oligonucleotide 211 attached to them (i.e. 5'-TNNNN-3').

Figure 8D:
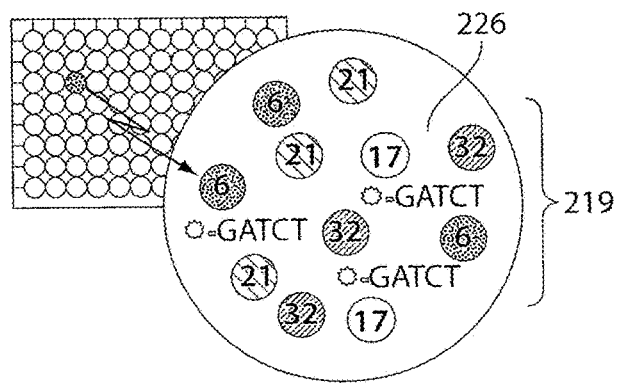

Each bead-type also represents a numerical value in the base (10) system, similar to the systems previously discussed. For example, beads 1, 11, 21, and 31 represent a 1 value, (for simplicity, beads 10, 20, 30 and 40 represent a 0 value). The first 10 bead-types (A type set) represent the ones place-value (number value from 0 to 9). The second digit is the "C digit" and represents the tens place value. The third digit is the "G digit," and the last digit is the "T digit." A four-digit number is encoded by the forty bead-types in the order TGCA (FIG. 8D) in this particular example. For example, the 2176th droplet-type 219 contains the Luminex® bead-types 6-A (215), 17-C (217), 21-G (216), and 32-T (218) (FIGS. 8C and 7D). In the figure, as an example, droplet 219 also contains a nucleic acid probe, for example, probe 5'-*GATCT-3' (SEQ ID NO: 2) (226) (although multiple copies of that nucleic acid probe may be present within the droplet).

Figure 8E:
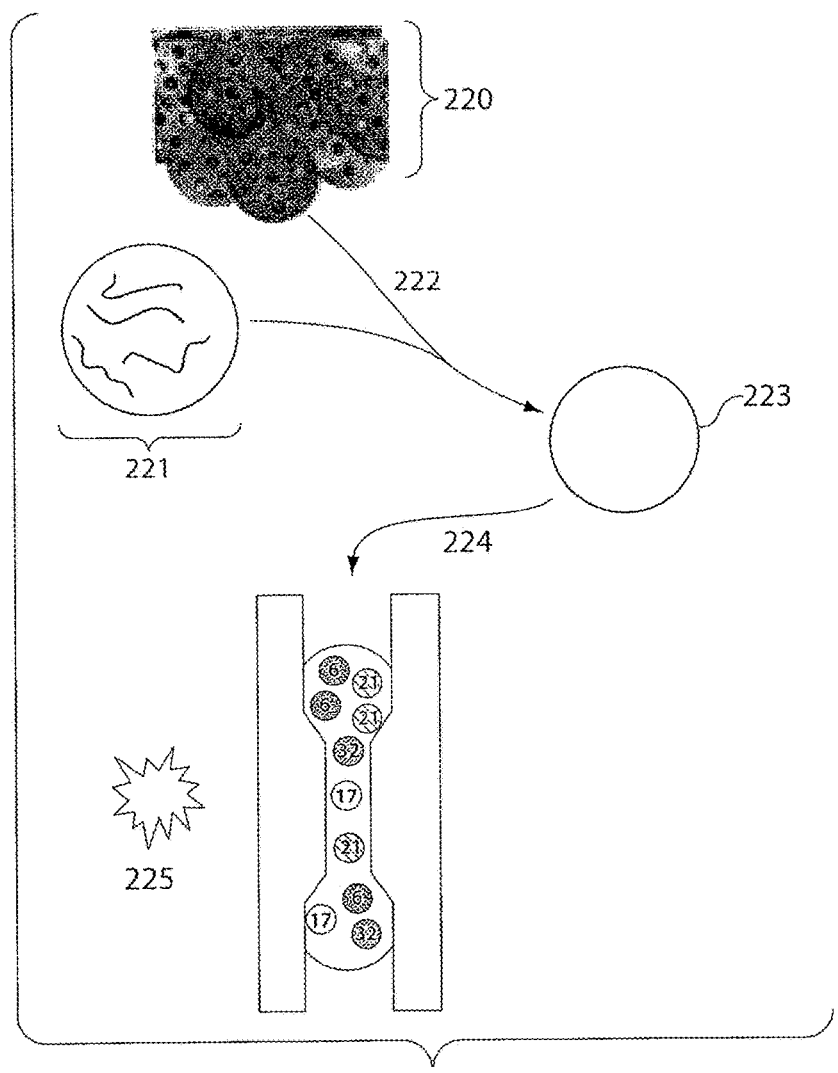
Figure 8F:
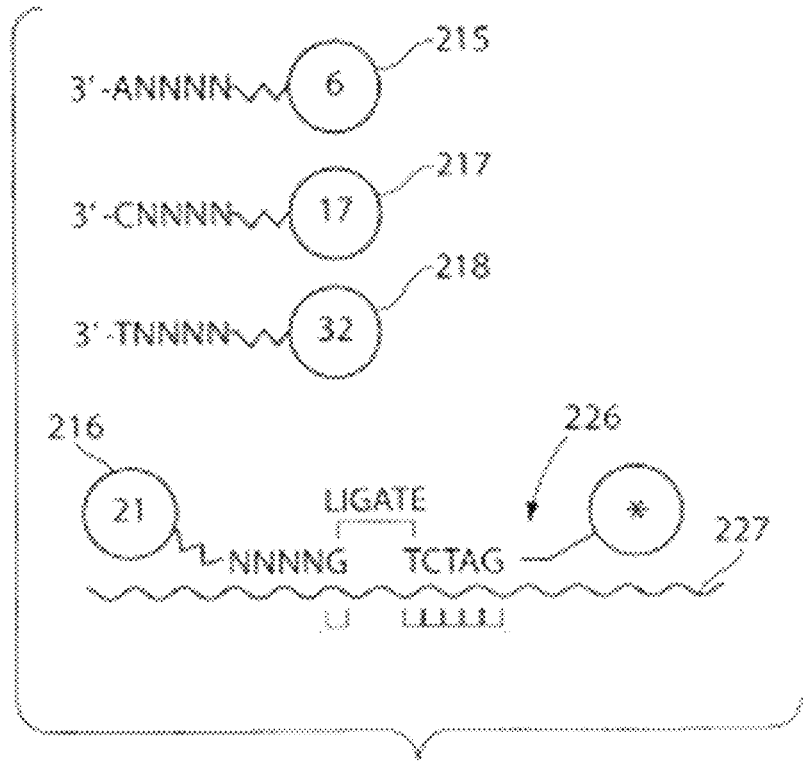

The association of the target nucleic acid and the nucleic acid probe is determined in this example as follows, although other techniques may be used in other cases. Solutions containing the nucleic acid probe and the beads can be each emulsified separately, and the emulsions are then pooled to create a collection of analytical droplets 220. All droplets will have a single bead taken from each of the 4 sets (but multiple copies of that bead may be present). The nucleic acid probes and beads can then be encapsulated together in droplets. Also provided is a plurality of droplets 221 containing the target nucleic acid and DNA ligase. The pooled emulsion library droplets are fused (as indicated by arrow 222) with the plurality of 221 droplets (FIG. 8E) to form a plurality of fused droplets 223. The fused droplets 223, as indicated by arrow 224, are passed by a detector 225. The template-directed ligation of the nucleic acid probe will cause a bead to become associated with the target nucleic acid, if both the nucleic acid probe and the oligonucleotide on the bead are adjacent to each other and complementary to the target nucleic acid. As the four beads contain universal nucleic acid residues in all but one position, only one of the four beads will be able to be positioned adjacent the target nucleic acid and the nucleic acid probe, such that ligation of the oligonucleotide on the bead to the nucleic acid probe occurs, as is shown in FIG. 8F.

Association of the bead, the target nucleic acid, and the nucleic acid probe can then be determined using any suitable technique. For example, as shown in FIG. 8F, a droplet is provided that contains the four beads mentioned above (215, 216, 217, and 218) as well as a nucleic acid probe 226 and a target nucleic acid 227. If the sequence of the nucleic acid probe is complementary to a sequence in the target nucleic acid, the nucleic acid probe will associate with the target nucleic acid. One of the four beads also comprises an oligonucleotide that can be ligated to the sequence of the nucleic acid probe if adjacently positioned, as is shown in FIG. 8F (216 in this figure); the other sequences (215, 217, and 218) cannot be adjacently positioned due to a nucleotide mismatch in the sequence. Nucleic acid probe 216 can become ligated to the oligonucleotide of the bead associated with the target nucleic acid probe, and thus, the oligonucleotide of bead 216 is able to associate with target nucleic acid 227 adjacent to the nucleic acid probe 226.

The beads are decoded as they pass through the channel constriction in single file, and the amount of label nucleic acid probe ligated (i.e., attached) onto the bead quantified. As shown in this example, example, a "G"-digit bead (bead 21) 216, is associated with the nucleic acid probe 226 which indicates that the sequence complimentary to the target nucleic acid is 5'-GATCTGNNNN-3' (SEQ ID NO: 3, and the target nucleic acid thus contains the sequence 5'-CATATC-3' (SEQ ID NO: 4).

Figure 8G:
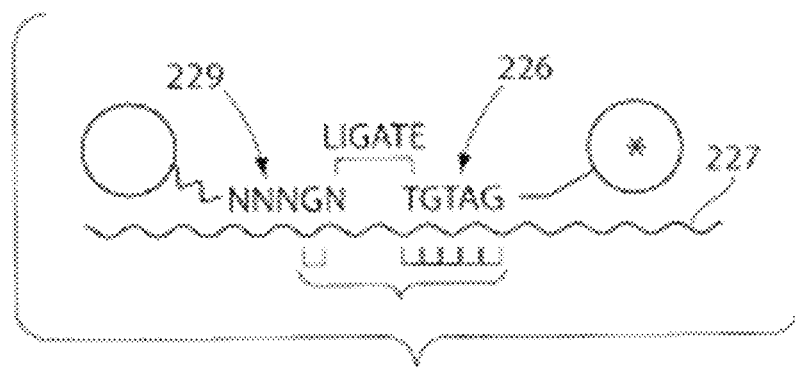

As discussed above, the differing residue of the oligo-nucleotides associated with the beads may be located in other positions as well in other embodiments, such as the second position from the 5' end of the oligonucleotide, for example, 5'-NXN$_{(n-2)}$-3'. An example of this is shown in FIG. 8G. In this example, identification element 229 comprises a bead and an oligonucleotide having a sequence 5'-NGNNN-3'. Three other identification elements comprising oligonucleoties (5'-NCNNN-3', 5'-NANNN-3', 5'-NTNNN-3') attached to distinguishable beads would also be present in the droplet. In this example, identification element 229 is associated with the target nucleic acid 227 of nucleic acid probe 226. The identification element and the nucleic acid probe can be ligated, similar to the embodiment described above. The beads may be decoded as discussed above and indicate the sequence complementary to the target nucleic acid is 5'-GATCTNGNNN-3' (SEQ ID NO: 5), and the target nucleic acid contains the sequence 5'-CXACATC (SEQ ID NO: 6) (N being a universal base, X being any one of A, C, G or T).

EXAMPLE 4

In some, but not all embodiments, all components of the systems and methods described herein are microfluidic. Examples of instrumental set-up for detection are given here.

Figure 9A:
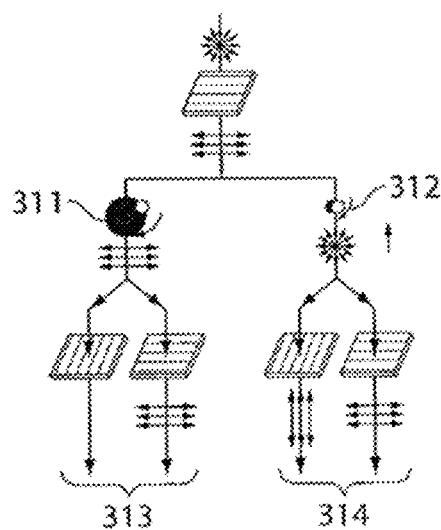
FIGS. 9A-9C depict information about fluorescence polarization (FP) detection in some embodiments of the invention.
Figure 9B:
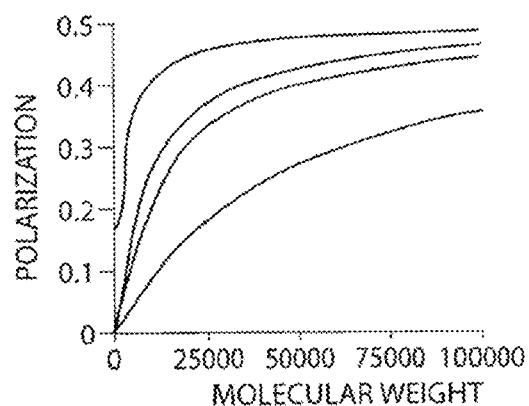
Figure 9C:
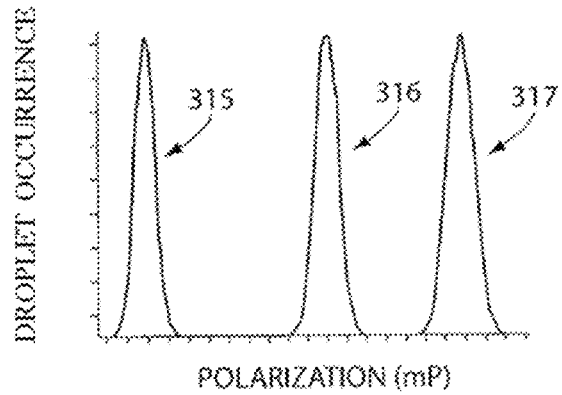

The instrument comprises in this example an optical train that may be configured to measure both fluorescence intensity and fluorescence polarization. FIG. 9 depicts information about the fluorescence polarization (FP) detection. An optical train is a series of mirrors, lenses and prisms and the like in an optical apparatus. In some embodiments, the optical train may include 3 lasers, about 5 detectors and can measure about 1000 or more fluorophores within a 30 µm droplet. If a fluorescent molecule is excited with polarized light, it will emit light of substantially the same polarization, assuming the molecule does not rotate significantly during its emission lifetime. Depolarization, or a decrease in light being emitted in the same polarization direction, occurs when the molecule rotates during its emission lifetime. Dyes attached to larger molecules 311 (and exhibiting longer tumbling time) will depolarize the light slower than the free dye in solution, and therefore, the light will remain polarized 313, as shown in FIG. 9A. On the other hand, dyes attached to smaller molecules 312 will depolarize the light faster than the free dye in solution, and therefore, the light 314 will no longer be polarized. FIG. 9B illustrates that different dyes will exhibit different polarization dependent on their fluorescence lifetime. FP is also affected by the molecular weight of the molecule to which the dye is attached. FIG. 9C illustrates this and shows the FP of free fluorescein dye 315, fluorescein-labeled 20-mer oligonucleotide 316, and fluorescein-labeled 20-mer oligonucleotides hybridized to a second DNA molecule 317. In this specific case, the tumbling rate may be reduced due to residue-stacking.

EXAMPLE 5

Figure 10:
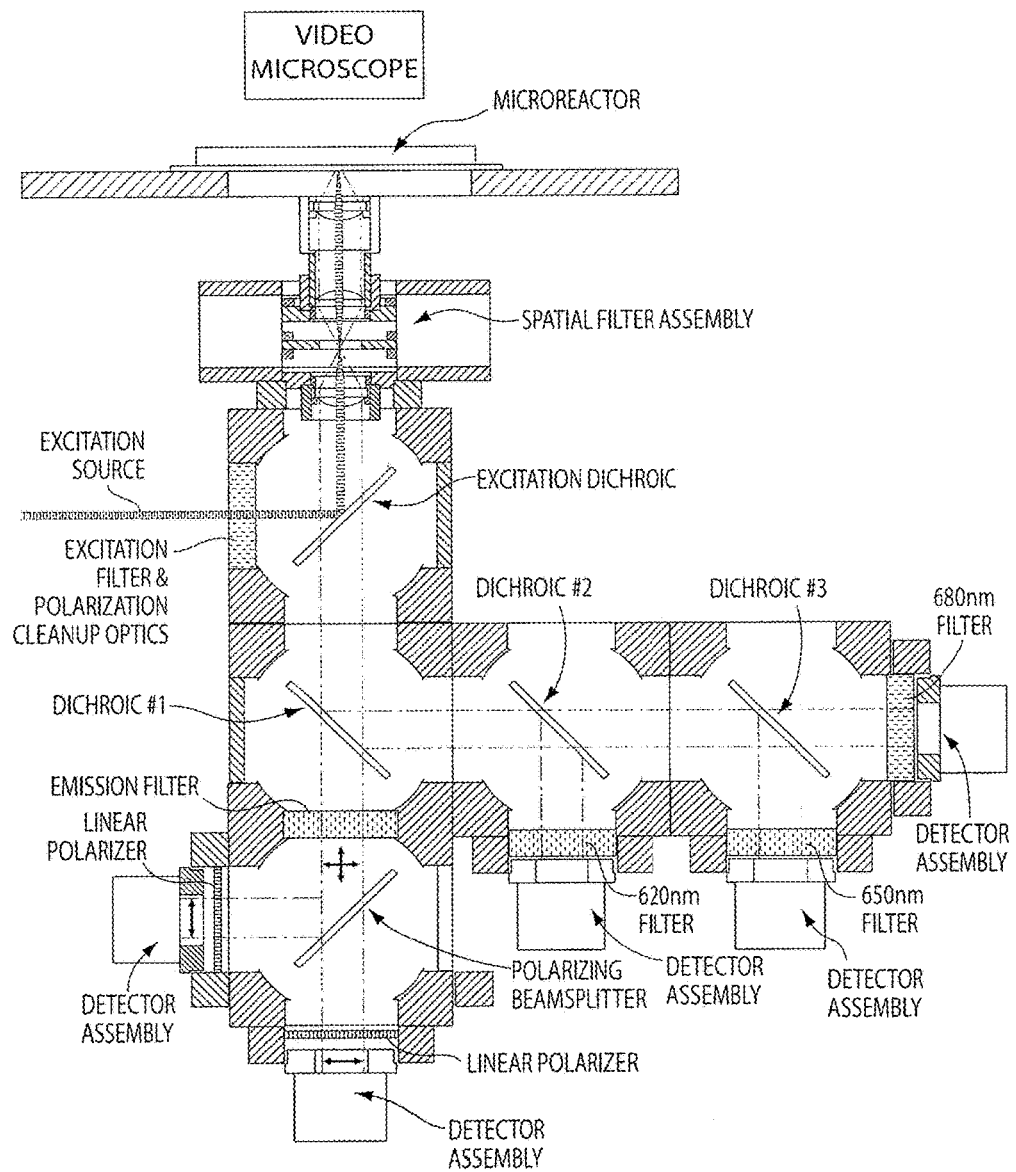
FIG. 10 shows a non-limiting example of an experiment set-up in one embodiment of the invention.

This example illustrates instrumentation for analyzing and decoding at least four different colored beads and dye fluorescence polarization (FP) and/or fluorescence intensity (FI) in a single droplet as it passes through a channel, in one embodiment of the invention. Lasers may be purchased from several manufacturers, including Power Technology, Inc. (Alexander, Ark.). An example optical train is shown in FIG. 10. This optical train is modular fashion and the filters and lasers can be exchanged when needed. This example configuration, with 5 detectors, is able to read FP at two different emissions wavelengths. The instrument will be able to measure FP on 3 channels. The stage upon which the PDMS chips sit is heated.

Figure 11:
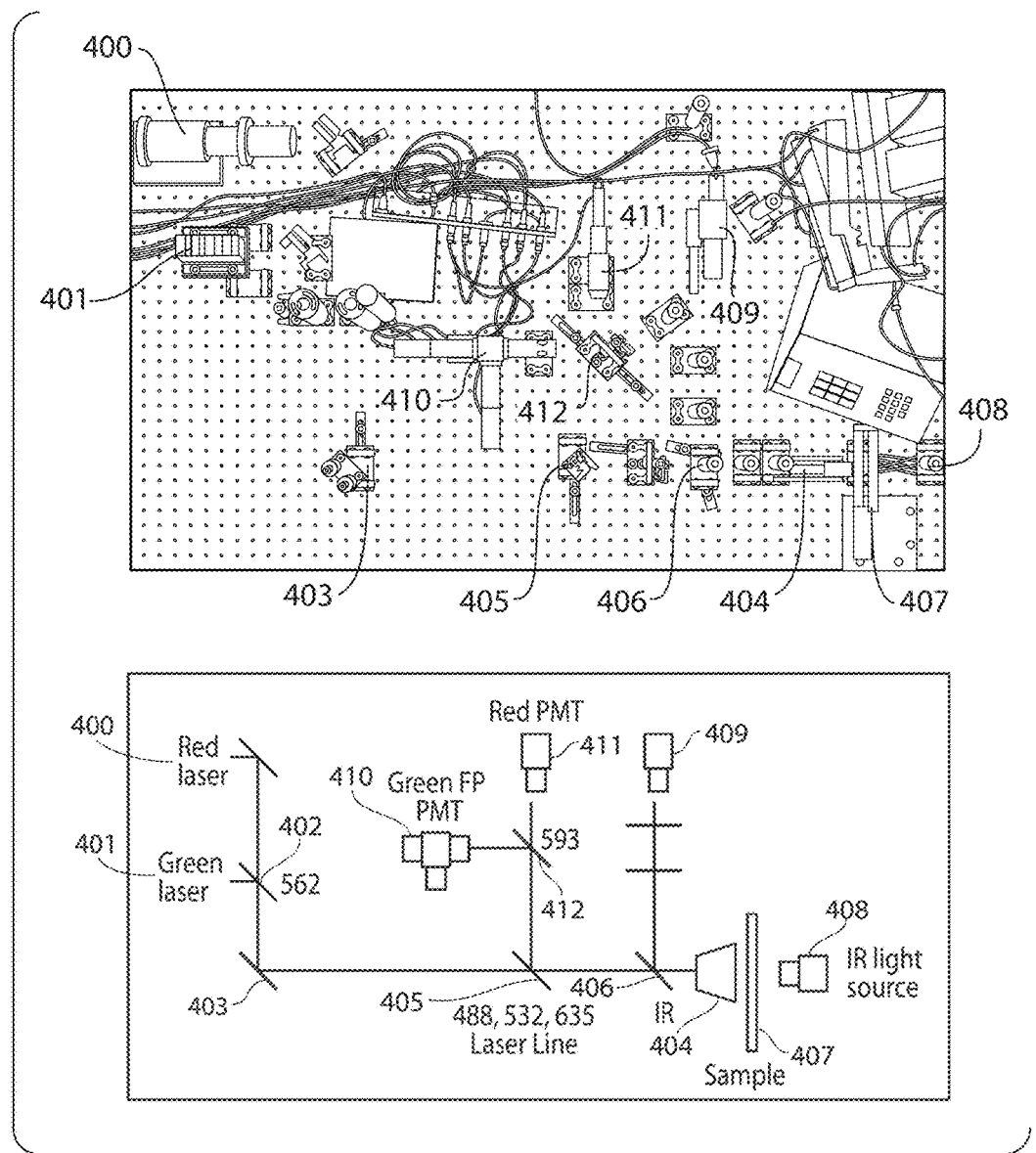
FIG. 11 shows a non-limiting example of an experiment set-up in another embodiment of the invention.

In this figure, the excitation sources used are lasers, which can include multiple lasers of different color that are shined as parallel rays. The excitation is bounced off a dichroic laser-line mirror that reflects the laser wavelengths but lets pass all other wavelengths. The lasers can be expanded, by passing through a telescoping lens combination, or can be turned into a laser line by passing through a cylindrical lens. They are then focused down through a lens with a high numerical aperture into a tight spot. The high numerical aperture ensures that a large solid-angle of fluorescent light emitted by the sample is captured in the reverse direction by the objective. The fluorescent light then passes through the dichroics and the various wavelengths are reflected off into the detector assemblies, as shown in the diagram, and according to the particular fluorophores and filters that are used. The polarizing beamsplitter is necessary for measurements of fluorescence polarization. It reflects one polarization (S) and passes the other (P). The intensity of each is then measured using a separate PMT. The values are then combined to calculate the fluorescence polarization, according to the formula $(S-G*P)/(S+G*P)$, where G is the G-factor and is usually 1. To produce a number in units of [mP] the result of the above calculation is multiplied by 1000. Typical FP values range between about 20 and about 1000 mP. The detector assemblies can be PMTs, diodes, or avalanche diodes. The signals are also monitored using a computer with an NI FPGA card running custom code written in LabVIEW. The assembly in FIG. 11 is similar, but arrayed on an optical table. In this embodiment, a temperature gradient may be required to optimize the FP. This may be accomplished by placing a Peltier device under the device stage to control temperature. In one embodiment, the experiments will be run at a frequency of 1 kHz (1,000 droplets per second) and collect data at GHz frequency. In another embodiment, sensitivity of the detection may be increased by choosing different PMT, choosing beads with higher dye concentrations, and/or increase the amount of dye label in the droplets. In some instances, the device may comprise widened channels and/or use hydrodynamic focusing to prevent bead clogging. The constrictions can also be redundant on a chip in some cases such that if one gets clogged a second constriction will become operable.

A specific instrumentation configuration depicting a fluorescence stand and droplet monitor is given in FIG. 11. Lasers are located in the top left. A red laser 400 (30 mW 635 nm) is used to drive the Cy5™ fluorescence. A green laser 401 (125 mW 532 nm) is used to drive HEX fluorescence. The beams are brought parallel using a 562 dichroic mirror 402 that reflects everything below 562 nm (Semrock® Brightline FF562-Di02-25×36). The beams bounce off the mirror 403 at the bottom left into the optics 404 on the bottom right. The light goes through a 488/532/638 laserline dichroic mirror 405 (Semrock® Brightline Di01T488/532/638-25×36×5.0) which allow for the wavelengths near these to pass and for the reflection of all other wavelengths. The beams then go through an IR hot-mirror 406 (Edmund Optics NT43-955) that reflects IR and lets other wavelengths pass. Then they go into the back of the objective (Mitotuyo Plan APO, 5×, 10×, 20×, or 50×) and are focused down onto the sample. In some cases, the larger the magnification, the more sensitive the detection. This is believed to be because higher magnification objectives have higher numerical aperture, and therefore capture a larger solid-angle of light emitted from the sample. The sample 407 is mounted on an XYZ translation stage with 2 inches (50.8 mm) of travel (Thorlabs). There are two imaging paths which run in reverse. Fluorescence imaging uses the lasers as a light source. Direct imaging is done using infra-red illumination which allows an image to be taken while capturing fluorescence data. The IR light source 408 is an IR-diode (Digikey) focused through a 15 mm lens (Thorlabs, LA1222). The IR and fluorescence beams then travel back through the objective. The IR is reflected off the IR mirror 406 up into a CCD camera 409 (Sony XCD-V50, upper right). The fluorescence passes through the IR mirror to the laserline dichroic where it is reflected into the detection PMTs (Hamamatsu H5784-20, center of image). A green FP PMT 410 and a red PMT 411 are both present. The IP detector and camera are used to visualize the droplets. It can also be used to monitor the end and beginning of different template droplets. There is a 593 nm high pass dichroic 412 (Semrock® Brightline FF593-Di02-25×36) that reflects the HEX signal into the FP detector setup. It allows the Cy5™ signal (~680 nm) to pass into the Cy5™ channel PMT. The FP detector (T-shaped object in center of image) includes two PMTs mounted perpendicularly to one another into a 50-50 beamsplitter (Thorlabs CM1-BS1). Mounted in front of the beamsplitter is a 560/25 bandpass filter (Semrock® Brightline FF01-560/25-25). Mounted in front of each PMT is a polarizer (Meadowlark Optics DPM-100-VIS1) and an f=25 mm lens (Thorlabs LA1951). The PMTs are mounted on rotary cage mounts (Thorlabs CRM1) so that they can be rotated at 90 degrees with respect to one another.

In this specific example, the machine uses a 532 nm green laser to excite the signaling entities and a 635 nm diode laser to excite the red and near infrared fluorescence from the dyes used to color code the beads. In another example, when employing Luminex® beads as the identification elements and nucleic acid probes labeled with hexachlorofluorescein (HEX), the instrument may be configured to read FP on a HEX channel (~560 nm) to determine whether a nucleic acid probe is bound to the target nucleic acid and the FI may be read by both a HEX and Cy5™ channel (~690 nm).

The PMT data may be digitalized and the digital signals are analyzed by a National Instrument field-programmable gate array (NI-FPGA) card. This gate array may be programmed to capture and analyze data at hundreds of kilohertz simultaneously and/or on multiple channels. The FPGA card may be programmed to determine droplets, as the droplets appear as peaks as they flow past the laser. As a drop is determined, throughout the duration the droplet is in front of the detector, the maximum intensity, and/or its time-integral for each color channel can be monitored in some cases. Such measurements can then be combined to determine the identification element and the fluorescence polarization of the nucleic acid probe (e.g., due to signaling entity) associated with the target nucleic acid.

The microfluidic chip may be placed on a heated stage that allows multiple zones of heating. A two-temperature-cycle PCR may be performed on-chip by cycling the reactions in aqueous droplets down a channel that serpentines between hot (e.g. 95° C.) and warm zones (e.g. 65-72° C.) on the chip.

The PMT signals are input into a National Instrument connector block mounted inside of a CA-1000 connection assembly. The connector block bundles the PMT signals into a single cable that is plugged into a National Instrument compact FPGA card. The card may be installed on a PC running Windows XP. Data can be captured and analyzed using software developed in the LabVIEW programming environment.

Microsphere fluorescence in bulk may be measured using Luminex® Lab MAP hardware and software (Luminex® Corp., Austin, Tex.). Green fluorescence measurements may be converted to molecules of equivalent soluble fluorochrome (MESF) using Quantum Fluorescence Kit for MESF unit of FITC calibration particles and QuickCal software (all from Sigma, St. Louis, Mo.). Green fluorescence contributed by the microspheres alone will be subtracted from all data points. In droplet measurements of bead fluorescence and probe attachment will use the instrumentation described above.

EXAMPLE 6

Figure 12A:
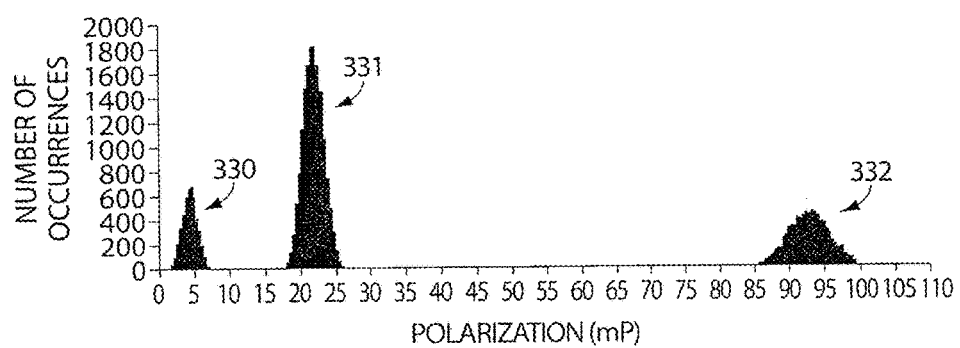
FIGS. 12A-12B show examples of employing liquid labels as identification elements.
Figure 12B:
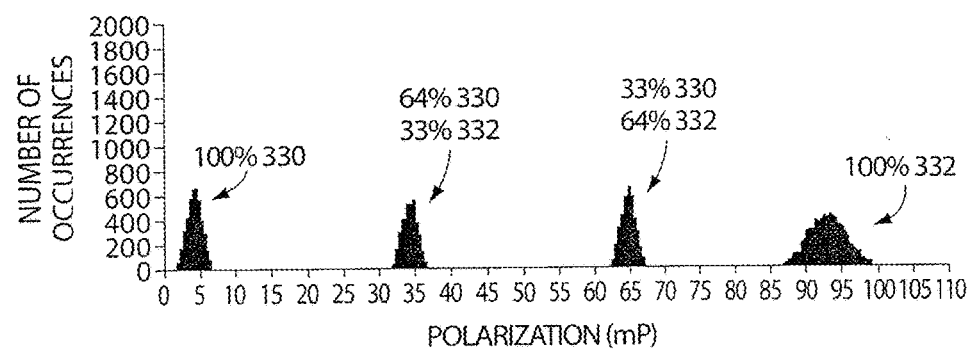

This example illustrates the preparation of a plurality of distinguishable fluorescent beads, similar to the commercially-available Luminex® beads (5.6 um in diameter). FP may be independent of dye concentration (for example, a 1 M concentration of fluorescein has an identical FP as a 0.01 M) and may be treated as an independent variable in labeling. Therefore, if a single dye is varied in 10 units in two dimensions, it can be used to generate 100 dye labels. Therefore, with 2 dyes, 10,000 labels may be generated. FIG. 12 shows the FP of a dye can be varied by attaching it to a larger molecule. FIG. 12A shows the FP of fluorescein 330, biotin 331 and biotin+streptavidin 332. FIG. 12B shows that by varying the relative concentration of the two different compounds, the total FP value can be controllable changed. It is important to note that the FP may be controlled independent of the concentration of the fluorophore.

Figure 13A:
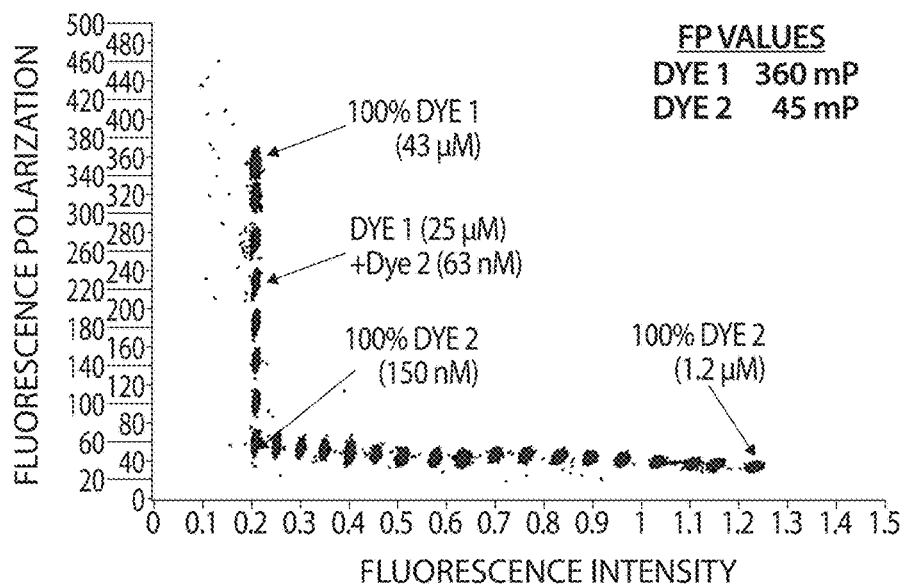
FIGS. 13A-13B illustrate that fluorescence intensity and fluorescence polarization may be independently controlled in certain embodiments.
Figure 13B:
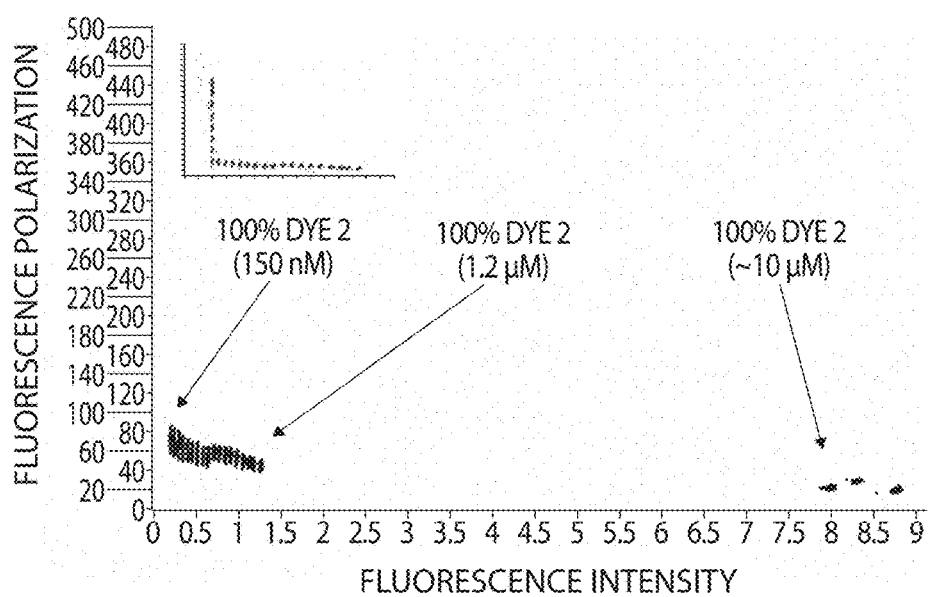

FIG. 13 shows that the fluorescence intensity (FI) and the FP can be independently controlled. Therefore, expanding the range of dye concentration and droplet FP value allows the generation of many identification elements. FIG. 13A show the results when mixing two dyes with overlapping emission spectra and each having a different FP. The two dyes are mixed in varying ratios to give varying FP values, and varying total dye concentration to yield varying FI. FIG. 13B shows a relatively broad concentration range indicating a wide span in which to vary the total FI. This figure encompasses a 10-fold increase in the total dye concentration shown in FIG. 13A.

EXAMPLE 7

The identification elements, in some cases, may be polystyrene beads of sizes ranging from approximately 10 nm to 100 um in diameter, and the beads may be dyed. As an example, the dyes employed can be squaric acid-based molecules that exhibit fluorescence extending into near infrared and/or infrared region. This can allow for reproducible processes in which two or more dyes of independent concentration are absorbed uniformly into each bead, resulting in multiple fluorescent signals respective of the number of dyes present in the bead. To make a population of beads with different fluorescent characteristics, in this example, the ratio of red:orange dyes can be altered by an adequate increment in proportion of dyes so that obtained population optically does not overlap with the former population. For example, there may be a relationship between two dye concentrations in a given population of beads and location of said populations on an X-Y map. Each location may be assigned in terms of a first color (FL3) or of a second color (FL2) dyes intensity as expressed in linear fluorescence channels units. As the beads move vertically up a column, both the first color and the second color dye amounts in a bead can be increased. This may be due to an energy transfer from one dye to the other dye. When moving horizontally from left to right across a row, one dye can be decreased in order to maintain a steady FL3 value. This may be due to overlap of one dye spectrum into the other dye region. Using this method, multiple, non-overlapping populations of beads can be constructed. Two parameters, a fluorescent color and color intensity or brightness (expressed in fluorescence channel units), can be employed to classify the beads.

EXAMPLE 8

This example illustrates template DNA preparation, according to one embodiment. In this example, DNA fragmentation is performed using a modified Aeromist Nebulizer (Alliance Medical, Russellville, Mo.). The size distribution of the nebulized fragments can be determined by resolving a 2 uL aliquot of the nebulized material on an Agilent 2100 BioAnalyzer (Agilent, Palo Alto, Calif.) using a DNA 1000 LabChip.

DNA nebulization generated fragments with a preponderance of frayed ends. Fragments may be blunt-ended and phosphorylated through the activity of various enzymes, such as T4 DNA polymerase, E. coli DNA polymerase (Klenow fragment) (NEB, Beverly, Mass.) and T4 polynucleotide kinase (NEB). The polishing reaction may be purified over a QIAquick® PCR Purification column.

Following fragmentation and polishing of the genomic DNA library, primer sequence can be added to each end of the DNA fragments. The 44-base primer sequences ("adaptors") are double-stranded oligonucleotides comprising a 5' 20 base PCR amplification primer followed by a 20 base sequencing primer. Two classes of adaptors, adaptor A and adaptor B, can be used in each reaction. The A and B adaptors differ in both nucleotide sequence and the presence of a 5' biotin tag on the B adaptor. The adaptor pairs are be designed to allow directional ligation to the blunt-ended, fragmented genomic DNA.

For example, adaptor A may be CCATCTCATCCCT-GCGTGTCCCATCTGTTCCCTCCCTGTCTCAG (SEQ ID NO: 7) and adaptor B may be 5BiotinTEG/CCTATC-CCCTGTGTGCCTTGCCTATCCCCTGTTGCGT-GTCTCAG (SEQ ID NO: 8). For each adaptor pair, the PCR priming region contains a 5' four-base overhang and a blunt-ended 3' region. Directionality will be achieved as the 3' blunt-end side of the adaptor ligated to the blunt-ended genomic DNA fragment while the 5' overhang prevents ligation to the PCR primer region of the adaptor. A 2% agarose (Invitrogen, Carlsbad, Calif.)/TBE slab gel with 4.5 uL of a 10 mg/mL stock of Ethidium Bromide (Fisher Scientific, Pittsburgh, Pa.) can be used for gel purification. The two nicks at the 3'-junctions can be repaired by the strand-displacement activity of Bst DNA polymerase, Large Fragment. Stock M-270 Streptavidin beads (Dynal, Oslo, Norway) may be used to isolate AB-linkered fragments. The single-stranded library will be concentrated over a single column from a MinElute® PCR Purification Kit (Qiagen) which has been warmed to room temperature prior to use.

EXAMPLE 9

This example illustrates the preparation of collection of droplets, in one embodiment of the invention. In this example, Luminex® beads are coated with a reagent specific to a particular bioassay, allowing the capture and detection of specific analytes from a sample. Lasers excited the internal dyes that identify each bead, and also any signaling entity during the assay.

Carboxylated microspheres (5×10$^6$, 400 uL) are coupled to the nucleic acid probes according to the Luminex® (the bead manufacturer) recommendations. Coupling reaction success may be assessed by hybridizing coupled microspheres with a molar excess of biotinylated oligonucleotide complementary to the bead bound sequence. Effective coupling produces microspheres with a mean fluorescent intensity (MFI) to 2000-4000 U. Microspheres with MFIs less than 1000 can be replaced in some cases, such that the microspheres that are used have good intensities.

As an example for the preparation of a collection of analytical droplets, the appropriately-tagged beads can be suspended in 96 well plates such that each well will contain a set of four beads, where each bead is distinguishable from the other beads (although multiple, identical copies of each bead may be present). Each well will have added to it a nucleic acid probe selected from a library of nucleic acid probes. The nucleic acid probe may be labeled. The contents of each well will be separately used to make an emulsion of 30 micron droplets. Each of the resulting aqueous droplets in each emulsion will contain 3-4 beads of each of the four distinguishable beads and the labeled nucleic acid probe at varying concentrations, e.g., 10-100 uM. The emulsification may be completed for each individual well. When the entire collection of wells has been emulsified, the droplets will be pooled together to create a collection of analytical droplets. The collection can be stored for any suitable period, e.g., ranging from less than one hour to many months.

EXAMPLE 10

Figure 14:
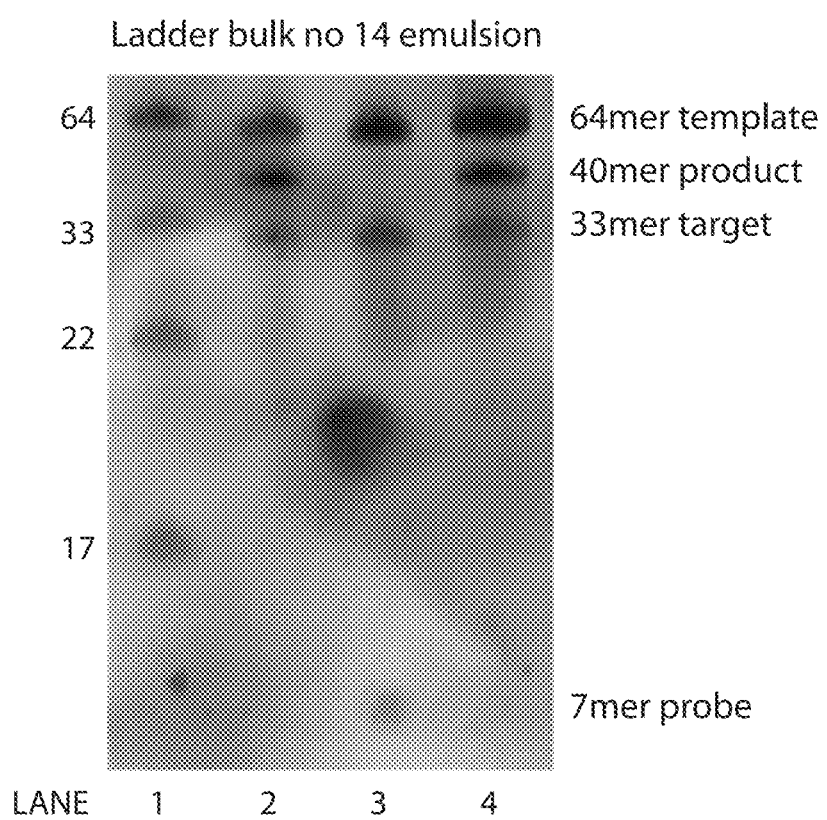
FIG. 14 shows an example of ligation of DNA occurring within droplets, in one embodiment of the invention.

Ligation of DNA can occur within droplets in some embodiments of the invention. This is an example illustration such ligation. In this example, the co-flow of template DNA+33mer+phosphorylated 7mer in the presence (lane 3) and absence (lane 4) of T4 DNA ligase is depicted in FIG. 14. The aqueous phase was loaded onto a polyacrylamide gel. Ligation of the 7mer to the 33mer, resulting in a 40mer, occurred within the droplet. To prevent ligase activity prior to droplet merging, the ATP co-factor may be sequestered from active enzyme. The ATP for the ligation reaction may be included in the template droplets. The T4 DNA ligase may be included in the collection of analytical droplets. Therefore, only when the DNA template and the collection of analytical droplets is merged, will the ligase become active Templated (double-stranded PCR products, 250-450 base pairs in length) can be used at a 3-20 ng/ml concentration. Green fluorescent signals have been observed through this concentration range. Identification elements comprising nucleic acid oligonucleotides can be used in the 10 nM range and the ratio of those elements to the nucleic acid probes may be 1:50. The ligation of the identification elements comprising nucleic acid oligonucleotides to DNA-coupled microspheres may have a minimum of 30 minutes of incubation.

To avoid a potential source of background fluorescence formed from sandwich complexes which are non-ligated, ZipCode-hybridized complexes, the background fluorescence may be determined in the absence of ligase. Incubating the microsphere suspension at 45° C. for a minimum of 15 minutes just prior to flow analysis minimizes background fluorescence.

Figure 15:
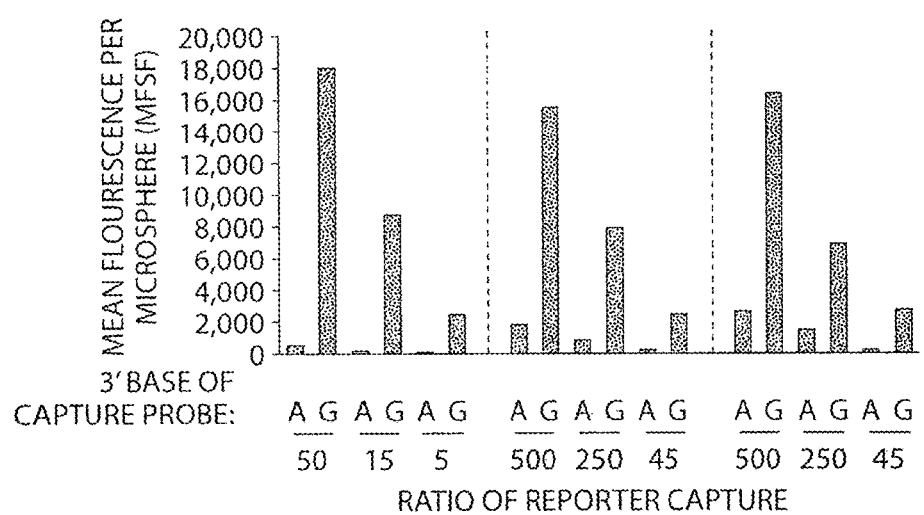
FIG. 15 shows results of a ligation assay using labeled nucleic acid probes according to another embodiment.

Ligation assays have been tested using a labeled nucleic acid probe. An 8-bases sequence was tested that contained either zero or two degenerate sites. A short 8-based oligonucleotide (CTAAGTTA (SEQ ID NO: 9)) was designed for single nucleotide polymorphism (SNP) analysis using the standard ligations assay reaction. SNP is a DNA sequence variation occurring when a single nucleotide in the genome differs between members of a species. The ligation assay was condued using PCR-amplified homozygous target DNA (previously genotyped by RFLP analysis as GG) for SNP1 (an A, G polymorphism). For the match condition, the ligation probe was designed to be complementary to the 25 bases of the target DNA up to and including the single base to be queried. As shown in FIG. 15A, the 8-base nucleic acid probe (CTAAGTTA (SEQ ID NO: 9)) successfully identified with the GC homozygous target DNA. The signal intensity from the 8-base probe was 65% of that observed with an 18-base probe. As shown in FIGS. 15B and 15C, both degenerate oligonucleotide (CTNAGNTA (SEQ ID NO: 10) and CTANNTTA (SEQ ID NO: 11) respectively, (where N is universal base) correctly identified the SNP genotype of the target DNA. Each probe contained a 5' $PO_4$ and a 3' fluorescein. The ratio of ligation probe to nucleic acid probe refers to the molar ratio of the two probes added prior to the ligation assay. To compensate for the 16-fold reduction in concentration of the correct, 5'-CTAAGTTA-3' (SEQ ID NO: 9) nucleic acid probe, the degenerate nucleic acid probes were used at 16-fold higher concentration than the non-degenerate sequence.

EXAMPLE 11

The following example describes the determination of hybridization of nucleic acid probes to a target nucleic acid using a library of droplets comprising distinguishable nucleic acid probes and distinguishable identification elements.

In a first example, four emulsions were created and mixed, with each emulsion containing at least one dye. This example was used to determine the signal from a plurality of droplets. The emulsions were created as follows. Four fluids were first prepared by filling four reservoirs with four combinations of fluorescent dyes and DNA molecules. 20 uM of Cy5™ dye was provided in the first reservoir. 15 uM of Cy5™ dye was provided in the second reservoir. 10 uM of Cy5™ dye, with 2 uM of un-ligated nucleic acid probe A (carboxytetramethylrhodamine (TAMRA) linked 6-mer) and nucleic acid probe B (6-carboxyfluorescein (FAM) linked 9-mer) was provided to the third reservoir. Cy5™ 2 uM of ligated nucleic acid probe A (TAMRA linked 6-mer) and nucleic acid probe B (FAM linked 9-mer) were provided to the fourth reservoir. No Cy5™ dye was provided to the fourth reservoir. In this example, the four concentrations of Cy5™ dye acted as labels, while equal concentrations of ligated and unligated nucleic acid probe A and nucleic acid probe B were provided to test of the detectability of the FRET in the droplets.

The fluid from the four reservoirs were emulsified. The emulsions were created by injecting the four different solutions into four different flow focus droplet makers. Fluorocarbon oil was also injected into each droplet maker. All four devices employed were substantially identical, with flow focus dimensions of about 25×25 microns. All four fluids were injected into the devices at approximately the same rate of about 500 microliters per hour for the inner phase and about 1000 microliters per hour for the outer phase. As a result, all dropmakers produced droplets at approximately the same rate and of approximately the same size.

Figure 32:
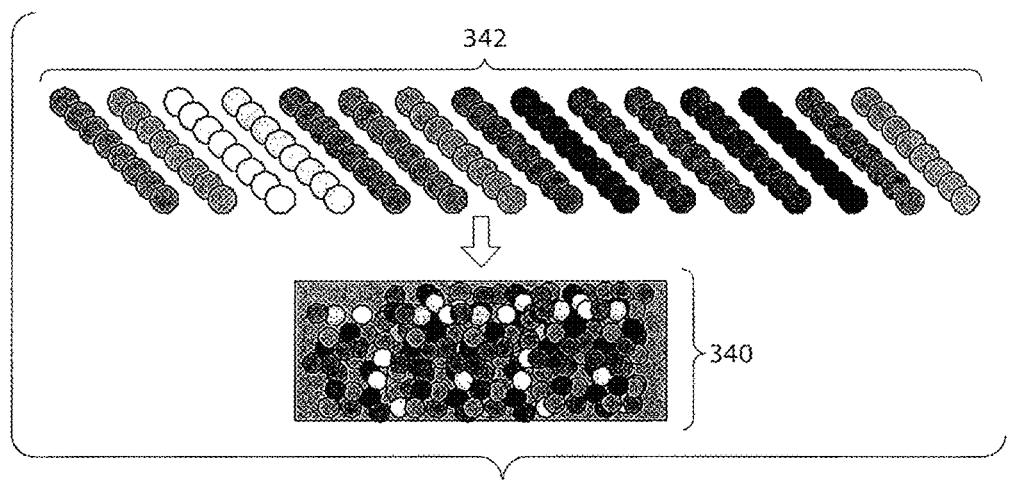
FIG. 32 shows a schematic diagram of an emulsion of droplets formed by mixing a plurality of types of droplets, according to one embodiment.

The droplets produced in each dropmaker then flowed out through a tube connected to the outlet. There were four droplet makers and four outlet tubes. The tubes were bundled together and placed into a communal syringe. As the droplets dripped out of the tubes, they were pooled into the syringe. This droplet formation proceeded for about 30 min, after which about 1 mL of droplets had been collected. Because all the droplets were emulsified at the same time, they were randomly mixed in the collection syringe. FIG. 32 shows a schematic diagram of the emulsion of droplets 340 formed by mixing a plurality of types of droplets 342, each type of droplet comprising a distinguishable nucleic acid probe, and at least one unique identification element.

Figure 31A:
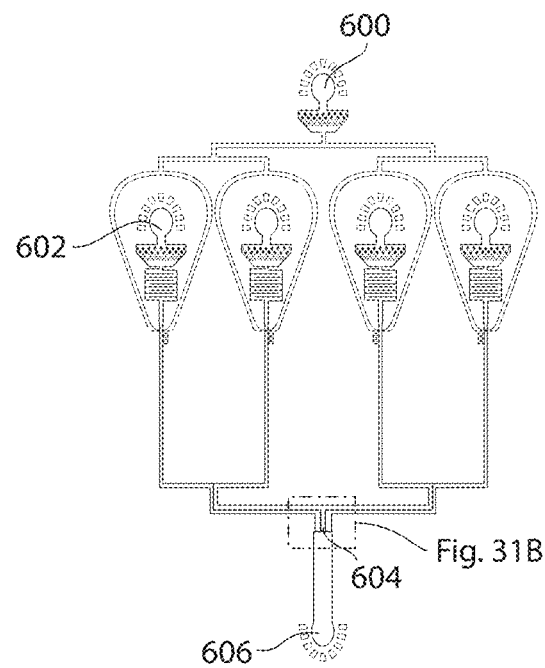
FIG. 31A shows a schematic of a microfluidic device that may be used to produce four groups of droplets comprising different concentrations of different dyes, according to one embodiment.
Figure 31B:
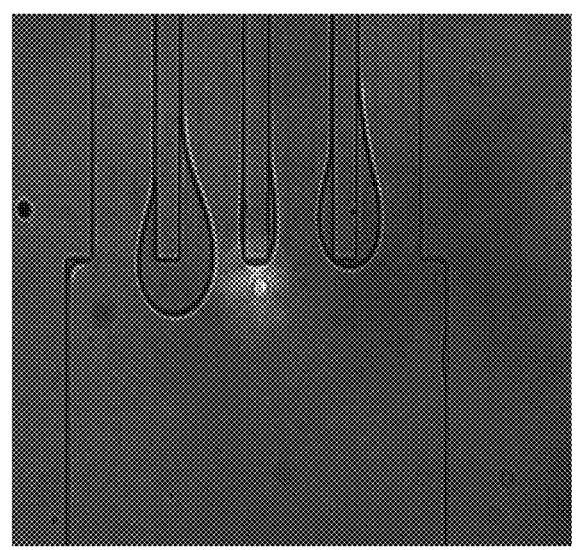
FIG. 31B shows an image of the first frame of a movie showing the production of a plurality of droplets that were formed using the device shown in FIG. 31A.

FIG. 31A shows a schematic of the microfluidic device that was used to produce in parallel the four groups of droplets, each group of droplets containing one to four different dye combinations. The upper inlet 600 allows oil to be provided to the device. The inner inlets 602 allow for the four different combinations of dye to be injected into the device. Flow focus junction 604 is where the four types of droplets are formed, with each having a unique dye combination. The droplets then flowed through a channel and are collected in a collection chamber 606. The droplets were imaged in the collection chamber before exiting the device. FIG. 31B shows an image of the first frame of a movie and of a magnified view of the collection chamber, into which the droplets flowed after being produced, but prior to exiting the device. In this frame, the droplets have not yet formed, and the channel was filled with co-flowing streams of fluorescently dyed water and fluorocarbon oil.

Figure 19:
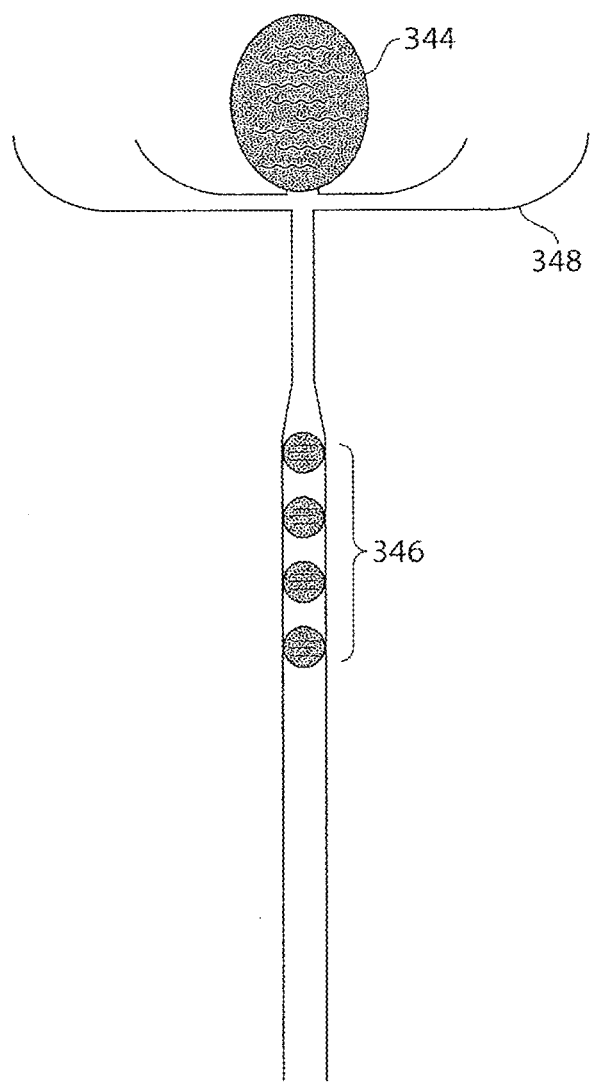
FIG. 19 illustrates a solution comprising a plurality of target nucleic acids formed into a plurality of droplets, according to one embodiment.

A plurality of droplets was formed comprising a target nucleic acid. The target nucleic acid was 5'-CGCCA-GGGTTTTCCCAGTCACGACGTTGTAAAACGACG-GCCAGTGAATCCGTAA TCATGGCCAT-3' (SEQ ID NO: 12). As shown in FIG. 19, a solution 344 comprising a plurality of target nucleic acids was formed into a plurality of droplets 346, with each comprising at least one target nucleic acid, using a microfluidic device 348.

Figure 20A:
FIGS. 20A and 20B show images of a first and a second microfluidic droplet flowed into a channel such that they merge.
Figure 20B:
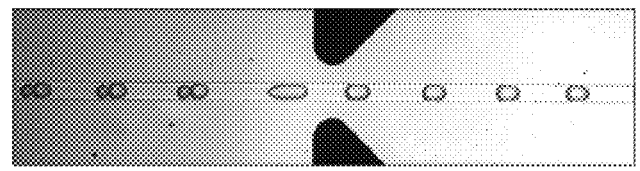
Figure 21:
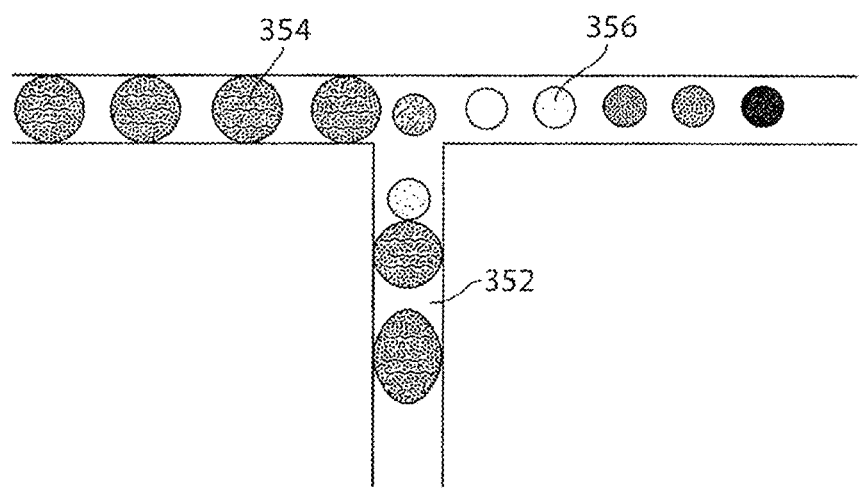
FIG. 21 shows a schematic of a process used to merge droplets, in one embodiment of the invention.
Figure 22:
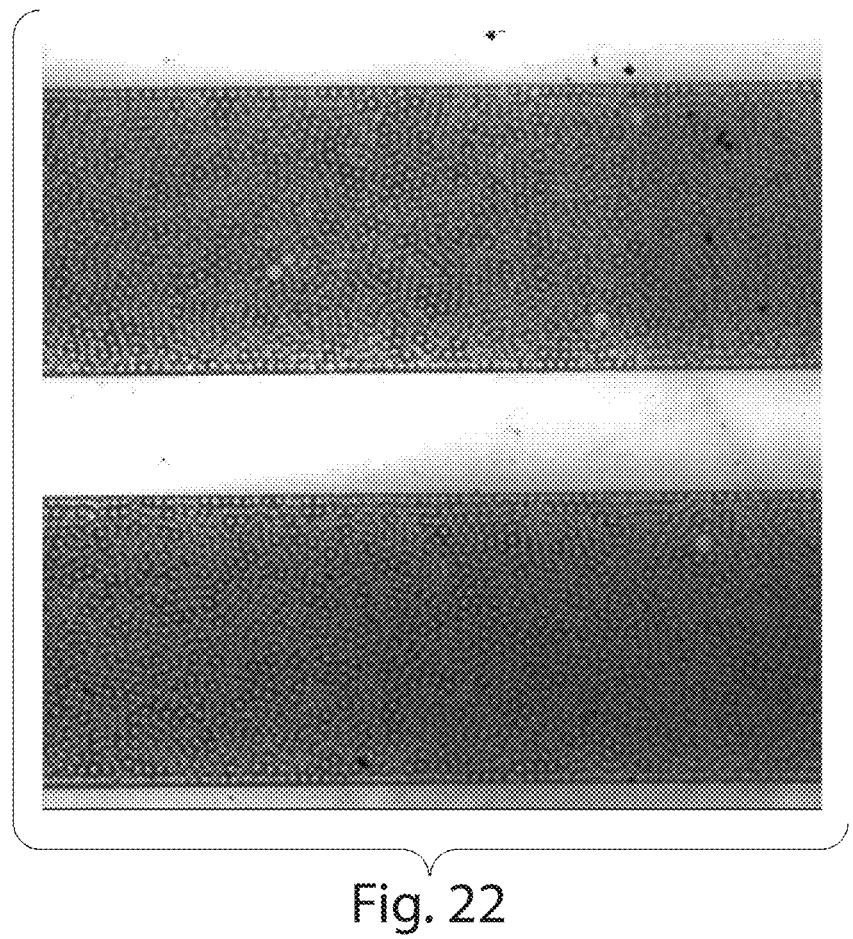
FIG. 22 shows the incubation of a plurality of fused droplets in delay lines.

The plurality of droplets comprising the target nucleic acid and the library of droplets comprising the nucleic acid probes are merged using microfluidic techniques, for example, those described in International Patent Application No. PCT/US2004/010903, filed Apr. 9, 2004, entitled "Formation and Control of Fluidic Species," and International Patent Application No. PCT/US2004/027912, filed Aug. 27, 2004, entitled "Electronic Control of Fluidic Species." As shown in FIG. 20A, the droplets comprising the nucleic acid probes were flowed into a microfluidic channel 352 such that droplet 354 comprising a target nucleic acid is adjacent to droplet 356 comprising a nucleic acid probe. FIG. 20B shows the merging of the droplets using electrocoalescence. FIG. 21 shows a schematic of the process describe in FIGS. 20A-20B. FIG. 22 shows the fused droplets were incubated in delay lines. In this example, the fused droplets were incubated for about five minutes.

Figure 23:
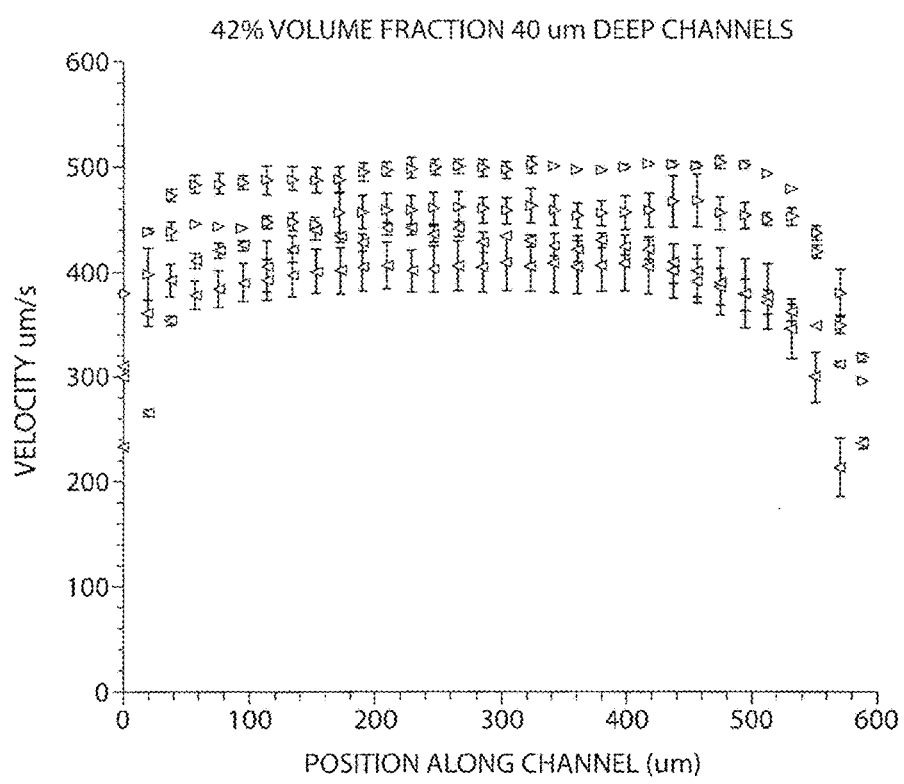
FIG. 23 shows a graph of the velocity of the fused droplets versus position along the incubation channel, according to one embodiment.

FIG. 23 shows a graph of the velocity of the fused droplets (um/s) versus position along the incubation channel. More specifically, FIG. 23 shows the velocity profile of the droplets across the channels. The y-axis shows velocity as measured using piv (particle image velocimetry), while the x-axis shows the location. In some embodiments, for Poiseuille flow in a channel of circular cross section, one might expect the velocity profile of the flow to be parabolic, due to the no-slip boundary conditions at the channel wall. In some cases, however, the flow of an emulsion into a channel may cause the fluid to flow in non-Newtonian flow and the flow profile may not be parabolic. The flow profile shows that the flow velocity across the channel was roughly constant except close to the walls. Without wishing to be bound by theory, this may occur because the droplets were produced at very high volume fraction (e.g., the percentage of water volume compared to oil volume is high). Therefore, the droplets could remain relative to one another as they flow in the channels such that the droplets flowed at approximately the same rate through the channels. This can be used to reduce the variation in incubation time between different drops.

As a non-limiting example, in some cases, the time that a droplet has to incubate is the time that it spends in the incubation channel. If the droplets are dilute, then the fluid can behave like a Newtonian fluid and the flow will be parabolic. The velocity in which a droplet moves through the channel may thus depend on the location of the droplet in the width of the channel (e.g., a droplet that is at the middle of the channel may have a faster velocity than a droplet near the edge of the channel). Therefore, the incubation time of the two droplets may differ if the flow velocity is not substantially non-parabolic. However, if the flow profile is constant, the velocities of the droplets would be approximately equal and therefore, the incubation times would be approximately equal. In some cases, the non-parabolic flow profile may be achieved for low volume fraction emulsions. For example, for a low aspect ratio channel, the spatial gradient in the flow field may be dominated by the shortest dimension. In some instances, if the channel is significantly shorter than it is wide, then the shortest dimension will be its height. This may cause the derivative of the flow profile to be very sharp, which can result in a large gradient near the walls.

Figure 24:
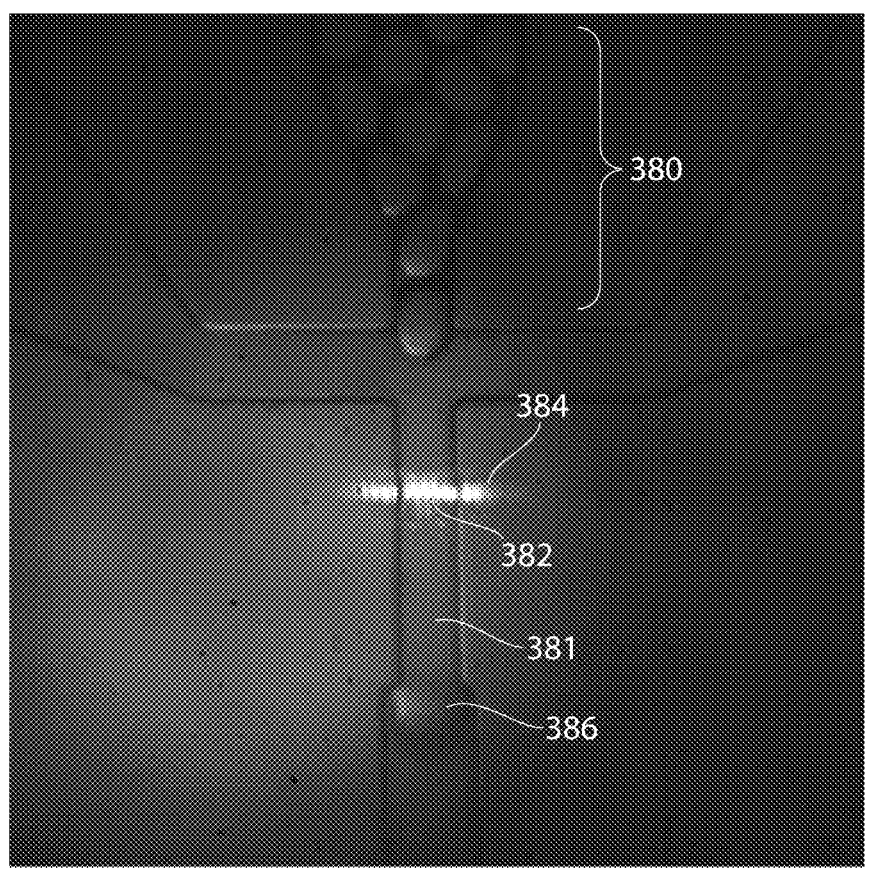
FIG. 24 shows a picture of a system that is used to determine hybridization, according to one embodiment.
Figure 25A:
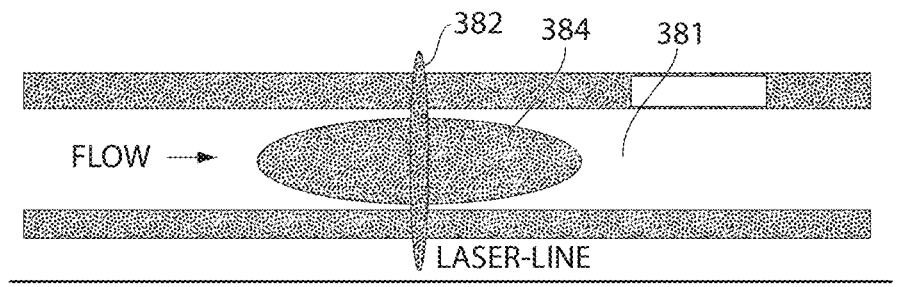
FIG. 25A shows a schematic of the system similar to the one described in FIG. 24.
Figure 25B:
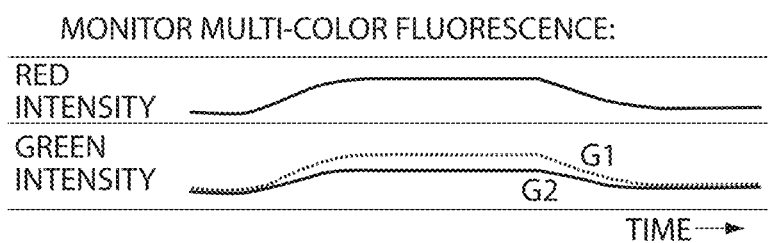
FIG. 25B shows the fluorescence polarization that may be observed when determining a droplet using a system such as the one shown in FIG. 25A.
Figure 26:
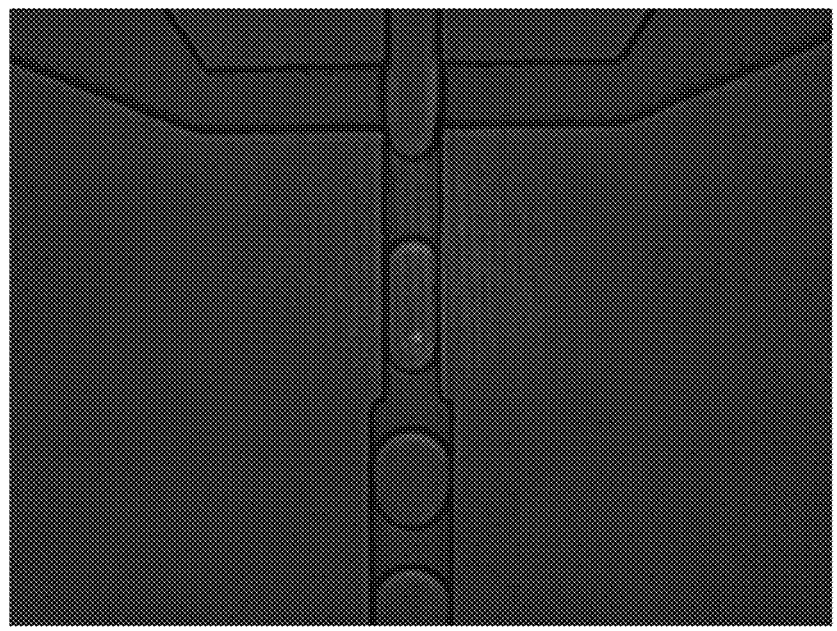
FIG. 26 shows a picture of a system in which a droplet is deformed during determination, according to one embodiment.
Figure 27A:
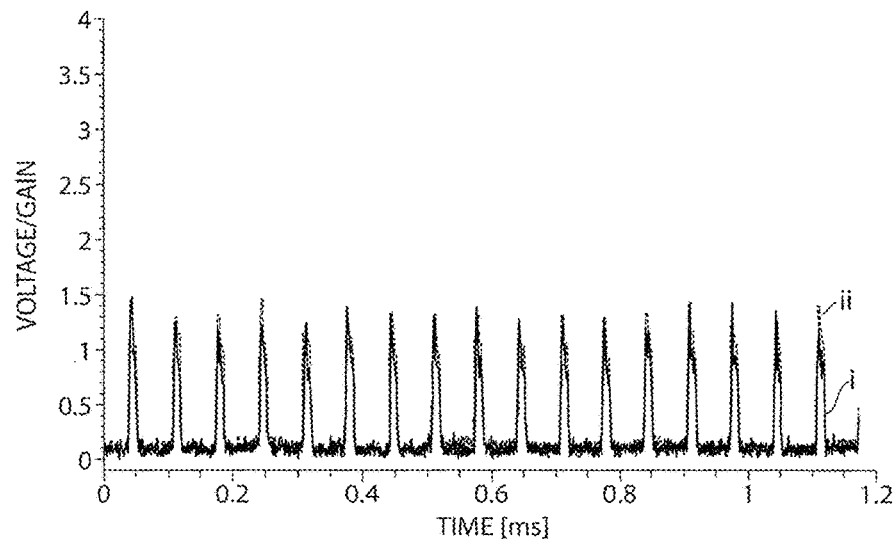
FIGS. 27A-27D shows the detection of droplets base on the detection of various intensities, according to one embodiment.
Figure 27B:
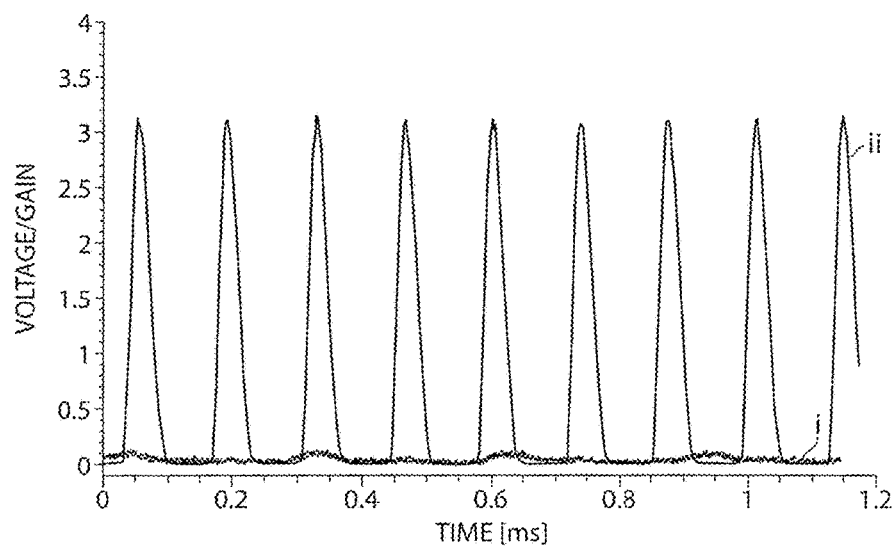
Figure 27C:
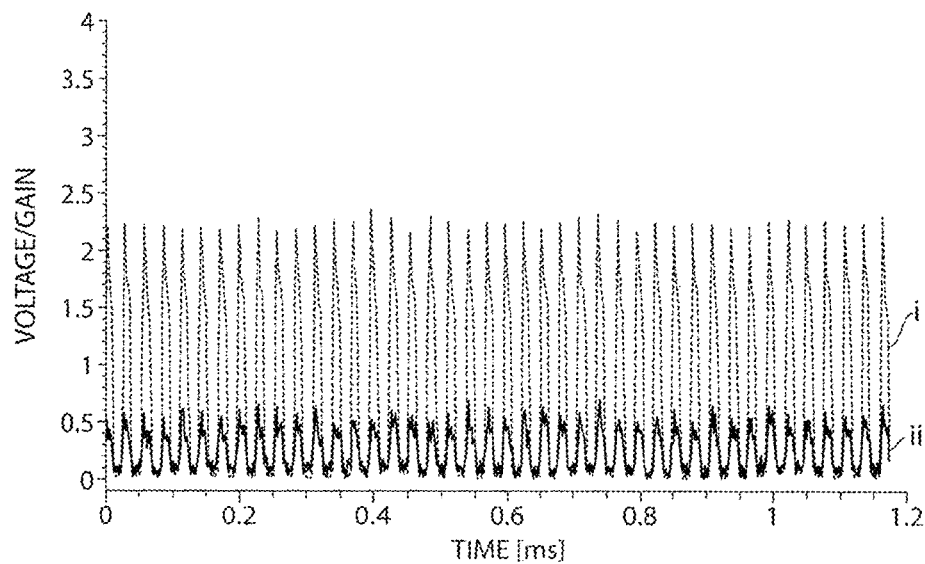
Figure 27D:
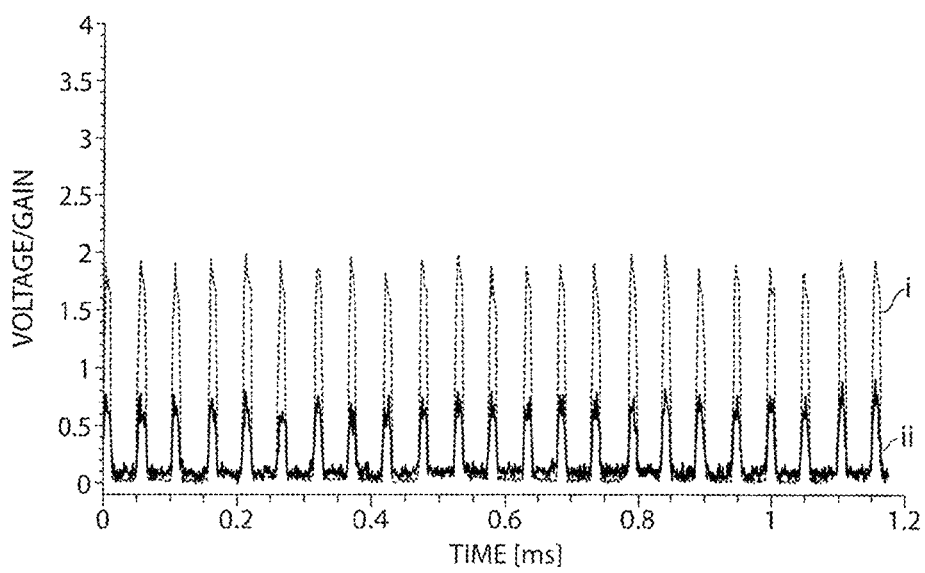

FIG. 24 shows an area of the system used in this example where the hybridization results were determined. In this system, the fused droplets 380 were released into a microfluidic channel 381 and passed past a light source 384 (e.g., laser line), one at a time (e.g., droplet 382), and the hybridization results were determined. Following determination, the droplets (e.g., droplet 386) continued to be flowed out of the microfluidic channel. FIG. 25A shows a schematic of the above described set-up. The droplet could also be deformed during determination, for example, as shown in FIG. 26.

FIGS. 27A-27D are graphs ((i) green, (ii) red)) of the quantitative results showing the velocity/gain vs. time (ms). These figures describes the detection of various labels using fluorescence. More specifically, FIG. 27 shows the red and green fluorescent signals for four different droplet types. The experimental procedure for this example was similar to that described above. In this example, a photomultiplier tube (PMT) was used for detection instead of a CCD detector. The four plots showed the red and green PMT signals for the four different types of droplets that were prepared. Each spike in the signals corresponded to a droplet that has flowed past the detector. As a droplet passed the detector the red and green lasers excited fluorescence that was imaged by the objected back onto the PMT.

Figure 28:
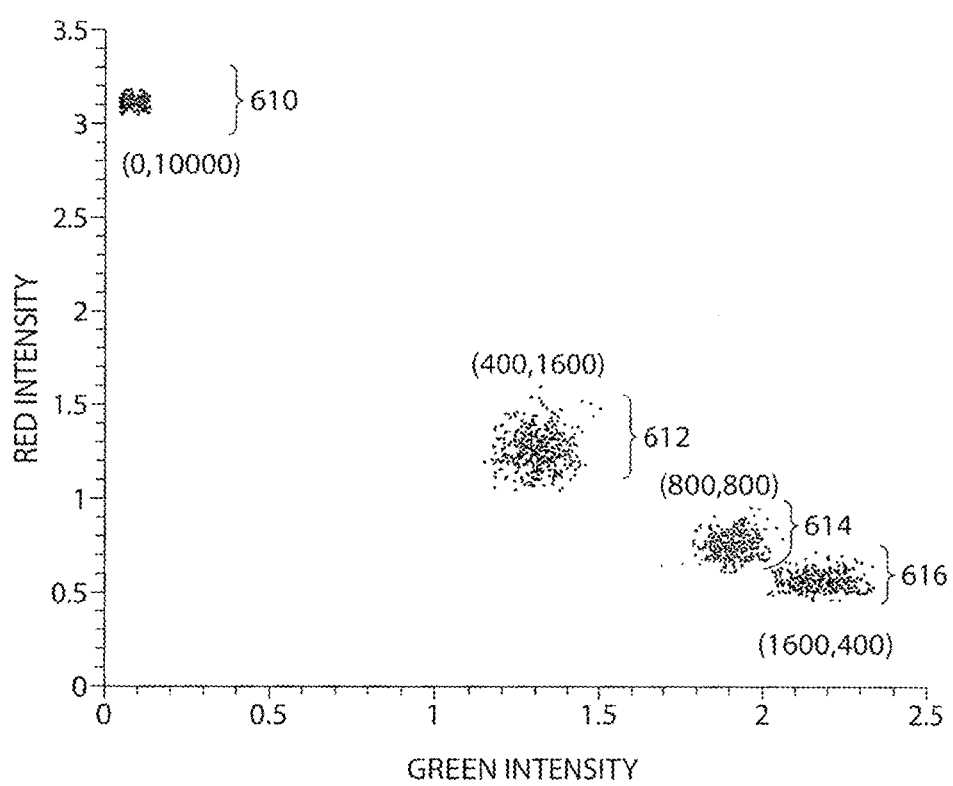
FIG. 28 shows a plot of a plurality of droplets comprising green and/or red dyes that were prepared and determined using methods of the present invention, according to one embodiment.

FIG. 28 shows the detection of droplets base on the detection of red and green intensities. The red and the green fluorescence intensity of the individual droplets were measured. Each spot of the plot represents a droplet that was detected. To produce this plot, four types of droplets were first prepared, each containing a unique combination of red and green fluorescent dye (as described above). For example, spots 610 represent droplets which comprised a small amount of green dye and a large amount of red dye, whereas the spots 616 represent droplets which comprised a large amount of green dye and a small amounted dye. The multiple spots in each location of the plot (e.g., 610, 612, 614, 616) represented multiple droplets which had approximately the same ratio of red and green dyes. To determine the droplets, a green and a red laser were focused on the droplets. The laser light caused the dyes contained within the droplets to fluoresce, and the emitting light that was captured by a microscope objective. This light was passed through a dichroic beam splitter which allowed the red light to pass and which reflected the green light. The light paths where then further filtered with red and green filters and then focused onto a PMT sensors. The PMT behind a red filter measured the intensity of the red light, while the PMT behind a green filter measured the intensity of the green light (e.g., for example, the device pictured in FIG. 11). The measurements were performed simultaneously, and the results were stored and processed by a computer. The computer processed the measurements to determine the amount of red and green fluorescence from each droplet. The results were then plotted on the graph shown in FIG. 28.

Figure 29:
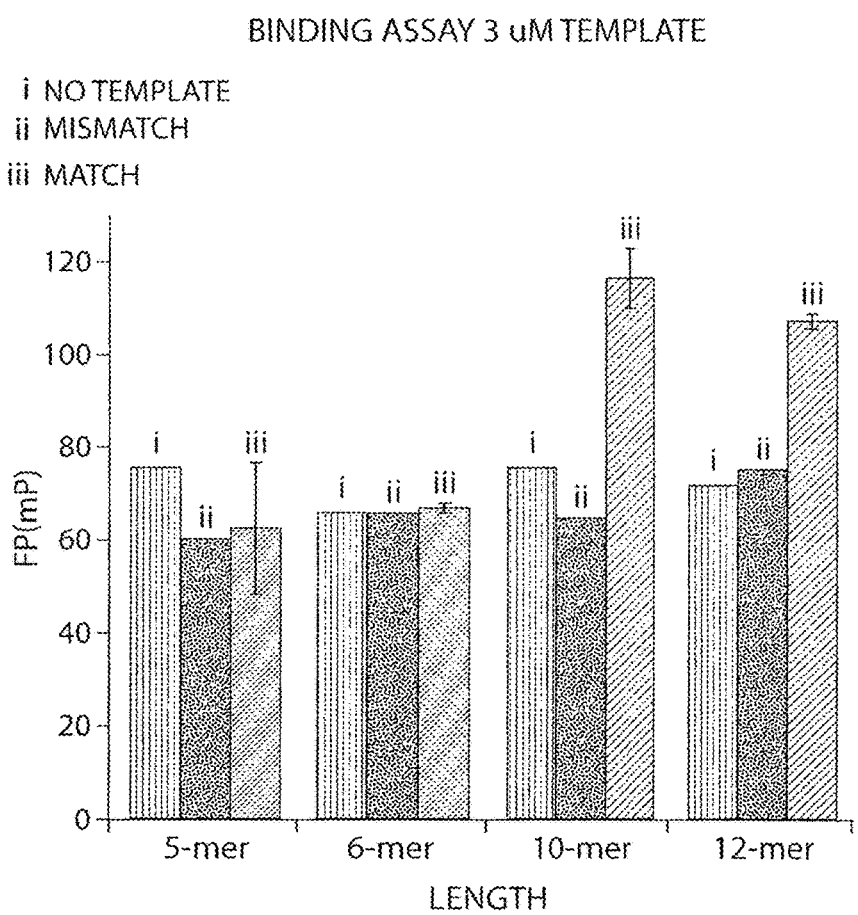
FIG. 29 shows the results of a binding assay of a 3 uM template with i) no target nucleic acid present, ii) mismatched target nucleic acid present, and iii) matched target nucleic acid present, according to some embodiments of the invention.

FIG. 29 shows the results of a binding assay of a 3 uM template. The plots show fluorescence polarization vs. length of the nucleic acid probe where there was i) no target nucleic acid present (e.g., template), ii) mismatched target nucleic acid present, and iii) matched target nucleic acid present.

In some cases, a computer was employed for the detection and/or quantification of the droplets. In instances where the detector was a PMT detector, LabView FPGA was used. The droplets were monitor with three PMTs, where each PMT was associated with a different filter and/or polarizer. Each PMT was assigned a number. PMT 1 monitored green light with parallel polarization. PMT 2 monitored green light with perpendicular polarization. PMT 3 monitored red light with no polarization. These three PMTs each outputted a voltage as a function of time that is proportional to the intensity of light that they detected as a function of time. These voltage time traces were sent a computer where they were analyzed.

The computer program searched one of the signals which was specified by the user to detect the droplets. As shown in FIG. 27, each droplet looks corresponded to a peak in voltage as a function of time. The leading edge of the peak was the leading edge of the droplet as it moved into the path of the laser beam. The peak corresponds to the droplet when it was in the center of the beam. The trailing edge was the trailing edge of the droplet as it moved out of the beam. The sequence with which the voltage changes as a function of time as a droplet flows past the laser and was used to determined whether a droplet was detected.

The computer monitored the signals to determined when the signal rose above a threshold level specified by the user. If a signal was above the threshold level, the difference in the voltage was calculated between this cycle and the previous cycle. If the difference was positive, the signal was rising, which indicated that this was the leading edge of a droplet. The computer continued to determined the signal of the droplet and stores the largest voltage associated with the droplet. When the signal drops below the threshold value, the trailing edge of the droplet is observed. The highest voltage for the droplet was determined and the signals from all three PMTs are correlated. The measurements which were associated with each droplets were the time at which the leading edge was detected, the value of the peak voltage, the time at which the trailing edge was detected, the duration that the voltage was above the threshold (e.g., the width of the peak, which, for constant flow speed is proportional to the length of the drop), and the integrated signal while the voltage was above the threshold. These measurements were collected for all three PMT signals which were collected simultaneously. The measurements were then further combined to determine at least one value selected by the user. For example, if fluorescence polarization measurements were desired, then the ratio of the green parallel and perpendicular peak or integrated intensity could be calculated. These numbers could also be compared with the specifications of the user to determine whether a droplet meets the criteria to further identify it as a useful droplet for determining and/or quantifying. In some instances, the droplet information (e.g., measurements) may be stored and/or the droplet may be selected for sorting.

EXAMPLE 12

The following example describes a system and method for droplet detection that allows real-time high-throughput data acquisition from emulsion based micro-fluidic assays.

The method described in this example was used to image microfluidic droplets, for example, microfluidic droplets comprising a fluorescent signal (e.g., microfluidic droplets comprising at least two fluorescent dye populations). Two groups of microfluidic droplets were prepared, one group of droplets comprising a fluorescein derivative dye (visible in the green wavelengths) and a second group of droplets comprising a Cy5™ dye (visible in the red wavelengths). The droplets were mixed together in the same container and were indistinguishable based upon size or morphology. The droplets were flowed into a basin channel as a mixed population and were visualized under a fluorescent microscope set-up. In this example, a green LED array was used to provide oblique lighting on the droplets and was placed at roughly a 55° angle and approximately 1 foot away from the microscope stage and produced droplet glare. FIG. 35 depicts an example of the experiment set-up. A fluorescent microscope was provided comprising an emission filter 520, a dichroic mirror 522, an arc lamp 524, an excitation filter 526, and an objective lens 528. The plurality of droplets was positioned on the microscope stage 530. Oblique lighting 532 was provided at an angle of approximately 55°. Light exciting the microscope 534 was recorded by a detector or an imager (e.g., a CCD camera, etc.).

In this example, images were captured by two CCD cameras, one placed under filters that only allow light in a narrow spectrum of the green wavelengths to pass, while the other camera was placed under filters that will only allow light in a narrow spectrum of the red wavelengths to pass. The capturing of frames on both cameras was synchronized to allow simultaneous capture of fluorescent information on both the green and red wavelengths. As the oblique lighting was from a green LED source, the droplet glare was only observed on the green wavelength capture.

Image frames from the green wavelength capture were processed by using a simple intensity threshold program to single-out the droplet glares on each droplet. In this case, human input told the software the angle and distance between a droplet glare and the center of the droplet; however, in some cases, this may be automated using software programs. In some embodiments, the angle and distance between a droplet glare and the center of the droplet will need to be recorded a single time, provide the instrumental set-up is not varied. Software was used to create a sampling mask relative to each droplet glare. The sampling mask was overlaid with the red and green wavelength camera images frame to create a marking system for each droplet that defines the same area within the boundary of the droplet where fluorescent intensity readings is to be taken. A computer merged the green wavelength image with the corresponding red wavelength image and formed a composite with information from both cameras. The mask generated from the droplet glares was used and fluorescent intensity information was gathered from the composite image. In this embodiment, the degree of accuracy in measuring the intensity from the droplets was high and there was little risk of sampling adjacent drops.

Figure 37:
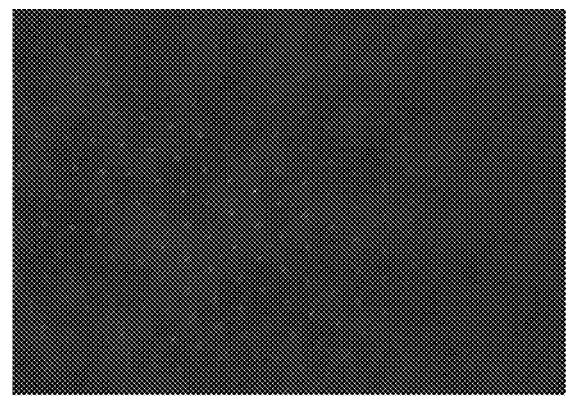
FIG. 37 shows a still frame from a CCD camera video capture of a plurality of microfluidic droplets comprising droplet glare under a green wavelength filter, according to one embodiment.
Figure 38:
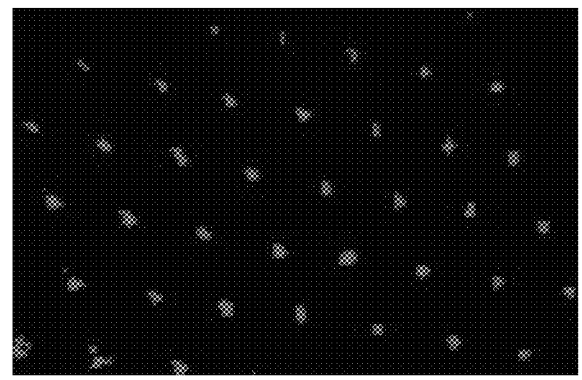
FIG. 38 shows the intensity threshold of a CCD camera image still of a plurality of droplets comprising droplet glare, according to one embodiment.
Figure 39A:
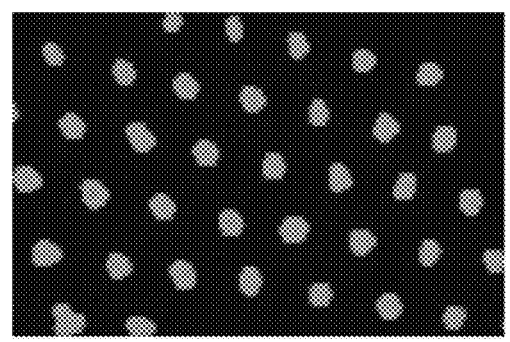
FIGS. 39A and 39B shows the mask and mask overlay produced, respectively, for fluorescent intensity readings of a plurality of droplets comprising droplet glare.
Figure 39B:
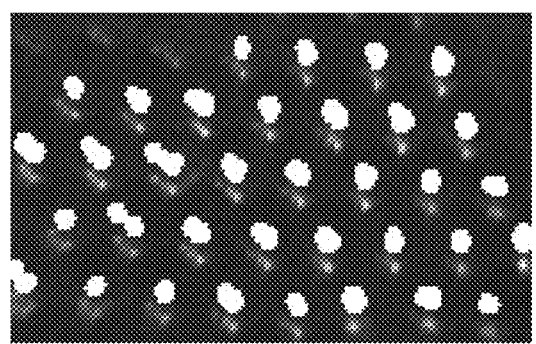
Figure 40:
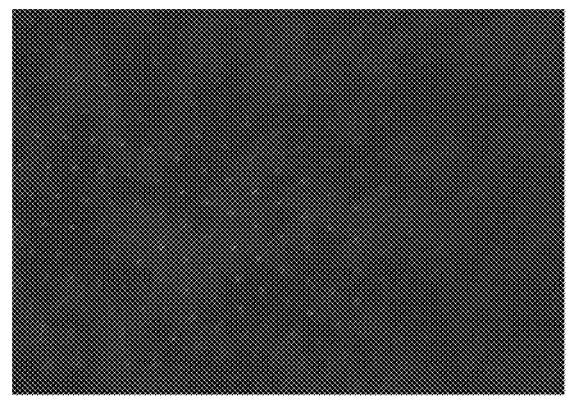
FIGS. 40 and 41 show images of a plurality of droplets from a green filter camera and a red filter camera, respectively, according to one embodiment.
Figure 41:
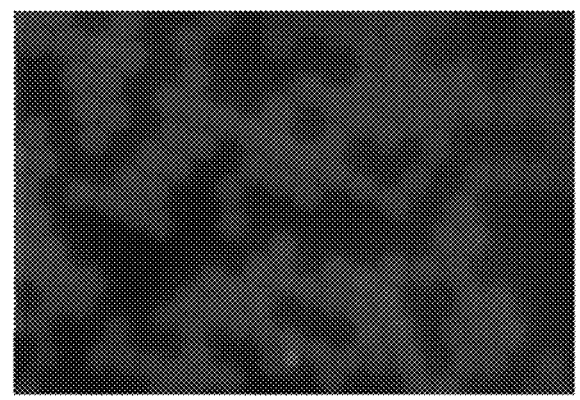
Figure 42:
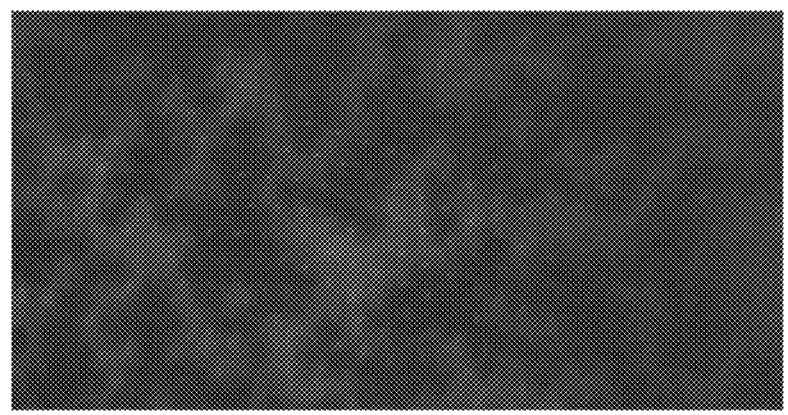
FIG. 42 shows the composite image comprising the overlay of the green and red camera data from FIGS. 40 and 41, respectively, showing two distinct populations of droplets.
Figure 43A:
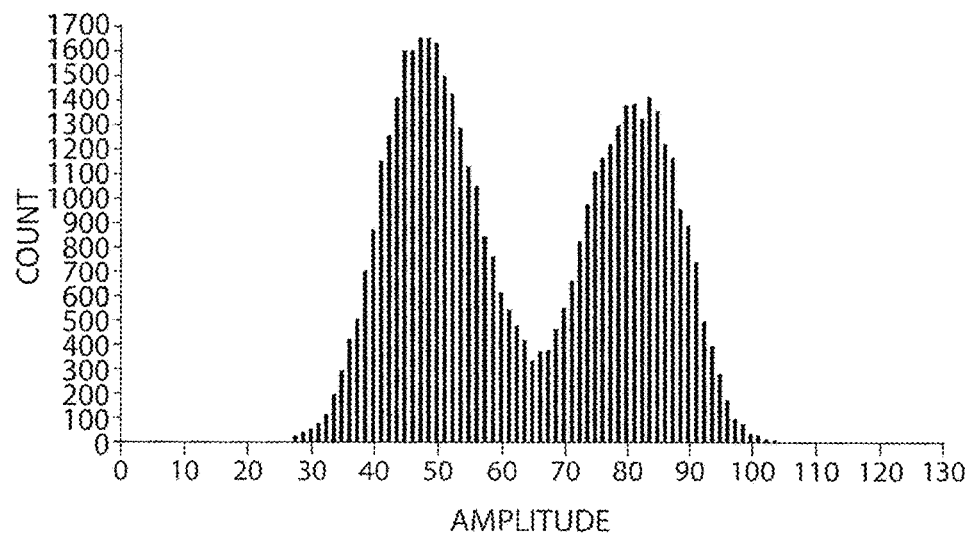
FIG. 43 shows a histogram of intensity count of over data points sampled in seconds from images, such as that shown in FIG. 42, according to one embodiment, with (A) the green channel and (B) the red channel showing bimodal distributions.
Figure 43B:
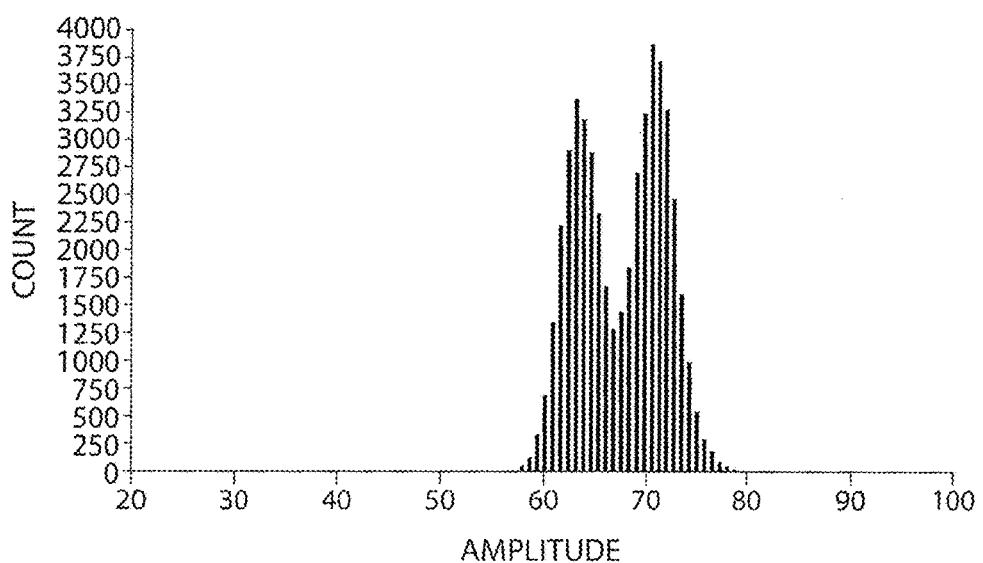

FIG. 37 shows a still frame from CCD camera video capture of the microfluidic droplets under the green wavelength filter. Note that in this image, the boundaries between the closely packed droplets are hard to distinguish while the droplet glares are readily visible. In this image, the droplets comprising fluorescein appear lighter in color while the droplets comprising Cy5™ appear darker in the image. FIG. 38 shows the intensity threshold of the CCD camera image still. FIGS. 39A and 39B shows the mask and mask overlay, respectively, for fluorescent intensity readings. FIG. 40 and FIG. 41 show the images from the green filter camera and the red filter camera, respectively. FIG. 42 shows the composite image comprising the overlay of the green and red camera data showing the two distinct populations of droplets comprising fluoroscein (darker grey) and Cy5™ (lighter grey). FIG. 43 shows a histogram of intensity count of over 50,000 data points sampled in seconds, with (a) the green channel and (b) the red channel showing an expected bimodal distribution.

The method describe in this example can be completed without computing intensive and may be done on the same image frames used for data acquisition. This may eliminates data acquisition as a bottle-neck in droplet based assays. For example, computer running the experiment as describe above acquired intensity data from a 12-bit 320×240 data stream at a rate of hundreds of frames per second. With a packed array of around 2,000 droplets/frame, this translates to the acquisition of processing of data from 200,000 droplets/second In some embodiments, the method as describe in this example may be advantageous when determining a plurality of droplets. The droplet glare may be more intense than the background and allow for easy identification of the position of a droplet, thereby allowing for simple determination of a droplet as compared to method that do not employ droplet glare. In some embodiments, software identification of the droplet glare may be completed using simple methods. The droplet glare can be used as a reference point as the droplet glares generally appear consistently in regards to both direction and distance from the center of each droplet. In additional, the second light source may be shone on the droplets at a variety of angles, and a particular angle may be selected (e.g., based on visual detection) that produces substantially focused glare. The angle may also be selected such that the droplet glare is offset with respect to the center of the droplets. Droplet glares which are offset from the center of the drop may allow for the same image frame for both droplet identification and data acquisition. Therefore, the oblique lighting does not have to be turned on and off and/or merged images do not have to be taken at slightly different time points.

While several embodiments of the invention have been described and illustrated herein, those of ordinary skill in the art will readily envision a variety of other means and/or structures for performing the functions and/or obtaining the results and/or one or more of the advantages described herein, and each of such variations or modifications is deemed to be within the scope of the present invention. More generally, those skilled in the art will readily appreciate that all parameters, dimensions, materials, and configurations described herein are meant to be exemplary and that the actual parameters, dimensions, materials, and configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and/or claimed. The present invention is directed to each individual feature, system, material and/or method described herein. In addition, any combination of two or more such features, systems, articles, materials and/or methods, if such features, systems, articles, materials and/or methods are not mutually inconsistent, is included within the scope of the present invention.

All definitions as used herein are solely for the purposes of this disclosure. These definitions should not necessarily be imputed to other commonly-owned patents and/or patent applications, whether related or unrelated to this disclosure. The definitions, as used herein, should be understood to control over dictionary definitions, definitions in documents incorporated by reference, and/or ordinary meanings of the defined terms.

It should also be understood that, unless clearly indicated to the contrary, in any methods claimed herein that include more than one act, the order of the acts of the method is not necessarily limited to the order in which the acts of the method are recited.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedure, Section 2111.03.

What is claimed is:

1. A method, comprising:
   providing a first microfluidic droplet containing a nucleic acid probe and at least three distinguishable identification elements, wherein each of the at least three distinguishable identification elements is associated with a different oligonucleotide sequence comprising at least one universal nucleic acid residue;
   providing a second microfluidic droplet comprising a target nucleic acid; and
   fusing at least some of the fluid in the first fluidic droplet and at least some of the fluid in the second microfluidic droplet to form a fused droplet.

2. The method of claim 1, comprising determining a sequence of at least a portion of the target nucleic acid.

3. The method of claim 1, further comprising determining at least a portion of the target nucleic acid by determining at least one of the at least three identification elements contained within the fused droplet.

4. The method of claim 1, further comprising determining at least one of the at least three identification elements.

5. The method of claim 1, wherein the nucleic acid probe contains at least four residues.

6. The method of claim 1, wherein the nucleic acid probe contains at least one locked nucleic acid residue.

7. The method of claim 1, further comprising determining association between the target nucleic acid and the nucleic acid probe.

8. The method of claim 1, wherein the nucleic acid probe comprises a quencher.

9. The method of claim 1, wherein the droplet contains four distinguishable identification elements.

10. The method of claim 1, wherein each of the at least three distinguishable identification elements is attached to the different oligonucleotide sequence.

11. The method of claim 1, wherein the first microfluidic droplet or the second microfluidic droplet comprises a ligase.

12. The method of claim 11, further comprising ligating the nucleic acid probe to one of the different oligonucleotide sequences associated with one of the at least three distinguishable identification elements.

13. The method of claim 1, wherein each of the different oligonucleotide sequences differs by one nucleic acid residue.

14. The method of claim 13, wherein the one nucleic acid residue is at the same location on each of the different oligonucleotide sequences.

15. The method of claim 1, wherein each of the different oligonucleotide sequences has a single non-universal nucleic acid residue.

16. A method, comprising:
   providing a first microfluidic droplet containing a nucleic acid probe and at least three distinguishable identification elements, wherein each distinguishable identification element is associated with a different oligonucleotide sequence;
   providing a second microfluidic droplet comprising a target nucleic acid;
   fusing at least some of the fluid in the first fluidic droplet and at least some of the fluid in the second microfluidic droplet to form a fused droplet; and
   ligating the nucleic acid probe to one of the different oligonucleotide sequences associated with one of the at least three distinguishable identification elements.

17. The method of claim 16, comprising determining a sequence of at least a portion of the target nucleic acid.

18. The method of claim 16, further comprising determining at least a portion of the target nucleic acid by determining at least one of the at least three identification elements contained within the fused droplet.

19. The method of claim 16, wherein each of the at least three distinguishable identification elements is attached to the different oligonucleotide sequence.

20. The method of claim 16, wherein each of the different oligonucleotide sequences differs by one nucleic acid residue.

* * * * *